(12) United States Patent
Song et al.

(10) Patent No.: US 11,545,630 B2
(45) Date of Patent: Jan. 3, 2023

(54) COMPOUND AND ORGANIC ELECTROLUMINESCENT DEVICE COMPRISING THE SAME

(71) Applicants: LG Display Co., Ltd., Seoul (KR); MATERIAL SCIENCE CO., LTD., Seoul (KR)

(72) Inventors: Inbum Song, Seoul (KR); Seunghee Yoon, Seoul (KR); Sunghoon Kim, Seoul (KR); Tae Wan Lee, Seoul (KR); Dong Hun Lee, Seoul (KR); Jeonghoe Heo, Seoul (KR); Seong-Min Park, Goyang-si (KR); Sunjae Kim, Seoul (KR)

(73) Assignees: LG Display Co., Ltd., Seoul (KR); MATERIAL SCIENCE CO., LTD., Seoul (KR)

( * ) Notice: Subject to any disclaimer, the term of this patent is extended or adjusted under 35 U.S.C. 154(b) by 391 days.

(21) Appl. No.: 16/675,197

(22) Filed: Nov. 5, 2019

(65) Prior Publication Data
US 2020/0144509 A1 May 7, 2020

(30) Foreign Application Priority Data

Nov. 5, 2018 (KR) .................. 10-2018-0134472
Oct. 14, 2019 (KR) .................. 10-2019-0126903

(51) Int. Cl.
*H01L 51/50* (2006.01)
*H01L 51/00* (2006.01)
(Continued)

(52) U.S. Cl.
CPC ........ *H01L 51/0061* (2013.01); *C07D 209/86* (2013.01); *C09K 11/06* (2013.01); *H01L 51/006* (2013.01); *C09K 2211/10* (2013.01); *H01L 27/1225* (2013.01); *H01L 27/3248* (2013.01); *H01L 29/7869* (2013.01); *H01L 51/001* (2013.01); *H01L 51/0052* (2013.01); *H01L 51/0058* (2013.01); *H01L 51/0072* (2013.01); *H01L 51/508* (2013.01); *H01L 51/5012* (2013.01); *H01L 51/5064* (2013.01); *H01L 51/5088* (2013.01); *H01L 51/5092* (2013.01);
(Continued)

(58) Field of Classification Search
None
See application file for complete search history.

(56) References Cited

U.S. PATENT DOCUMENTS

2014/0374706 A1* 12/2014 Hong .................. C07D 487/04
257/40
2017/0213980 A1* 7/2017 Nakano .................. C07F 7/081
2020/0106017 A1 4/2020 Ha et al.

FOREIGN PATENT DOCUMENTS

CN 108752221 A 11/2018
CN 108976162 A 12/2018
(Continued)

OTHER PUBLICATIONS

Korea Association for Photonics Industry Development (KAPID) "OLED Patent Analysis and Strategy Establishment Service Report," Presentation Letter, Jul. 2015 (w/ partial English translation), 192 pages.

*Primary Examiner* — Gregory D Clark
(74) *Attorney, Agent, or Firm* — Seed IP Law Group LLP

(57) ABSTRACT

Organic electroluminescent devices with lowered driving voltages, and enhanced efficiencies and lifetimes are provided.

11 Claims, 1 Drawing Sheet

(51) Int. Cl.
  *C09K 11/06* (2006.01)
  *C07D 209/86* (2006.01)
  *H01L 51/56* (2006.01)
  *H01L 51/52* (2006.01)
  *H01L 27/32* (2006.01)
  *H01L 27/12* (2006.01)
  *H01L 29/786* (2006.01)

(52) U.S. Cl.
  CPC .......... *H01L 51/5253* (2013.01); *H01L 51/56* (2013.01); *H01L 2251/558* (2013.01)

(56) References Cited

FOREIGN PATENT DOCUMENTS

| | | |
|---|---|---|
| CN | 110799486 A | 2/2020 |
| JP | 2009-76817 A | 4/2009 |
| KR | 10-2016-0059602 A | 5/2016 |
| KR | 20180093354 A | 8/2018 |

* cited by examiner

COMPOUND AND ORGANIC ELECTROLUMINESCENT DEVICE COMPRISING THE SAME

CROSS-REFERENCE TO RELATED APPLICATIONS

This application claims the priority of Korean Patent Application No. 10-2018-0134472 filed on Nov. 5, 2018 and Korean Patent Application No. 10-2019-0126903 filed on Oct. 14, 2019 in the Korean Intellectual Property Office, the disclosures of which are hereby incorporated by reference in their entirety.

BACKGROUND

Technical Field

The present disclosure relates to a novel organic compound and an organic electroluminescent device including the same.

Description of the Related Art

Recently, as a size of a display device increases, interest in a flat panel display device having a small space occupation is increasing. As one of the flat panel display devices, an organic light emitting display device including an organic electroluminescent device (organic light emitting diode: OLED) is rapidly developing.

In the organic light emitting diode, electrons and holes are paired to form excitons when charges are injected into a light emitting layer formed between a first electrode and a second electrode. Thus, energy of the excitons may be converted to light. The organic light emitting diode may be driven at a lower voltage and consume less power than the conventional display technology. The organic light emitting diode may render excellent color. A flexible substrate may be applied to the organic light emitting diode which may have various applications.

BRIEF SUMMARY

One purpose of the present disclosure is to provide an organic electroluminescent device with lowered driving voltage, and enhanced efficiency and lifetime.

Purposes of the present disclosure are not limited to the above-mentioned purpose. Other purposes and advantages of the present disclosure which are not mentioned above may be understood from following descriptions and more clearly understood from embodiments of the present disclosure. Further, it will be readily appreciated that the purposes and advantages of the present disclosure may be realized by features and combinations thereof as disclosed in the claims.

A novel compound according to one embodiment of the present disclosure is represented by the following Chemical Formula 1:

Chemical Formula 1

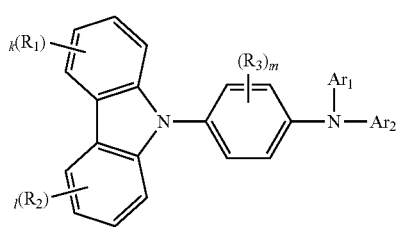

In the Chemical Formula 1, $Ar_1$ is represented by the following Chemical Formula 2:

Chemical Formula 2

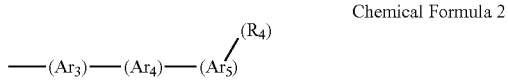

$Ar_2$ is represented by a following Chemical Formula 3:

Chemical Formula 3

Each of $Ar_3$ to $Ar_7$ independently represents a substituted or unsubstituted C3 to C30 aryl group, and at least one of $Ar_3$ to $Ar_7$ represents a substituted or unsubstituted C8 to C30 aryl group.

Each of $R_1$ to $R_5$ independently represents one selected from the group consisting of hydrogen, deuterium, substituted or unsubstituted C1 to C30 alkyl, substituted or unsubstituted C3 to C30 cycloalkyl, substituted or unsubstituted C6 to C30 aryl, and substituted or unsubstituted C2 to C30 heteroaryl.

Each of k, l and m independently denotes an integer of 0 to 4. When k is 2 to 4, each of a plurality of $R_1$ is independently defined as described above, and the plurality of $R_1$ are the same as or different from each other. When l is 2 to 4, each of a plurality of $R_2$ is independently defined as described above and the plurality of $R_2$ are the same as or different from each other. When m is 2 to 4, each of a plurality of $R_3$ is independently defined as described above and the plurality of $R_3$ are the same as or different from each other.

An organic electroluminescent device according to one embodiment of the present disclosure may include a first electrode, a second electrode, and an organic layer formed between the first electrode and the second electrode. The organic layer includes a light emission layer. The organic layer includes a hole transport layer and a hole transport auxiliary layer between the first electrode and the light emission layer. The hole transport auxiliary layer contains the compound represented by the above Chemical Formula 1.

Effects of the present disclosure are as follows but are not limited thereto.

In accordance with the present disclosure, an organic electroluminescent device with lowered driving voltage, and enhanced efficiency and lifetime may be realized.

In addition to the effects as described above, specific effects of the present disclosure are described together with specific details for carrying out the present disclosure.

DETAILED DESCRIPTION

Figure 1:
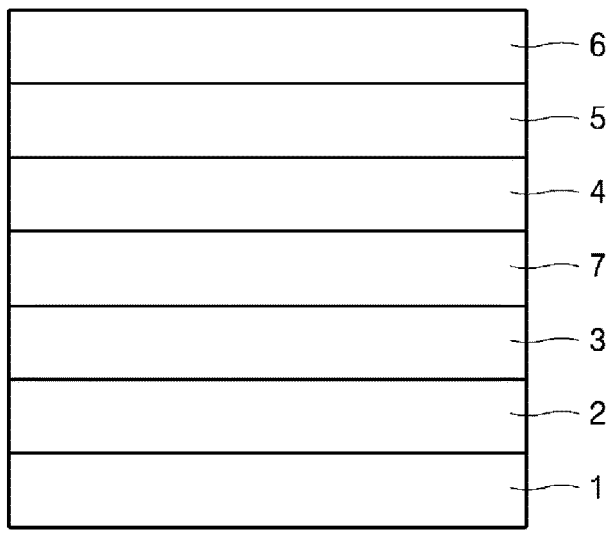
FIG. 1 is a schematic cross-sectional view of an organic electroluminescent device containing a compound represented by Chemical Formula 1 according to one embodiment of the present disclosure.

For simplicity and clarity of illustration, elements in the figures are not necessarily drawn to scale. The same reference numbers in different figures denote the same or similar elements, and as such perform similar functionality. Furthermore, in the following detailed description of the present disclosure, numerous specific details are set forth in order to provide a thorough understanding of the present disclosure. In other instances, well-known methods, procedures, components, and circuits have not been described in detail so as not to unnecessarily obscure aspects of the present disclosure.

Examples of various embodiments are illustrated and described further below. It will be understood that the description herein is not intended to limit the claims to the specific embodiments described. On the contrary, it is intended to cover alternatives, modifications, and equivalents as may be included within the spirit and scope of the present disclosure as defined by the appended claims.

The terminology used herein is for the purpose of describing particular embodiments only and is not intended to be limiting of the present disclosure. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. As used herein, the term "and/or" includes any and all combinations of one or more of the associated listed items. Expression such as "at least one of" when preceding a list of elements may modify the entire list of elements and may not modify the individual elements of the list.

It will be understood that, although the terms "first", "second", "third", and so on may be used herein to describe various elements, components, regions, layers and/or sections, these elements, components, regions, layers and/or sections should not be limited by these terms. These terms are used to distinguish one element, component, region, layer or section from another element, component, region, layer or section. Thus, a first element, component, region, layer or section described below could be termed a second element, component, region, layer or section, without departing from the spirit and scope of the present disclosure.

In addition, it will also be understood that when a first element or layer is referred to as being present "on" or "beneath" a second element or layer, the first element may be disposed directly on or beneath the second element or may be disposed indirectly on or beneath the second element with a third element or layer being disposed between the first and second elements or layers. It will be understood that when an element or layer is referred to as being "connected to", or "coupled to" another element or layer, it can be directly on, connected to, or coupled to the other element or layer, or one or more intervening elements or layers may be present. In addition, it will also be understood that when an element or layer is referred to as being "between" two elements or layers, it can be the only element or layer between the two elements or layers, or one or more intervening elements or layers may also be present.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

As used herein, the term "unsubstituted" means that a hydrogen atom has been substituted. In this case, the hydrogen atom includes protium, deuterium and tritium.

As used herein, a substituent in the term "substituted" may include one selected from the group consisting of, for example, hydrogen, deuterium, an alkyl group of 1 to 20 carbon atoms unsubstituted or substituted with halogen, an alkoxy group having 1 to 20 carbon atoms unsubstituted or substituted with halogen, halogen, a cyano group, a carboxy group, a carbonyl group, an amine group, an alkylamine group having 1 to 20 carbon atoms, a intro group, an alkylsilyl group having 1 to 20 carbon atoms, an alkoxysilyl group having 1 to 20 carbon atoms, a cycloalkylsilyl group having 3 to 30 carbon atoms, an arylsilyl group having 5 to 30 carbon atoms, an aryl group having 5 to 30 carbon atoms, an arylamine group having 5 to 30 carbon atoms, a heteroaryl group having 4 to 30 carbon atoms, and a combination thereof. However, the present disclosure is not limited thereto.

As used herein, the term "hetero" as used in 'hetero aromatic ring', 'heterocycloalkylene group', 'heteroarylene group', 'heteroaryl alkylene group', 'hetero oxy arylene group', 'heterocycloalkyl group, 'heteroaryl group, "heteroaryl alkyl group, 'hetero oxy aryl group', and 'heteroaryl amine group' means that one or more carbon atoms, for example, 1 to 5 carbon atoms among carbon atoms constituting the aromatic or alicyclic ring are substituted with at least one hetero atom selected from the group consisting of N, O, S and combinations thereof.

As used herein, the phase "combinations thereof" as used in the definition of the substituent means that two or more substituents are bonded to each other via a linking group or two or more substituents are bonded to each other via condensation, unless otherwise defined.

Hereinafter, a novel compound and an organic electroluminescent device containing the same according to some embodiments of the present disclosure will be described.

According to one embodiment of the present disclosure, there is provided a novel compound represented by the following Chemical Formula 1:

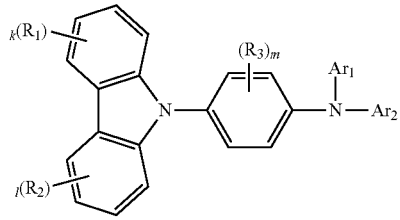

Chemical Formula 1

In the Chemical Formula 1, $Ar_1$ is represented by the following Chemical Formula 2:

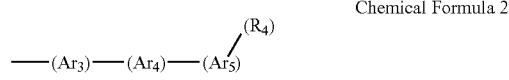

Chemical Formula 2

Ar₂ is represented by the following Chemical Formula 3:

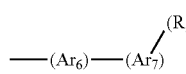

Chemical Formula 3

Each of $Ar_3$ to $Ar_7$ independently represents a substituted or unsubstituted C3 to C30 aryl group, and at least one of $Ar_3$ to $Ar_7$ represents a substituted or unsubstituted C8 to C30 aryl group.

Each of $R_1$ to $R_5$ independently represents one selected from the group consisting of hydrogen, deuterium, substituted or unsubstituted C1 to C30 alkyl, substituted or unsubstituted C3 to C30 cycloalkyl, substituted or unsubstituted C6 to C30 aryl, and substituted or unsubstituted C2 to C30 heteroaryl.

Each of k, l and m independently denotes an integer of 0 to 4. When k is 2 to 4, each of a plurality of $R_1$ is independently defined as described above, and the plurality of $R_1$ are the same as or different from each other. When l is 2 to 4, each of a plurality of $R_2$ is independently defined as described above and the plurality of $R_2$ are the same as or different from each other. When m is 2 to 4, each of a plurality of $R_3$ is independently defined as described above and the plurality of $R_3$ are the same as or different from each other.

In one embodiment, each of $Ar_3$ to $Ar_7$ independently represents a substituted or unsubstituted C8 to C30 condensed polycyclic group.

In one embodiment, each of $Ar_3$ to $Ar_7$ independently represents substituted or unsubstituted naphthylene, substituted or unsubstituted phenanthrene, substituted or unsubstituted anthracene, or substituted or unsubstituted pyrene.

Specifically, a compound represented by the above Chemical Formula 1 may be represented by one of the following compounds. However, the present disclosure is not limited thereto.

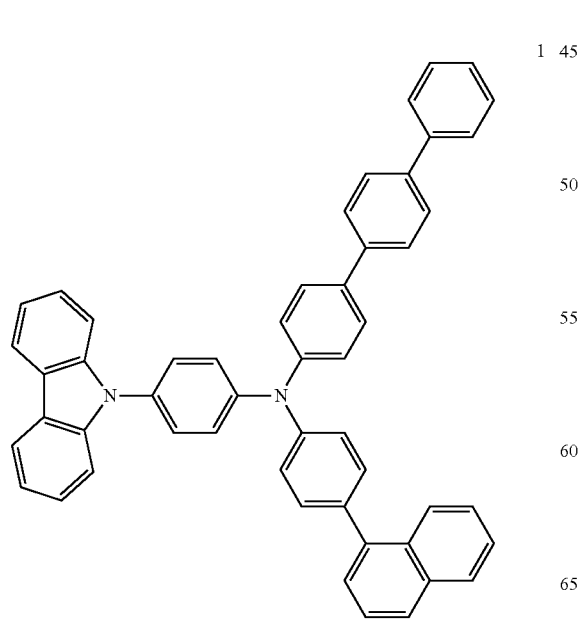

1

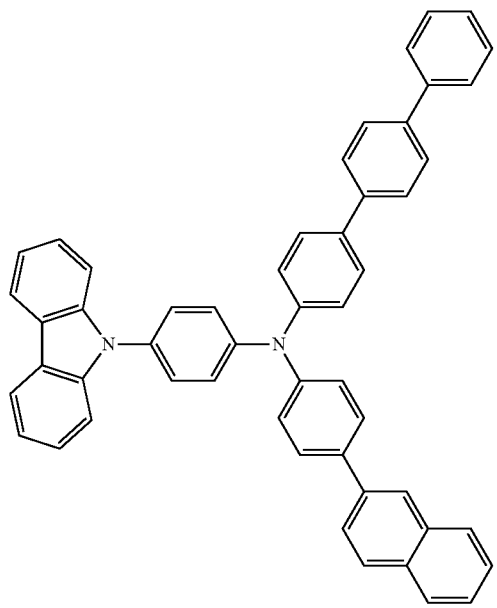

2

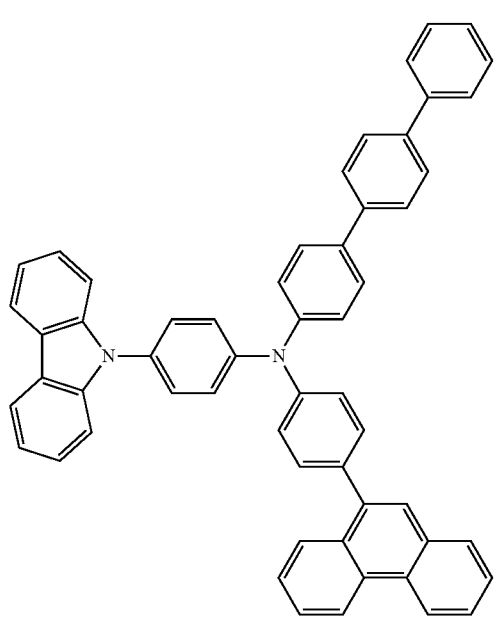

3

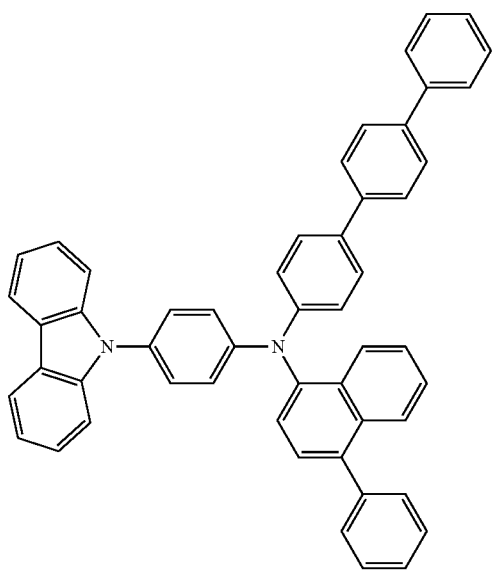
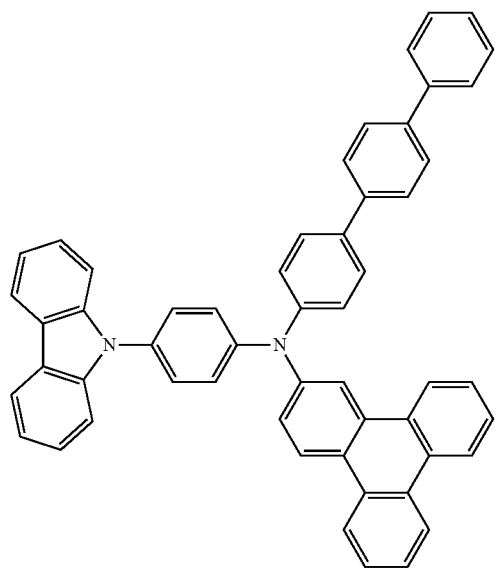
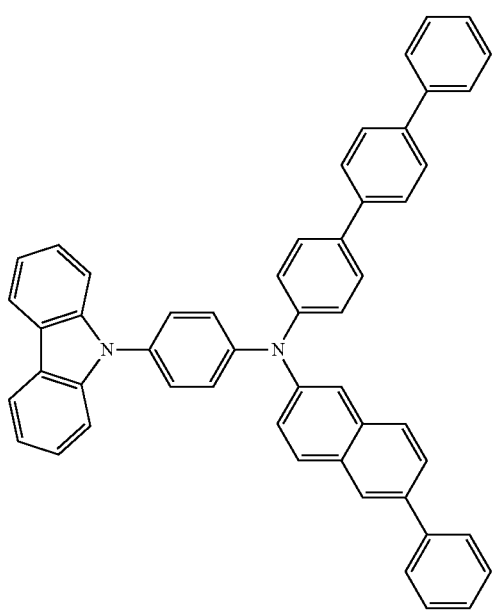
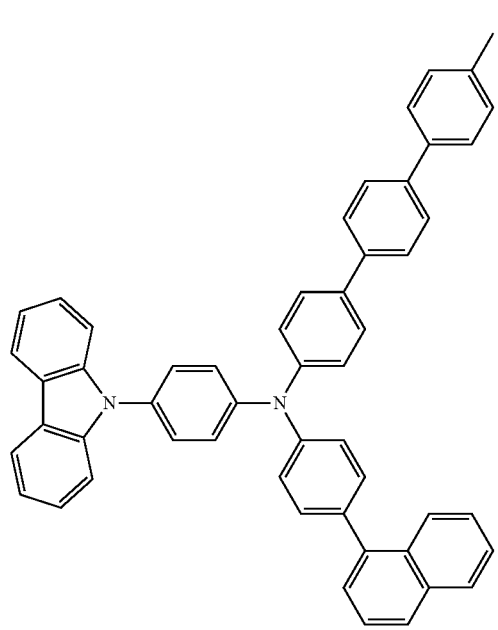

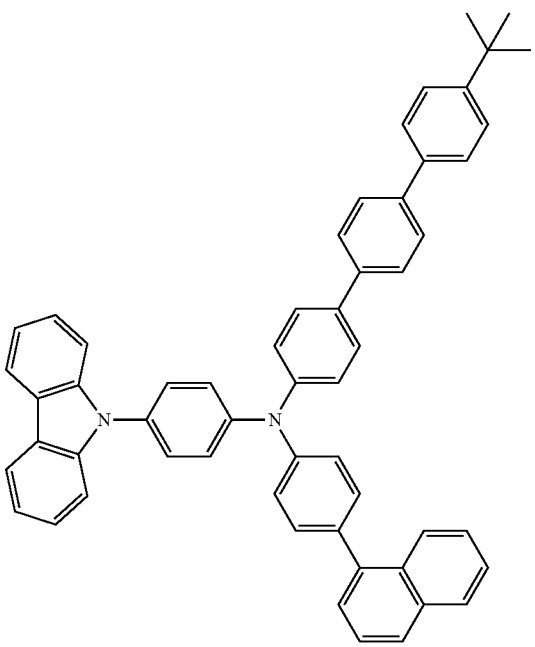
8
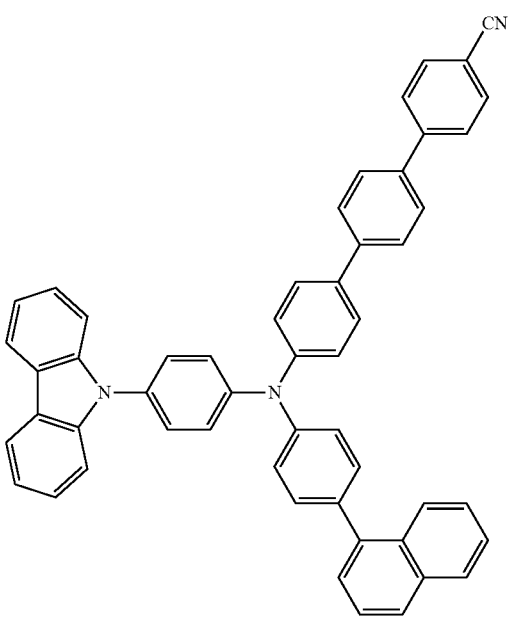
10
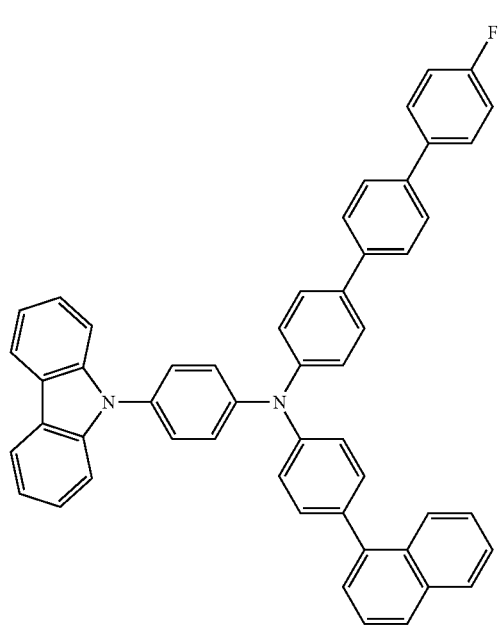
9

12
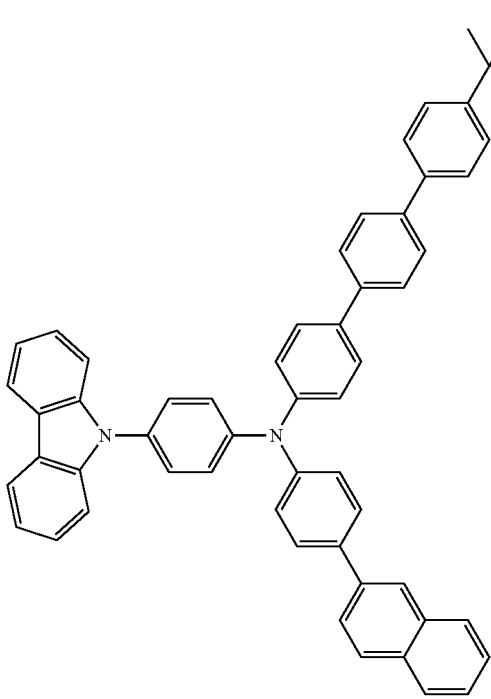
13
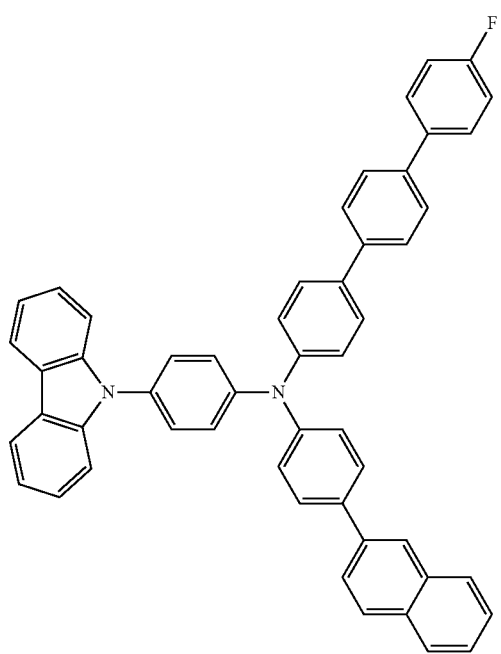
14
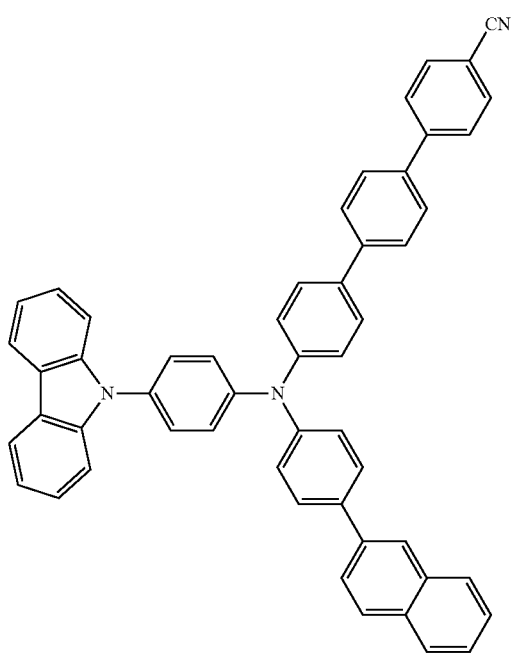
15
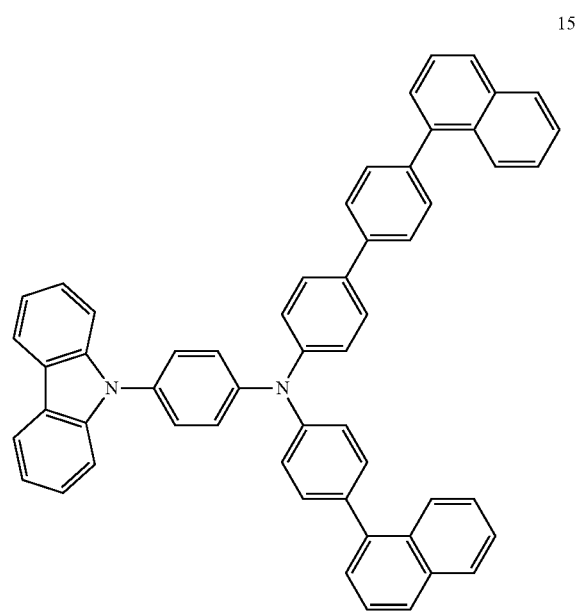

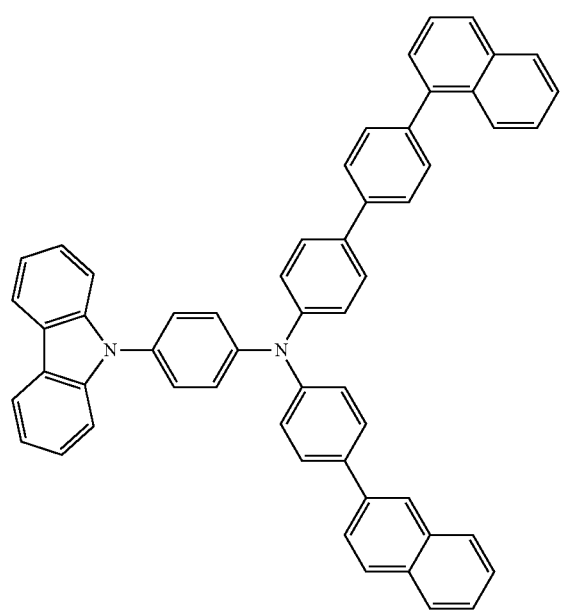
16
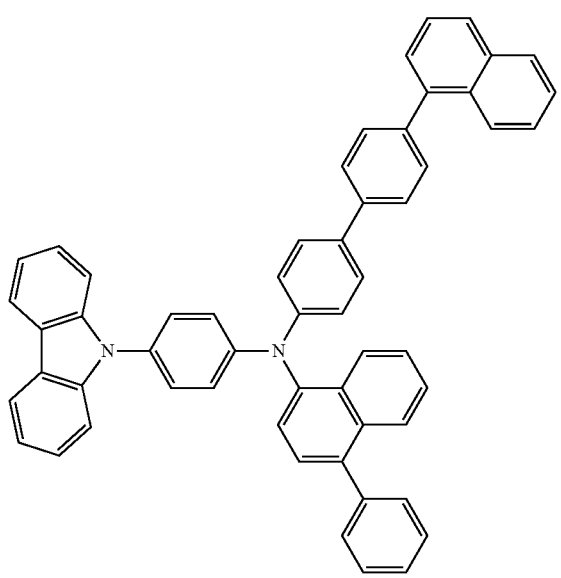
18
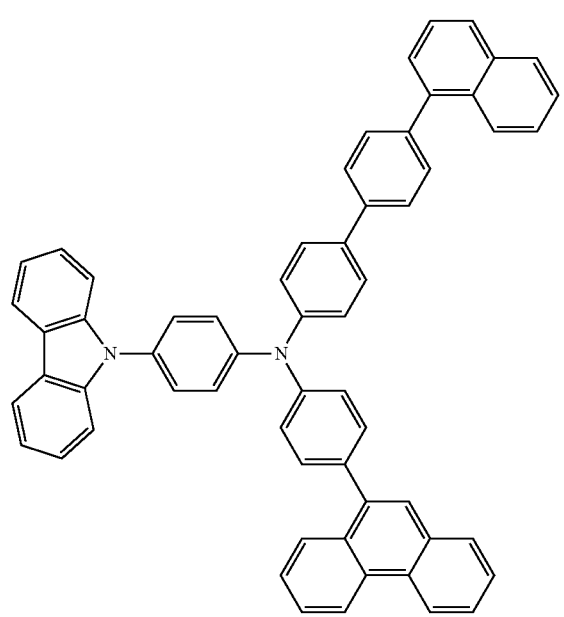
17

20
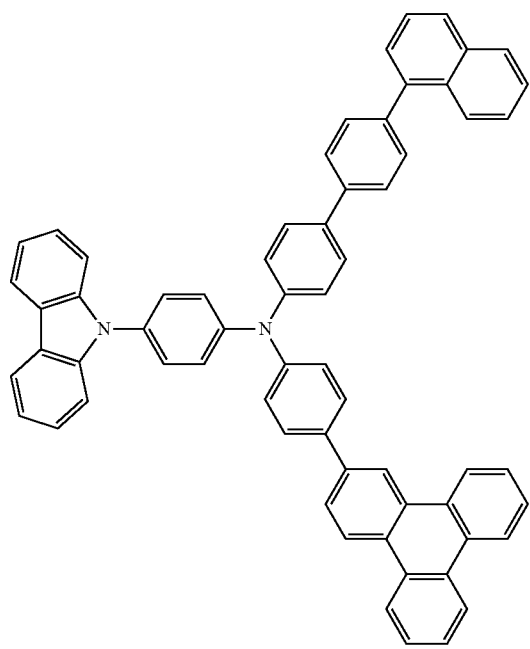
21
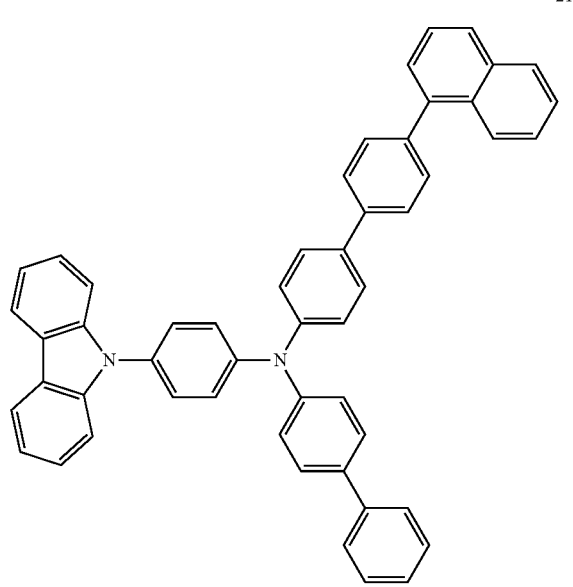
22
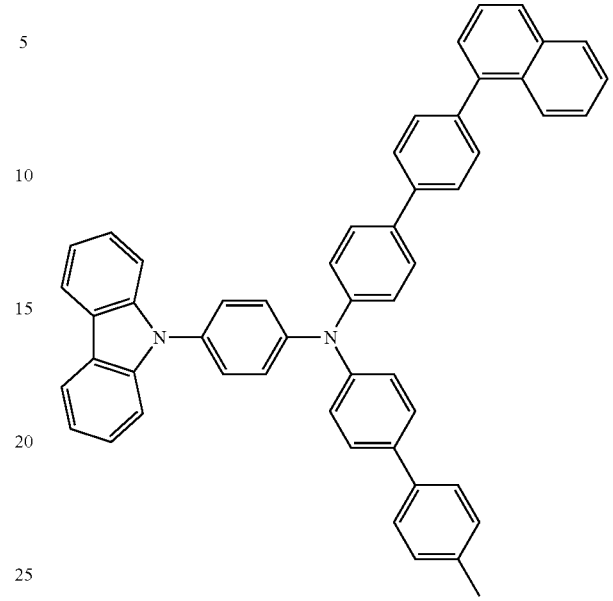
23
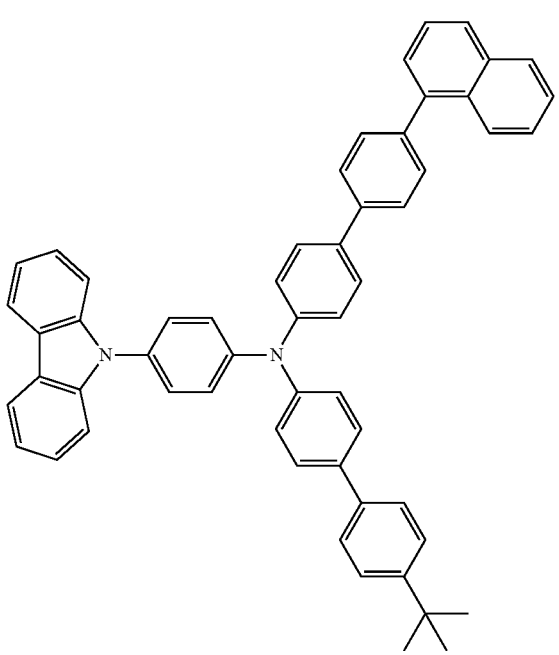

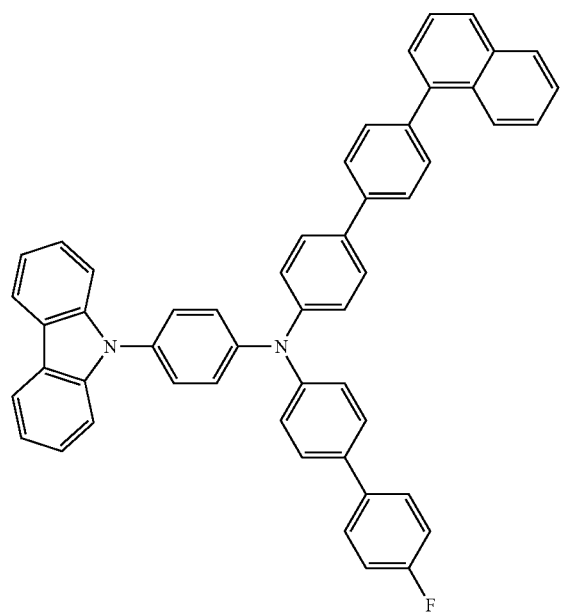
24
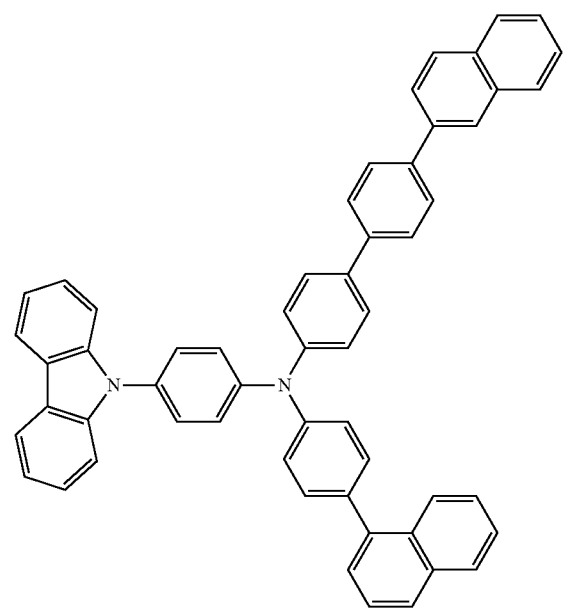
26
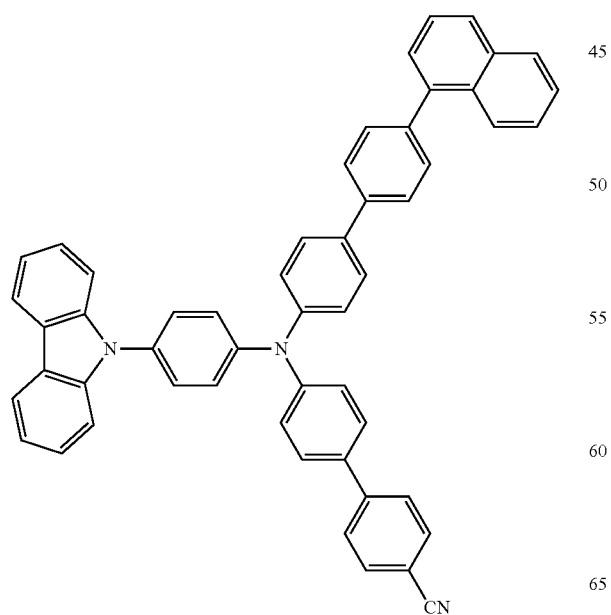
25
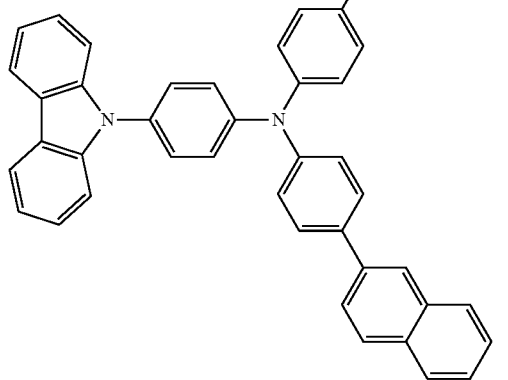
27

28
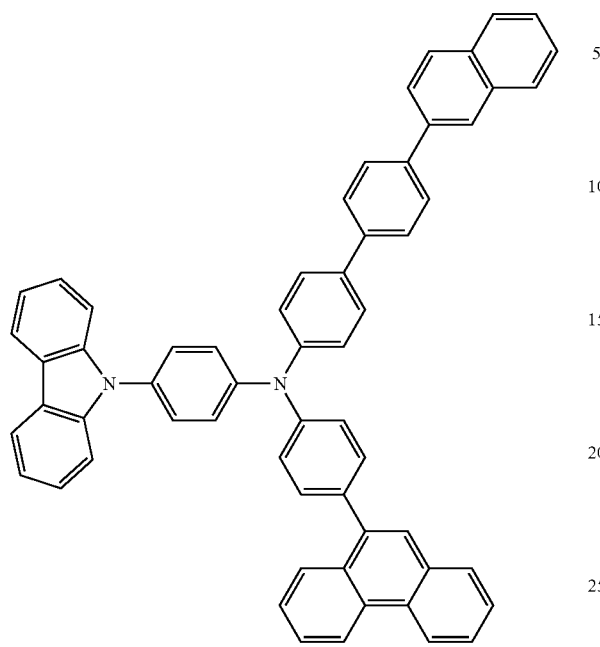
30
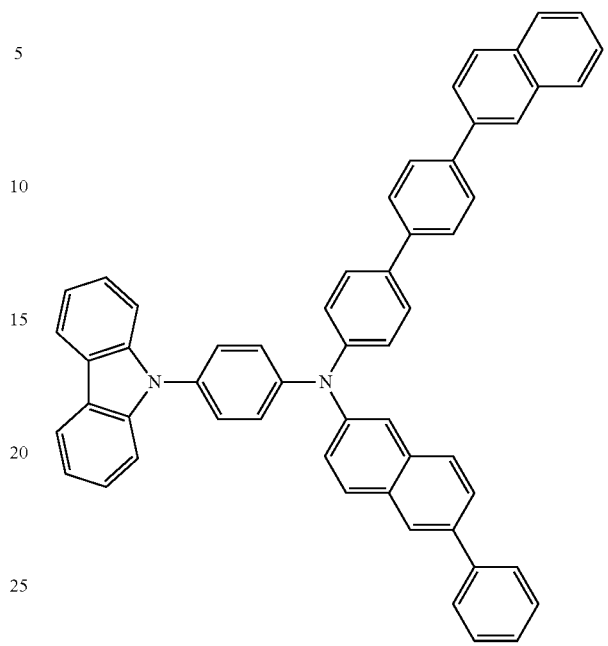
29
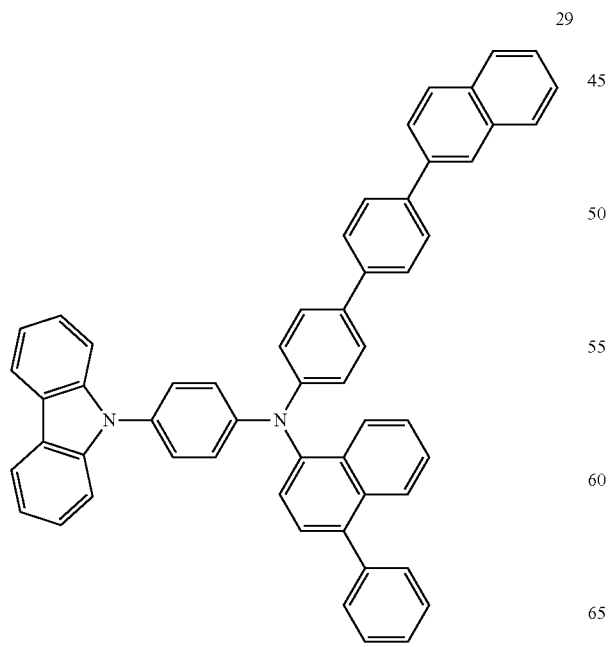
31
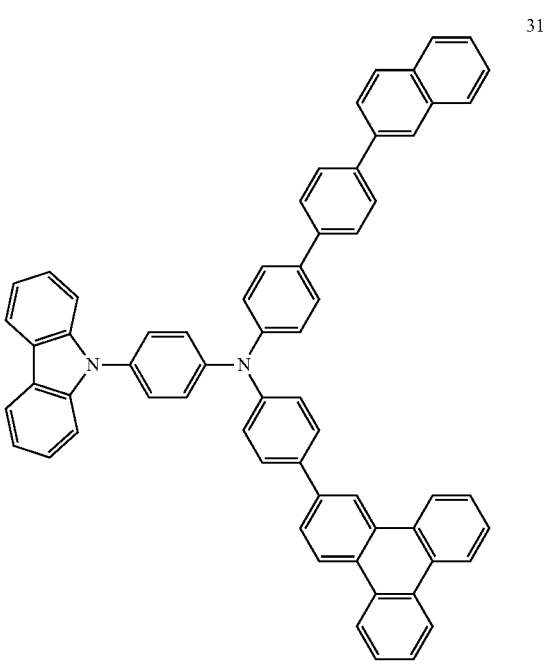

32
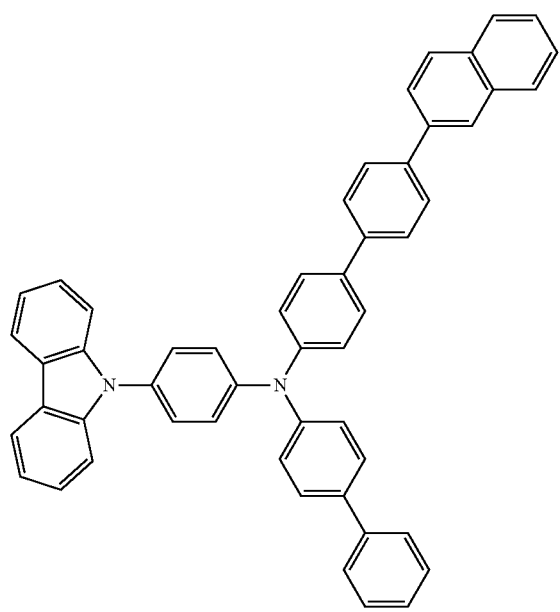
34
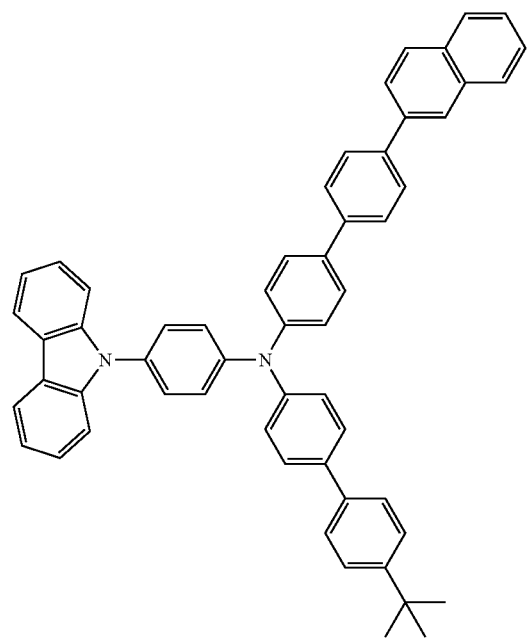
33
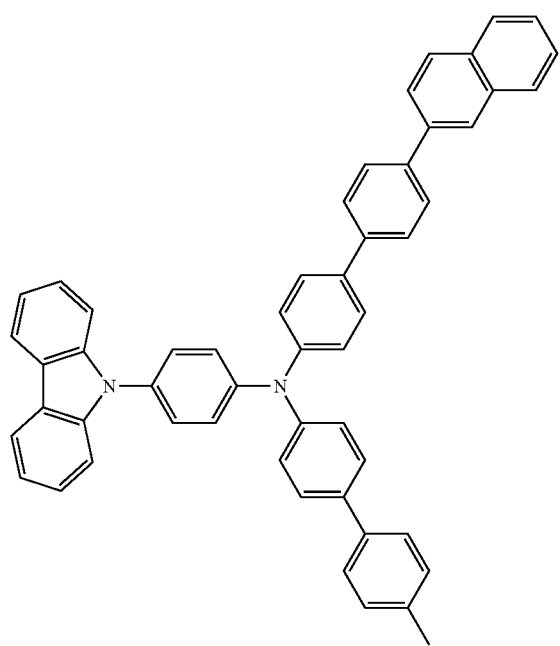
35
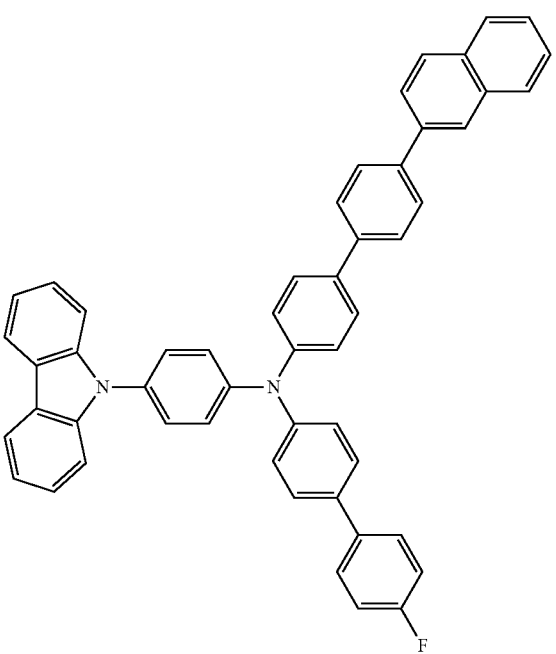

36
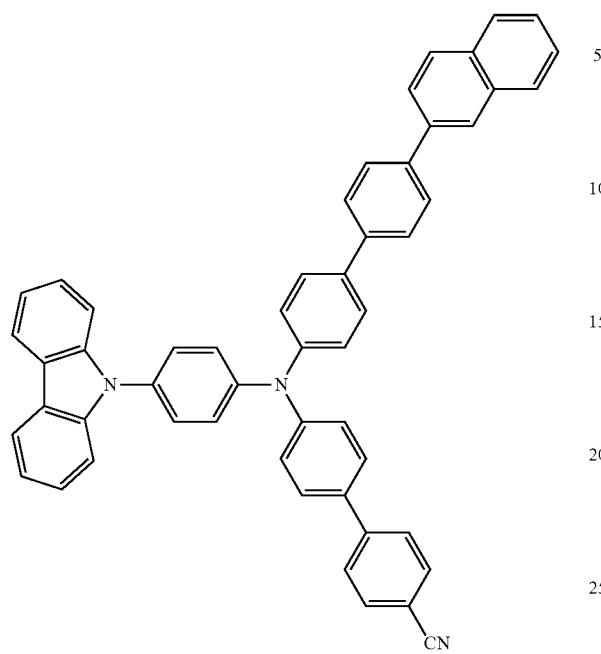
37
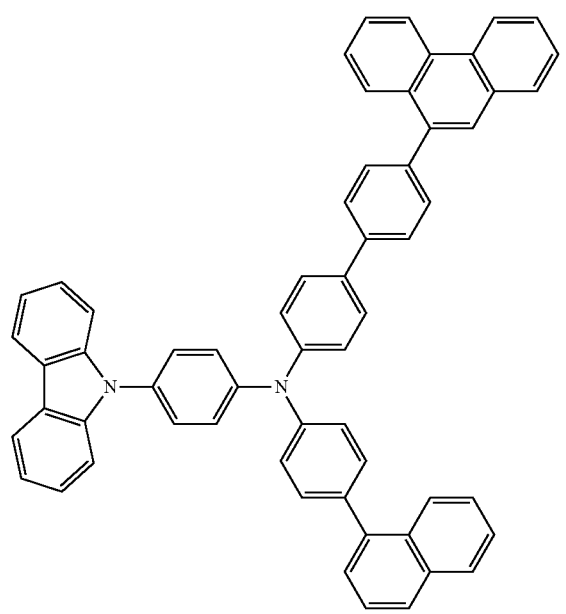
38
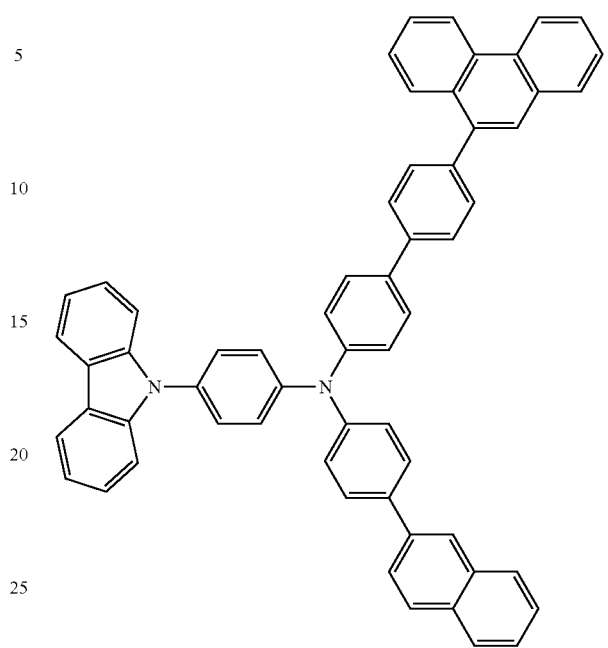
39
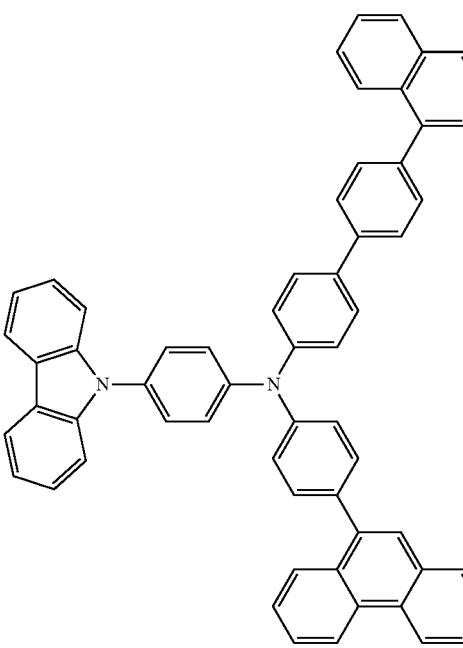

40
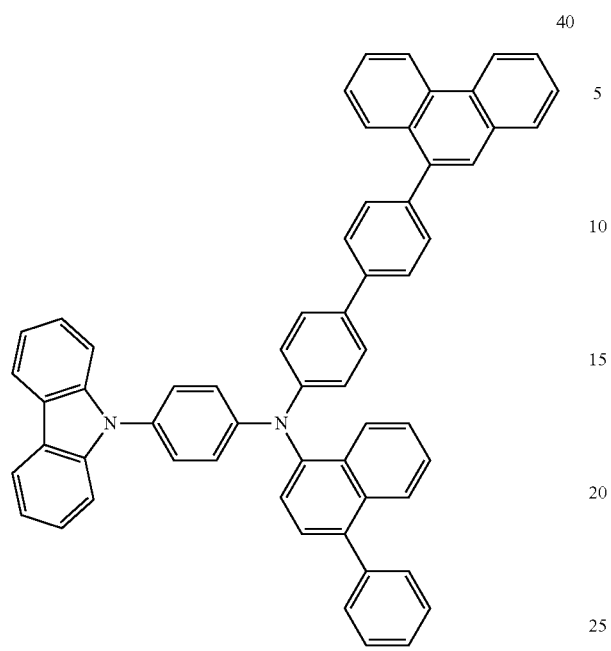
41
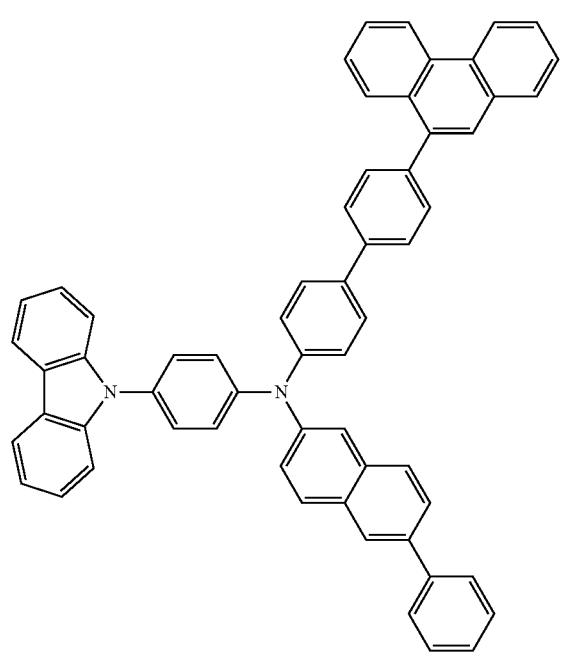
42
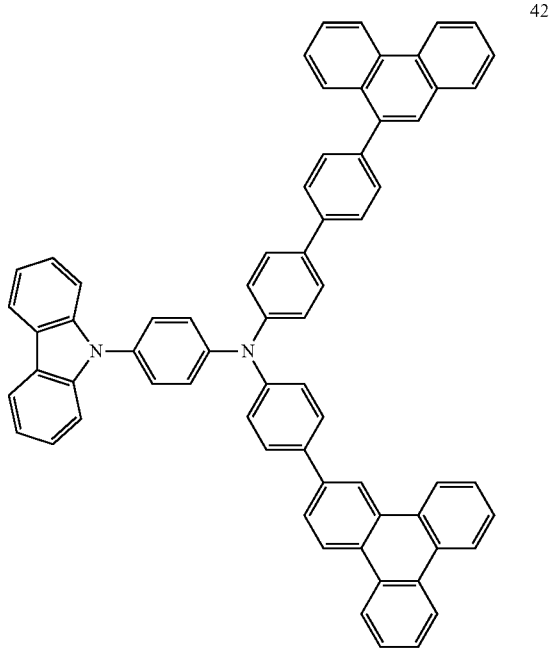
43
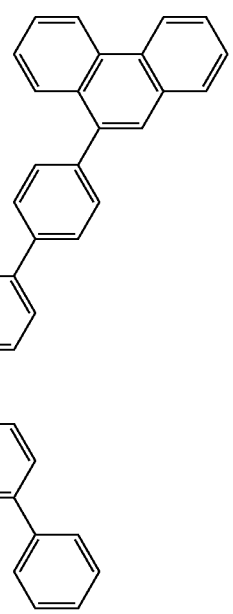

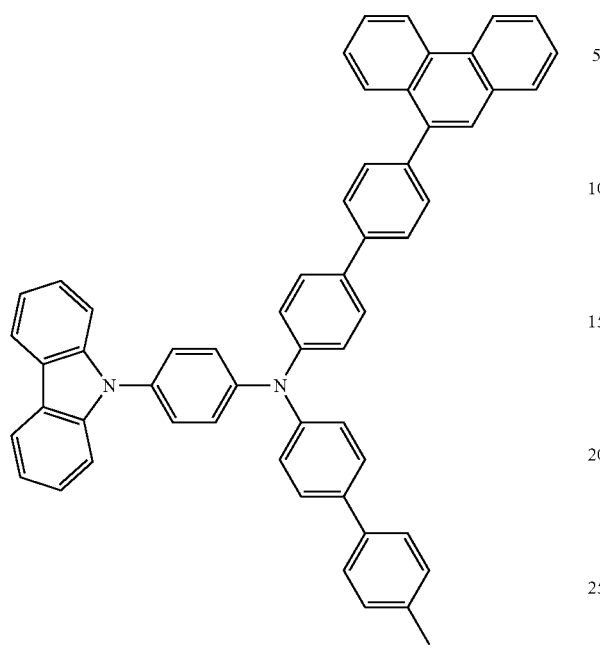
44
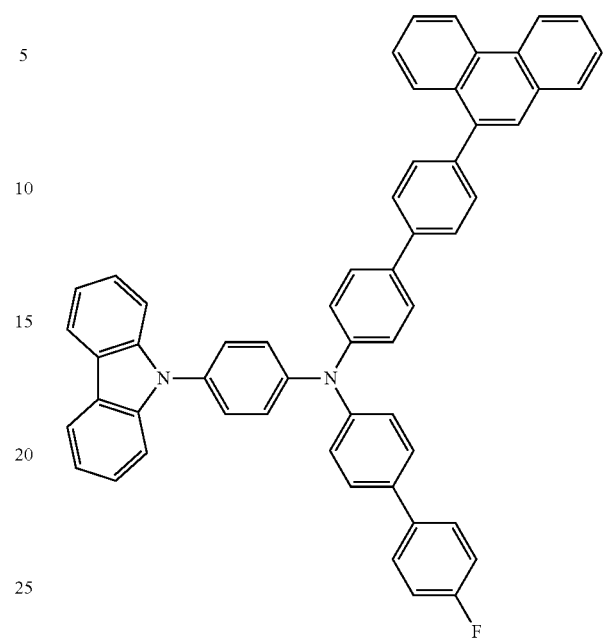
46
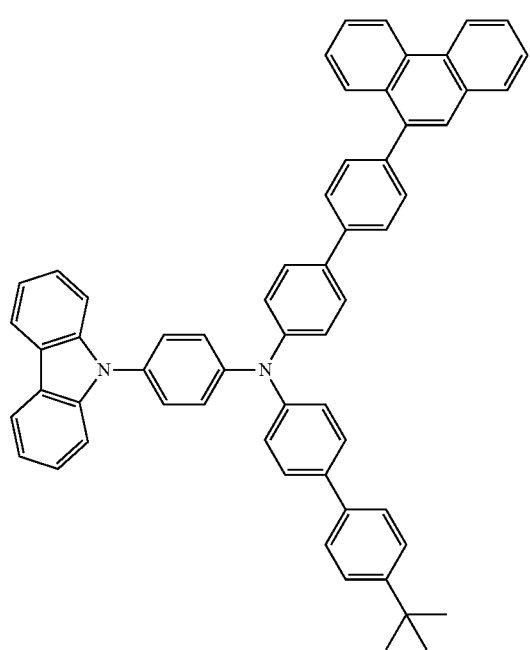
45
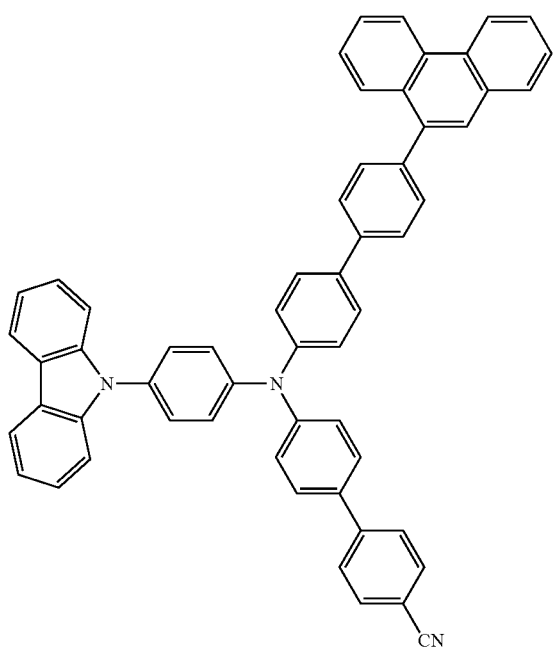
47

48
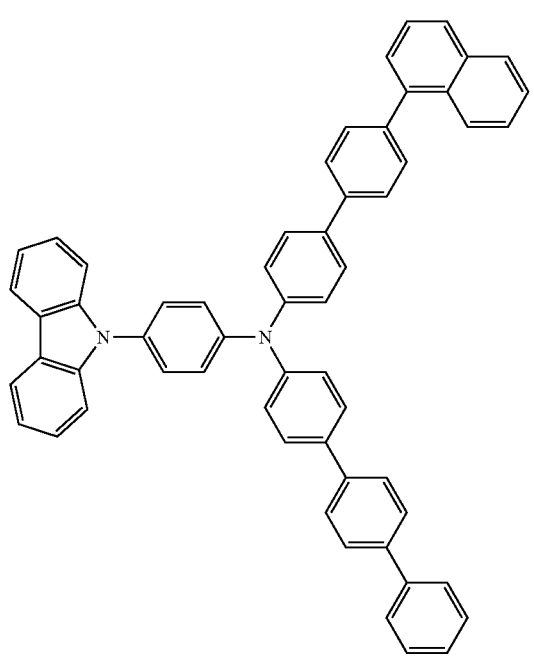
50
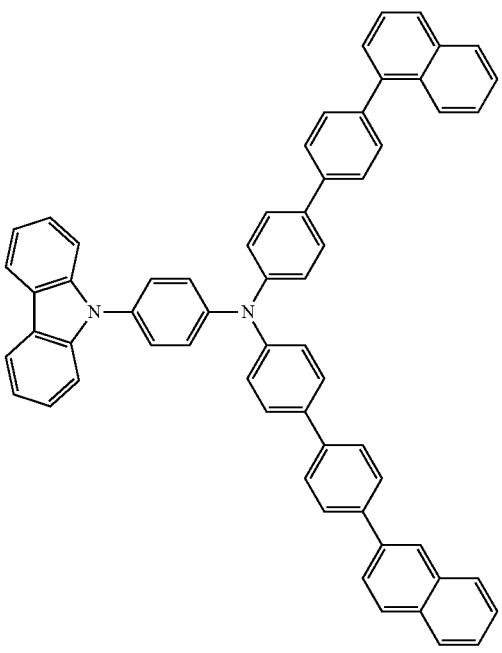
49
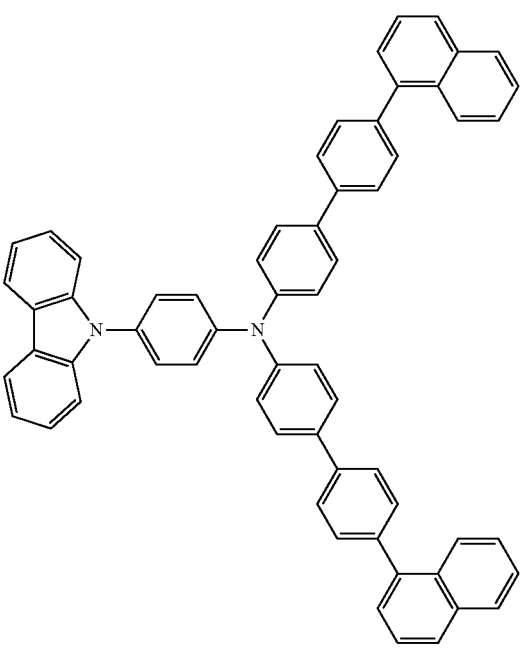
51
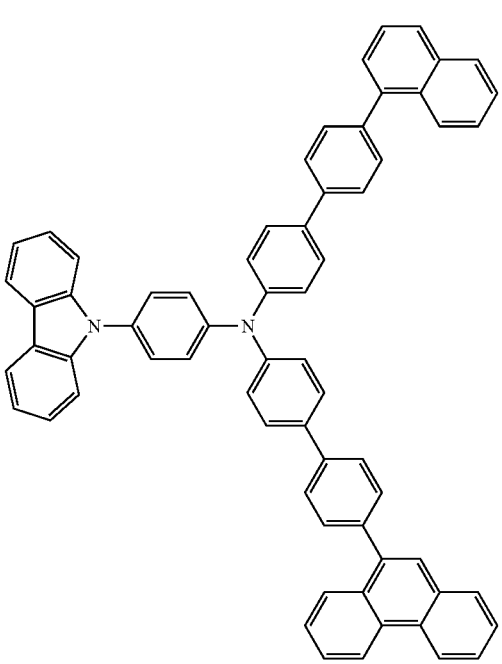

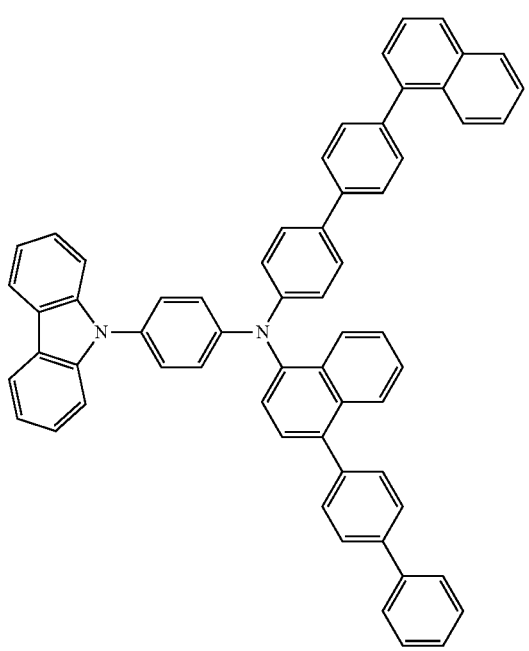
52
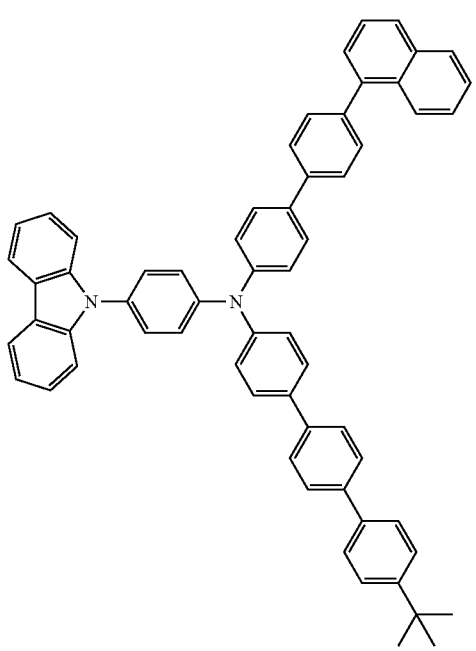
54
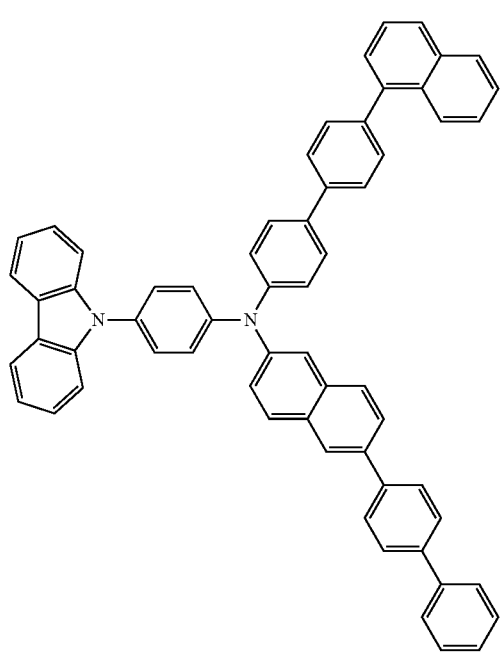
53
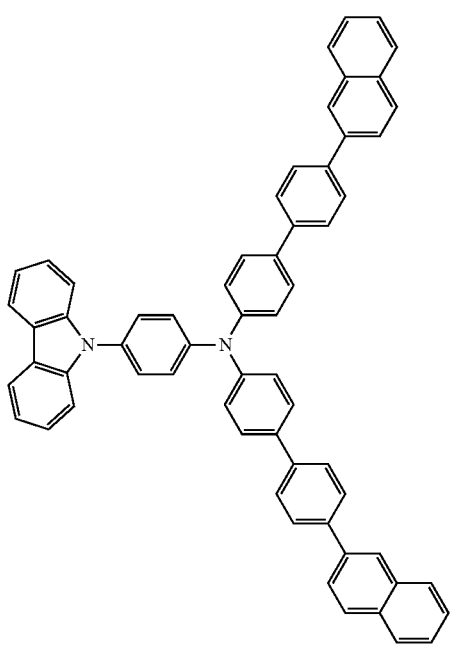
55

56
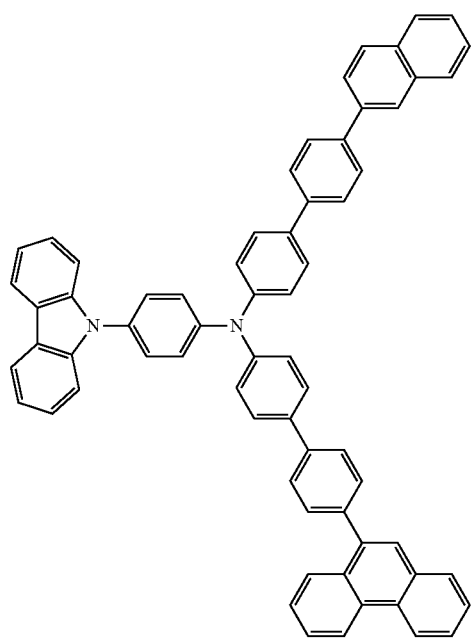
57
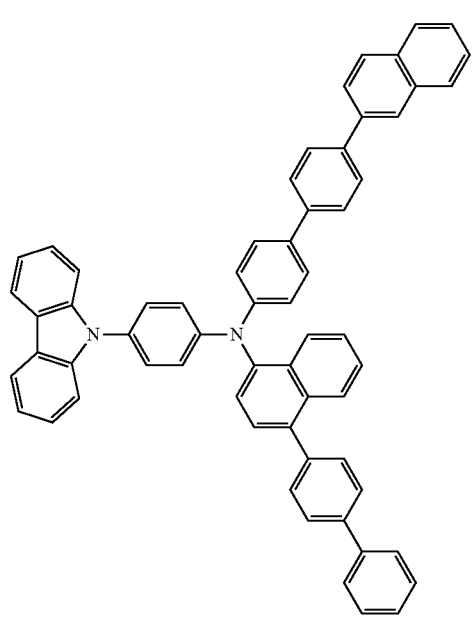
58
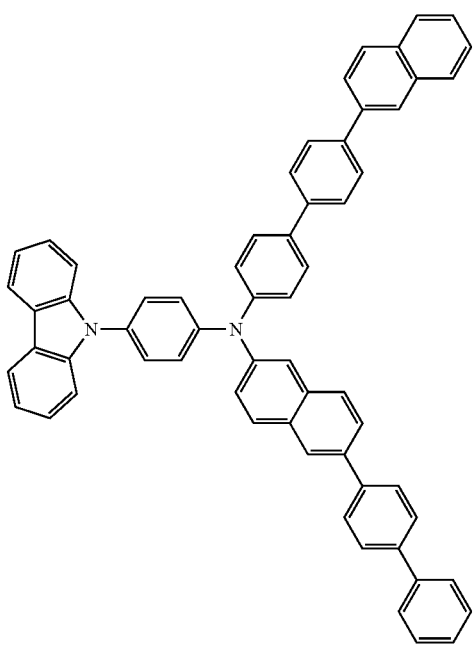
59
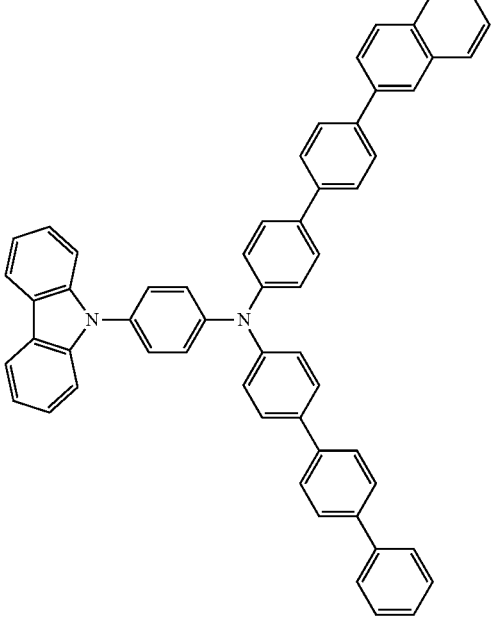

60
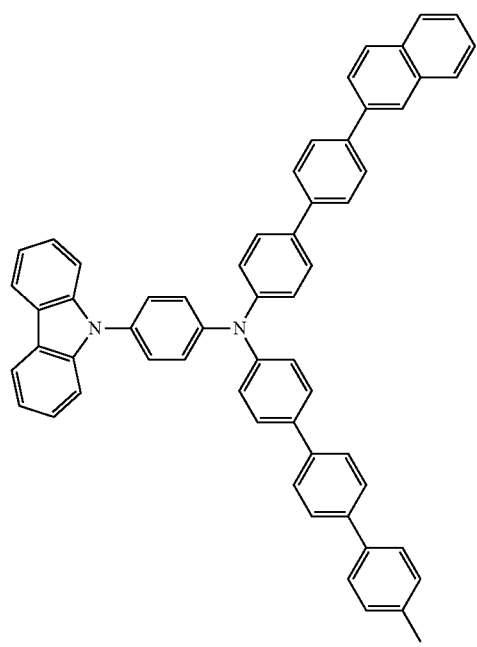
62
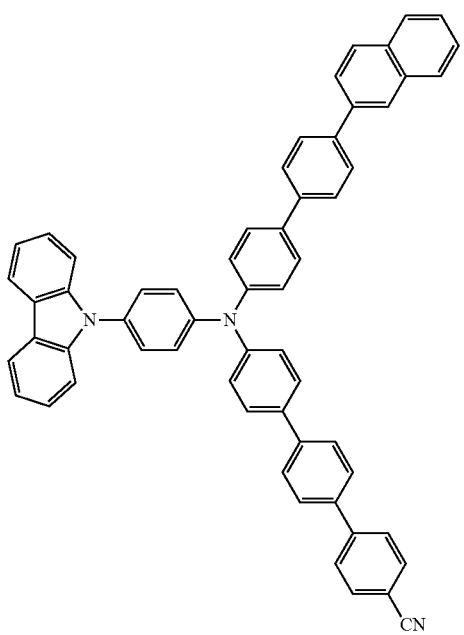
61
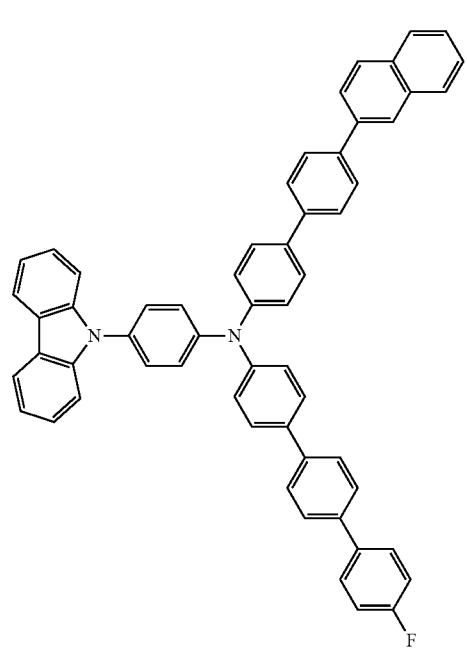
63
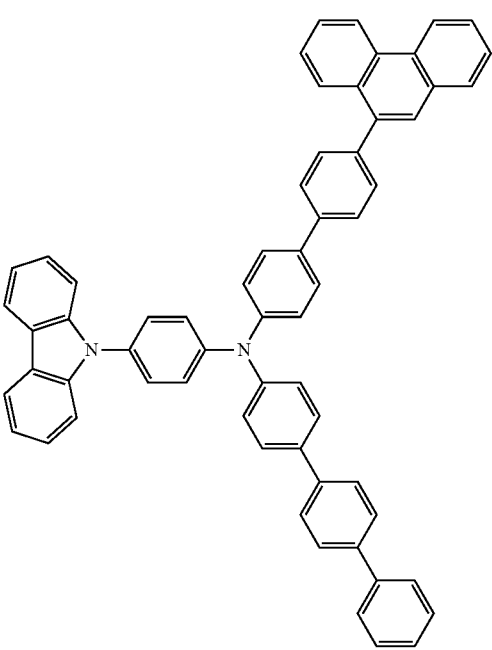

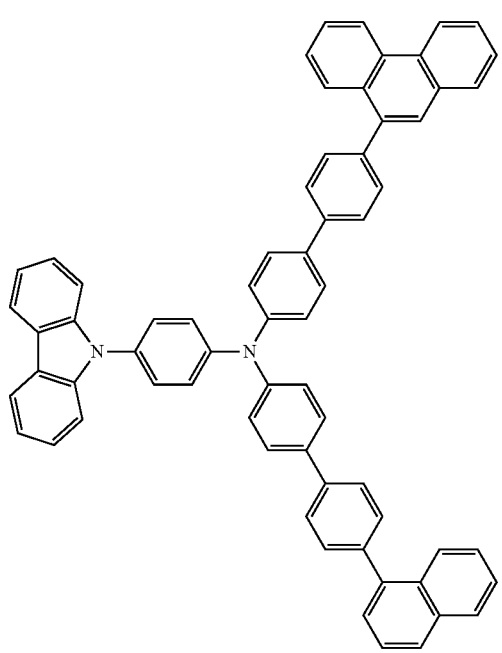
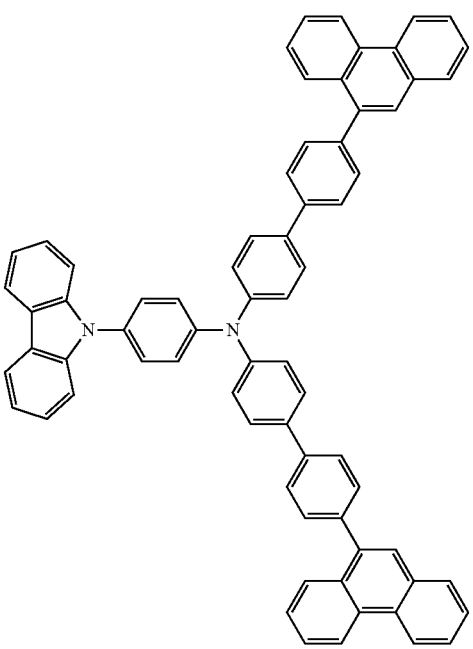
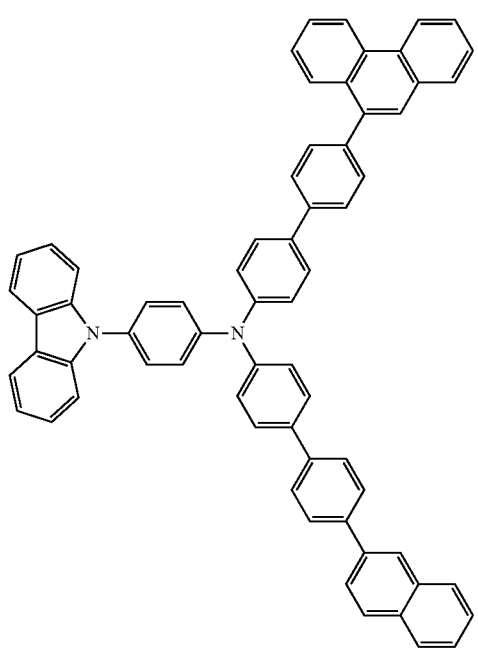
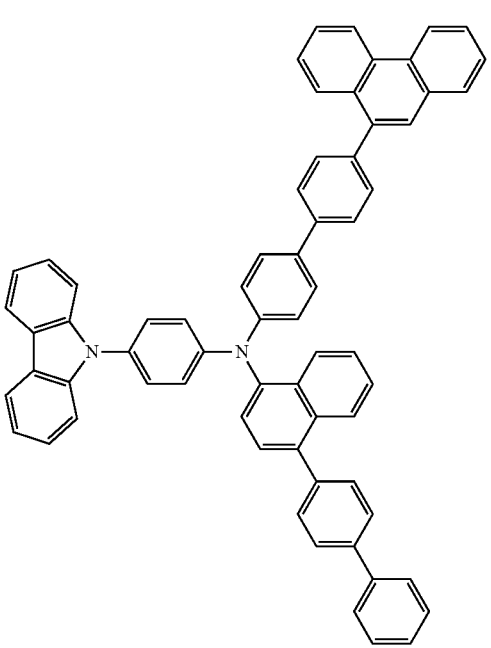

68
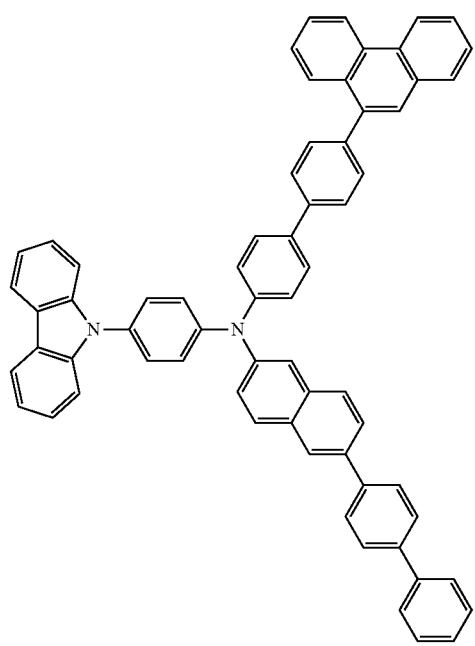
69
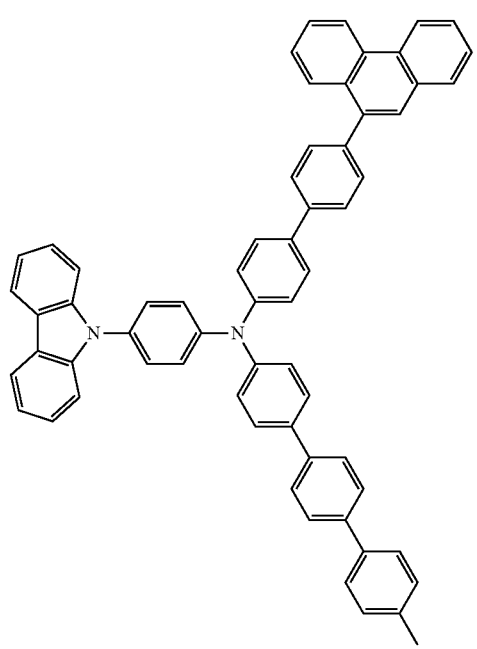
70
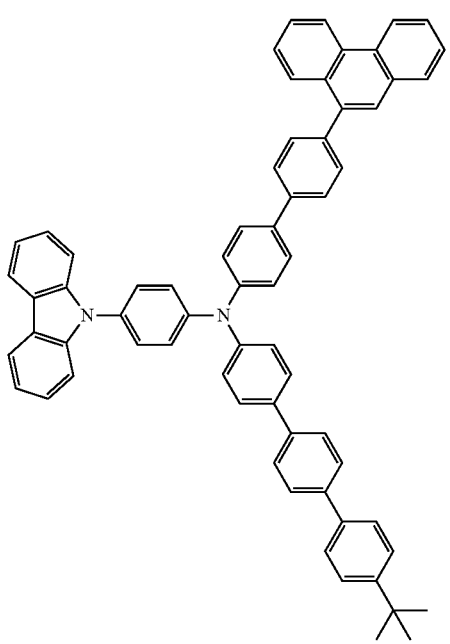
71
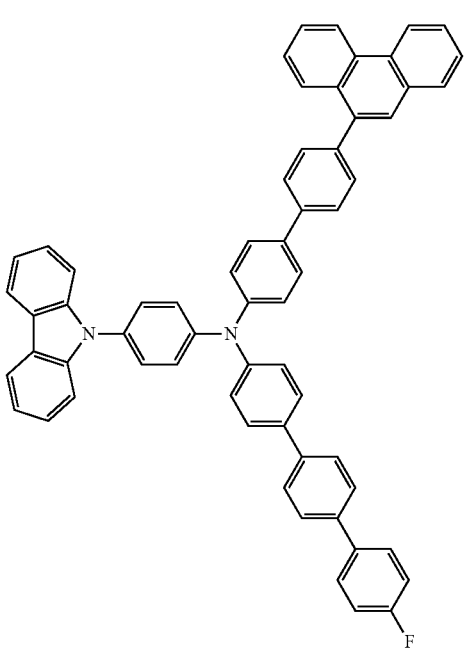

-continued
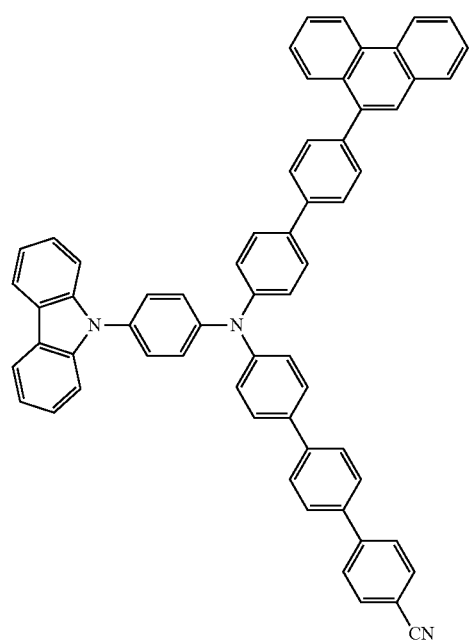
72
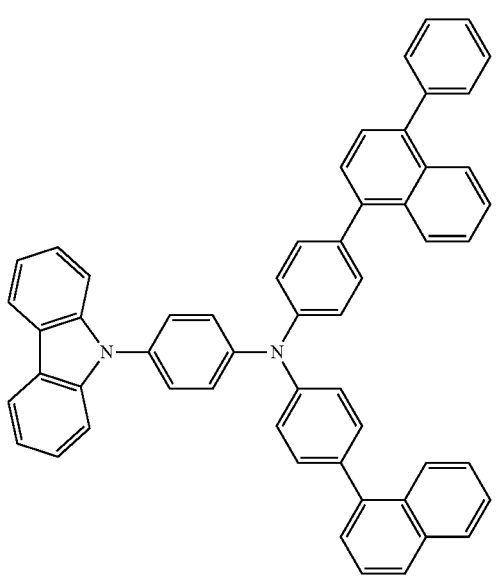
73
-continued
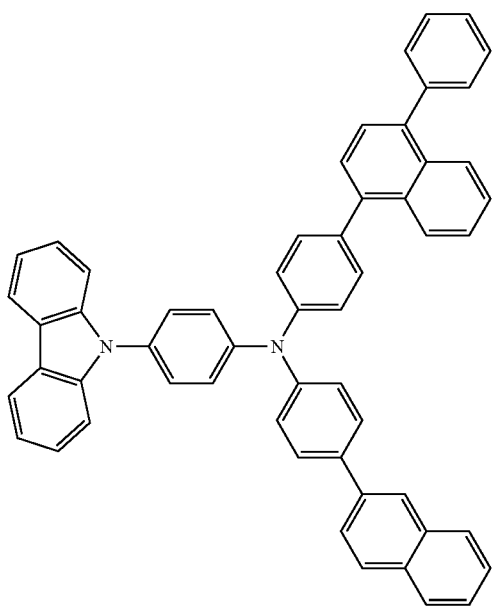
74
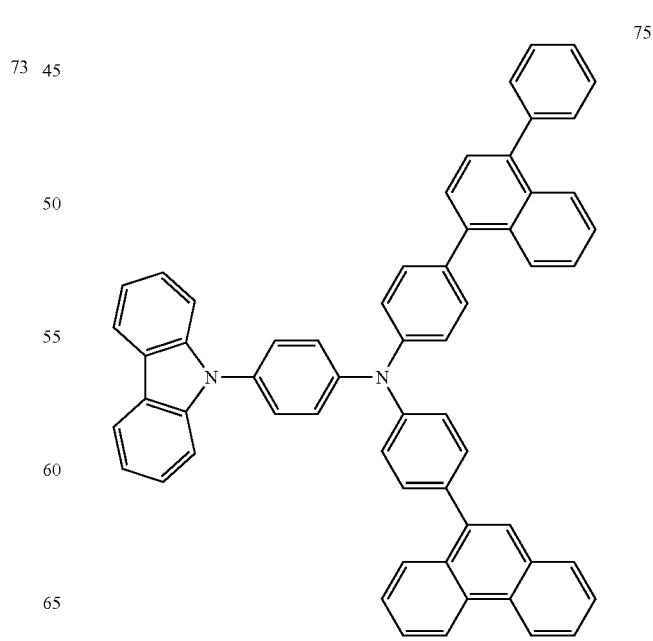
75

76
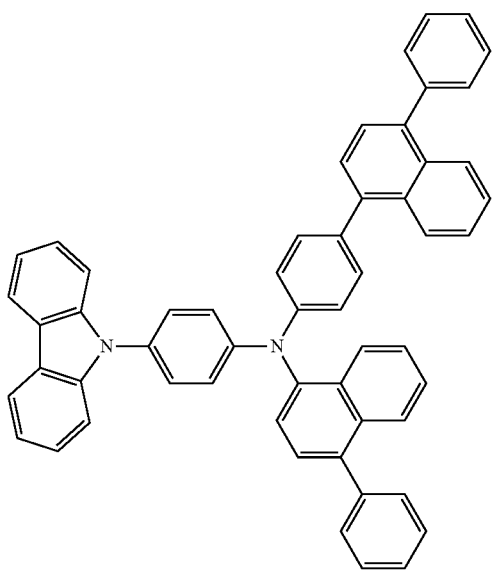
77
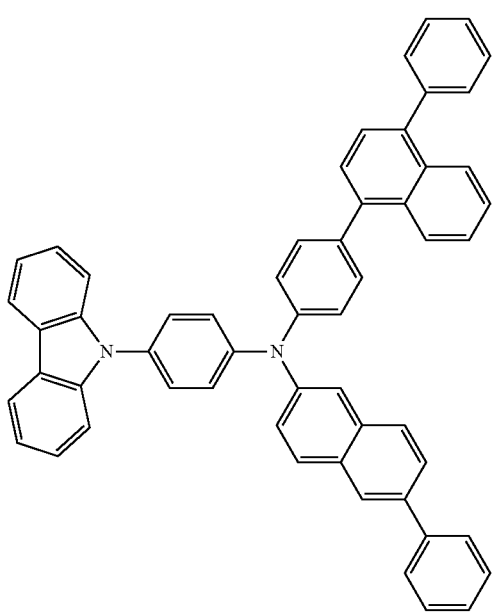
78
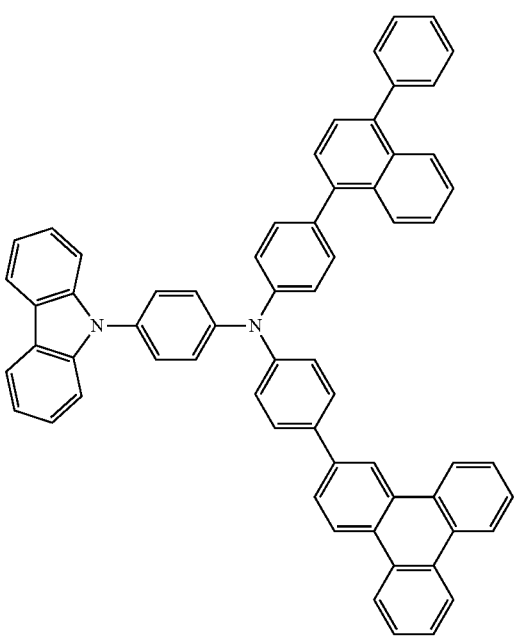
79

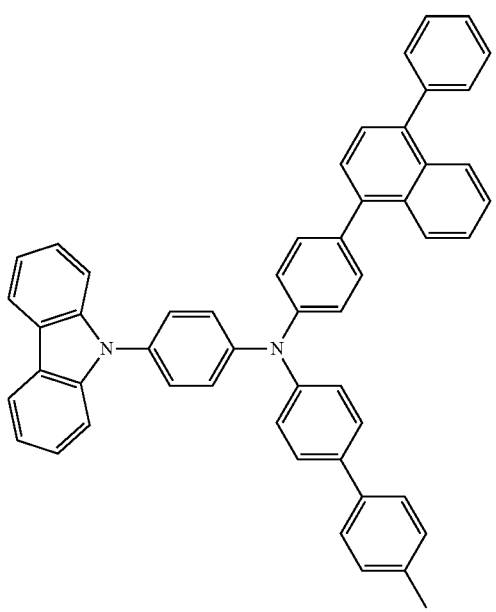
80
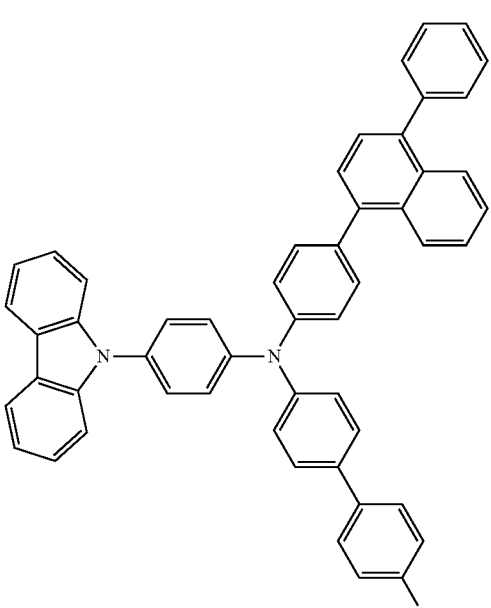
82
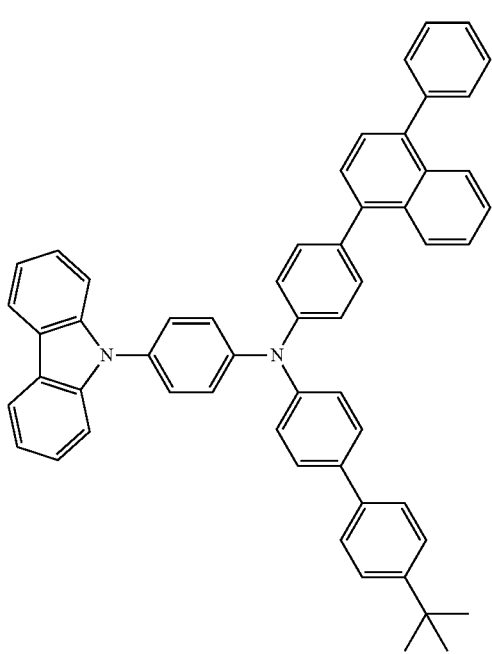
81
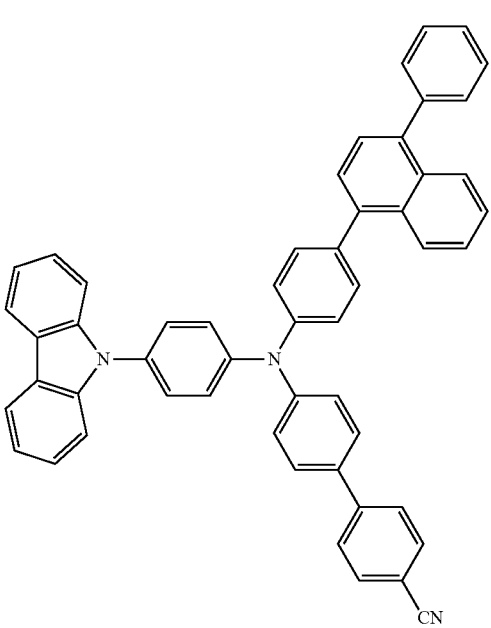
83

84
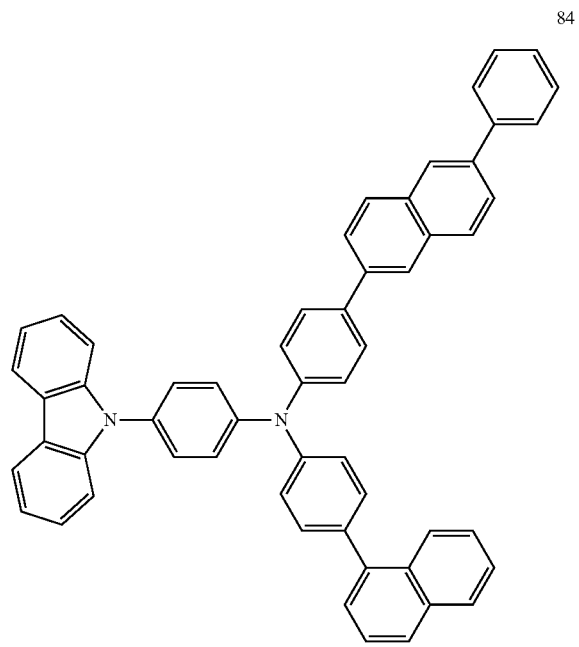
85
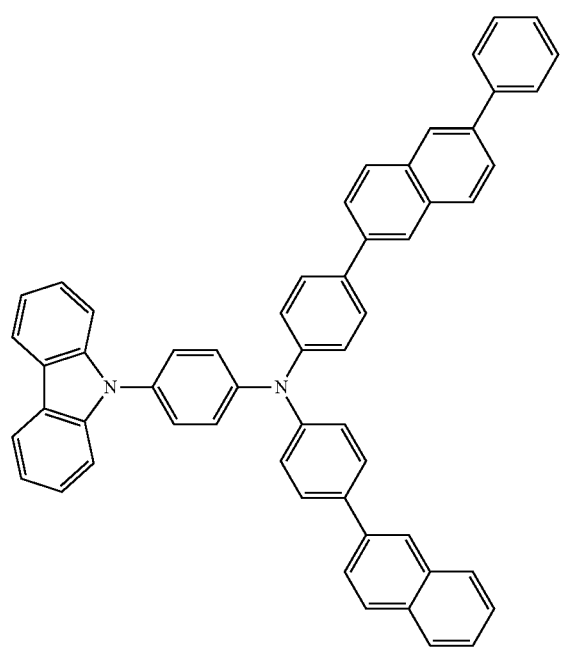
86
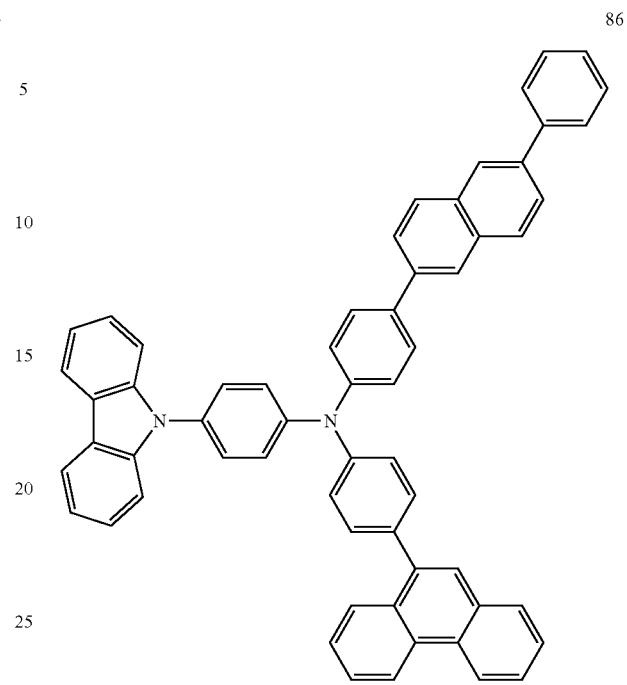
87
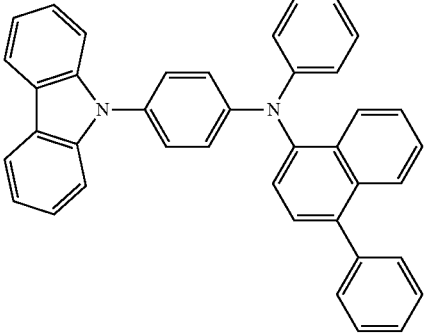

88
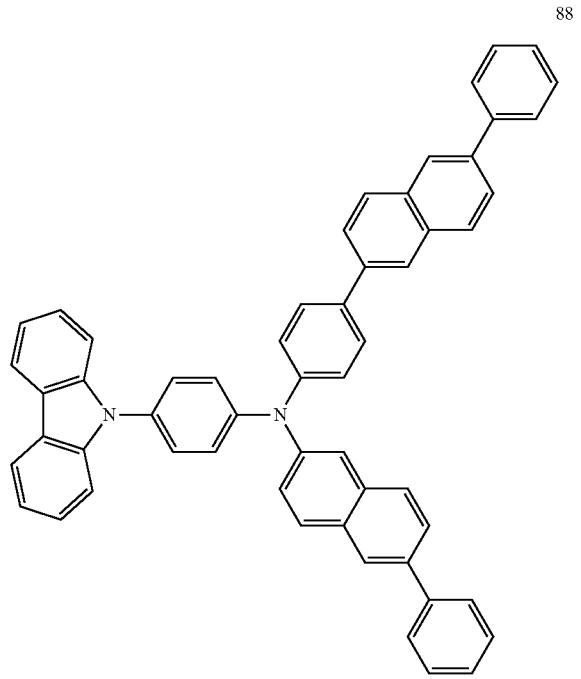
90
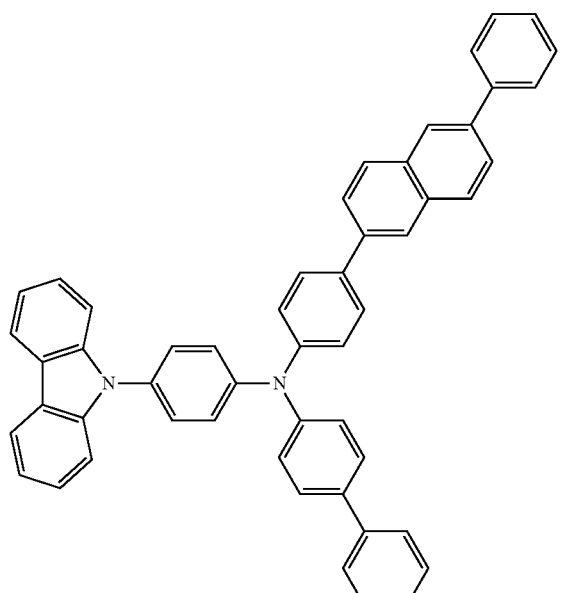
89
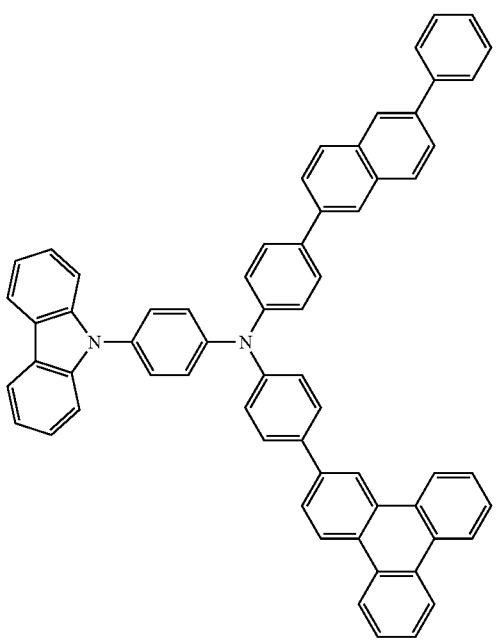
91
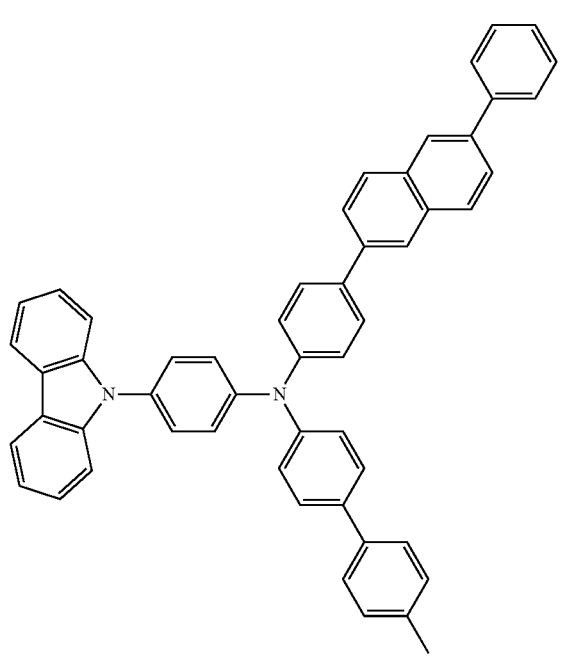

-continued
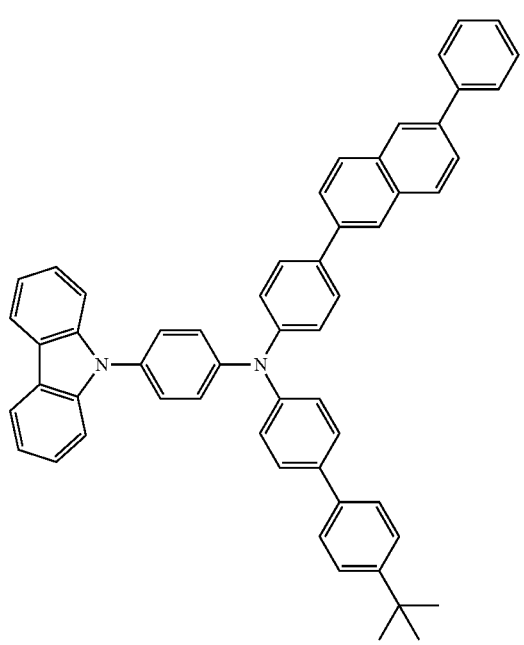
92
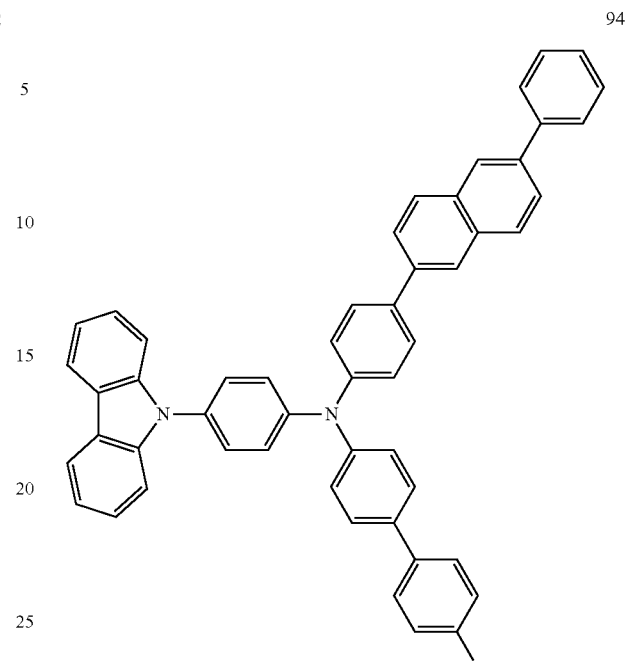
94
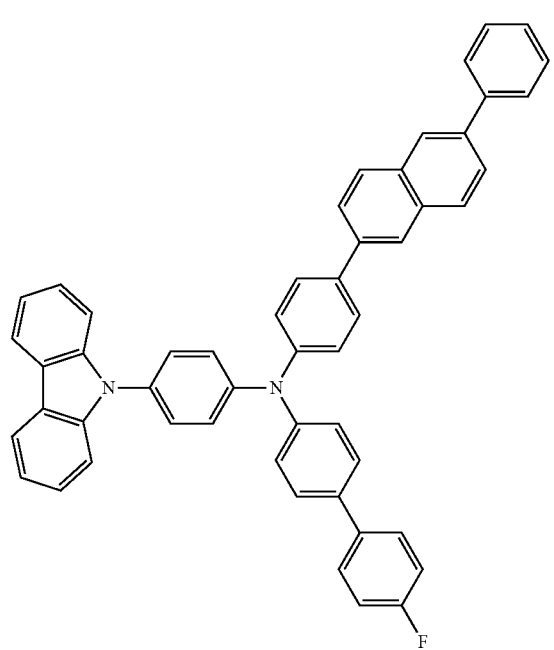
93
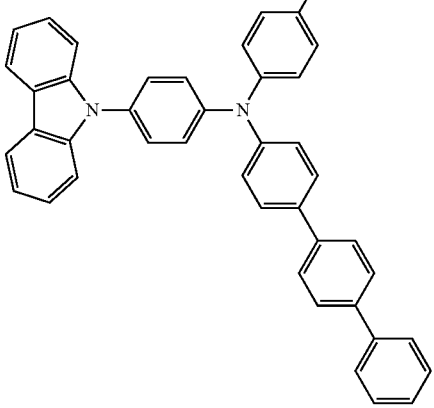
95

96
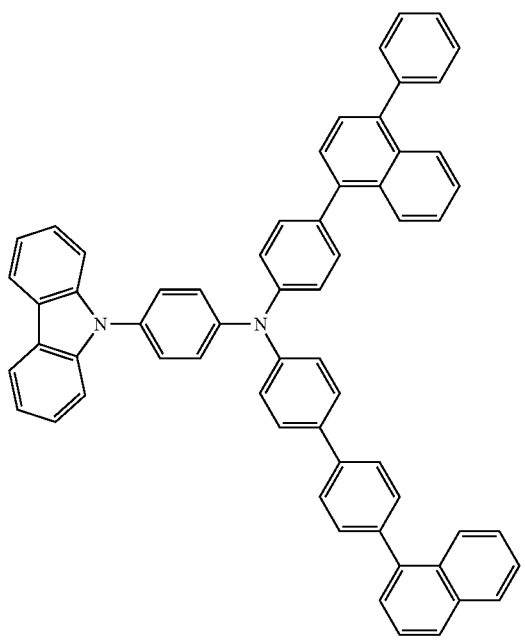
98
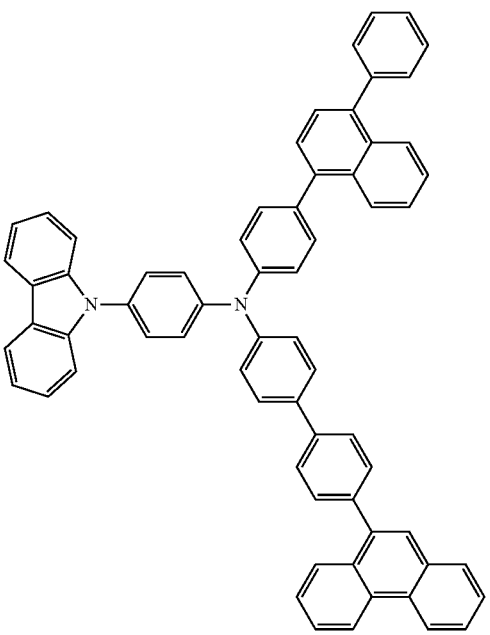
97
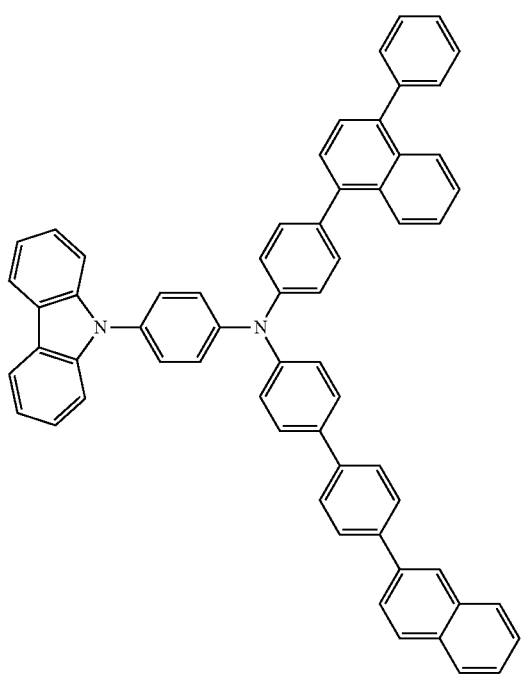
99
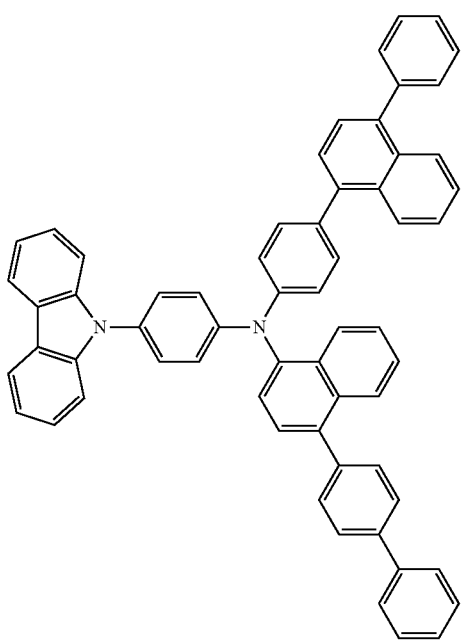

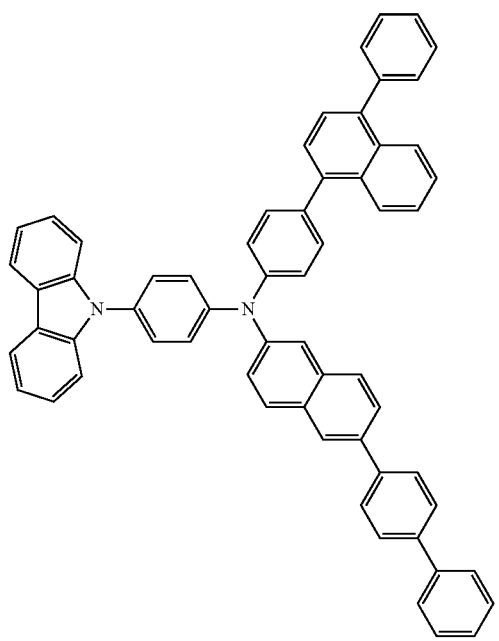
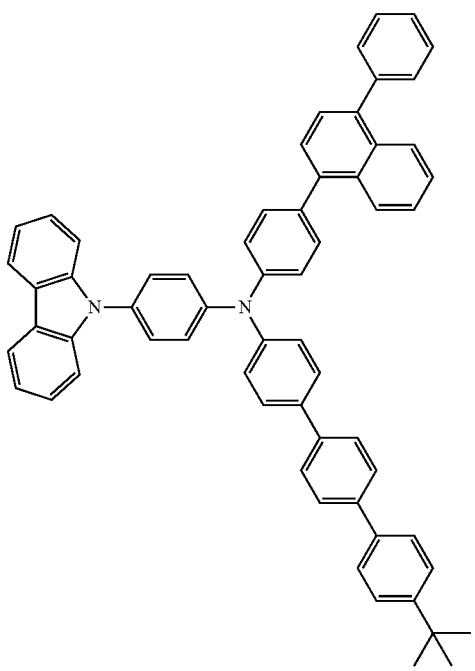
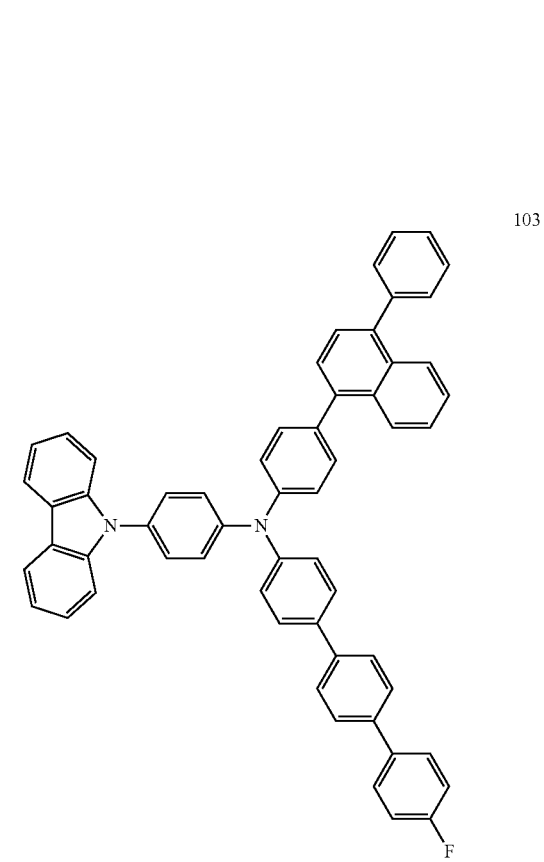

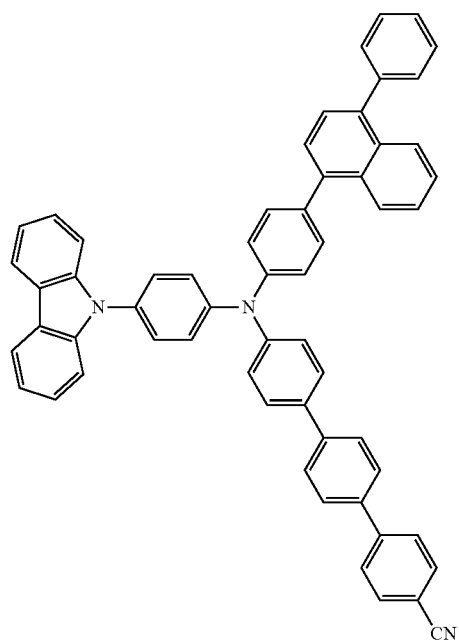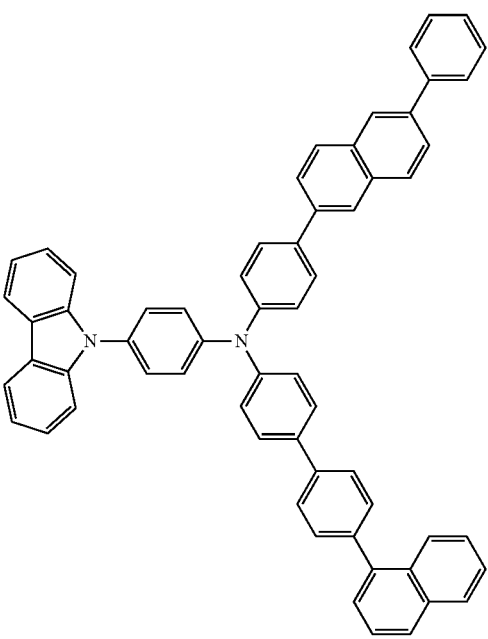

108
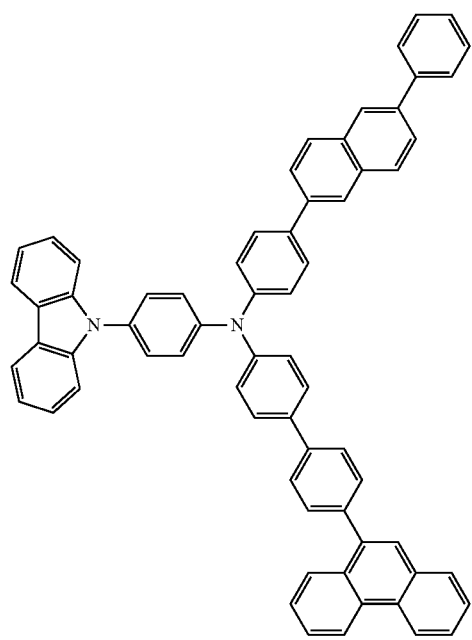
110
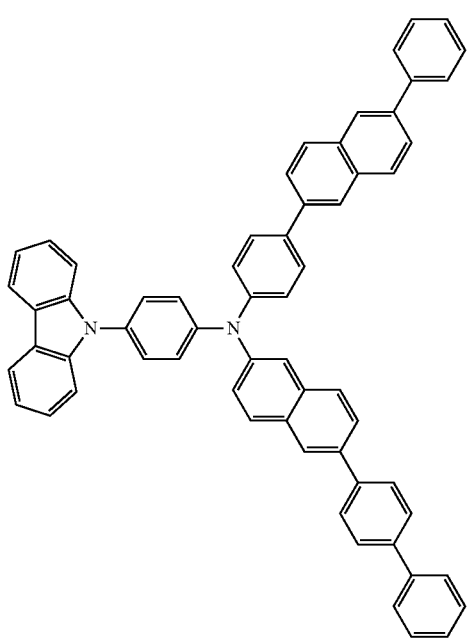
109
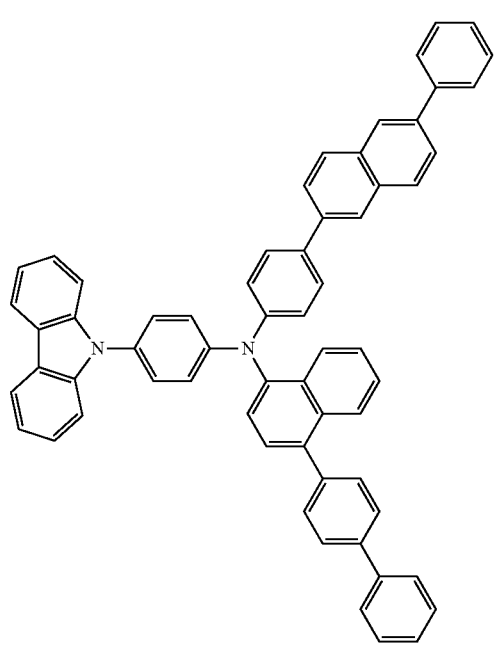
111
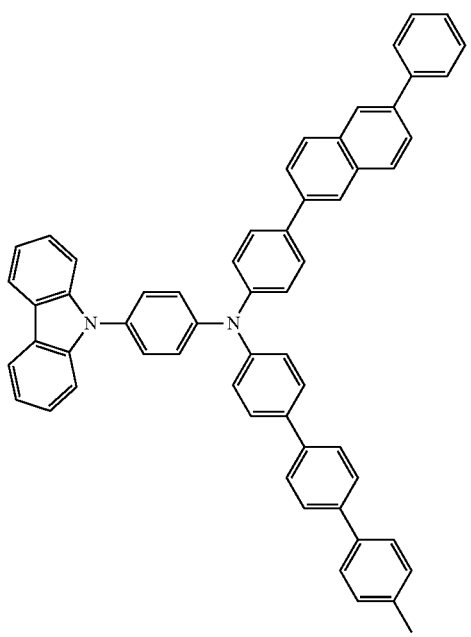

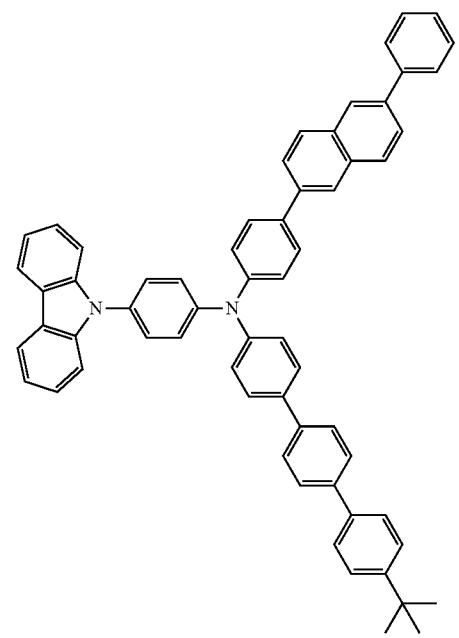
112
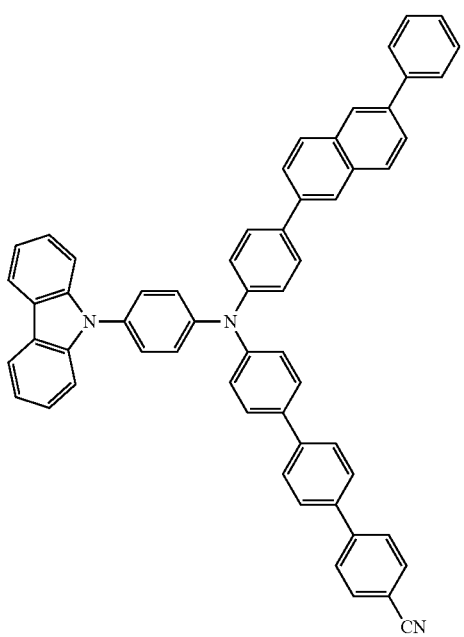
114
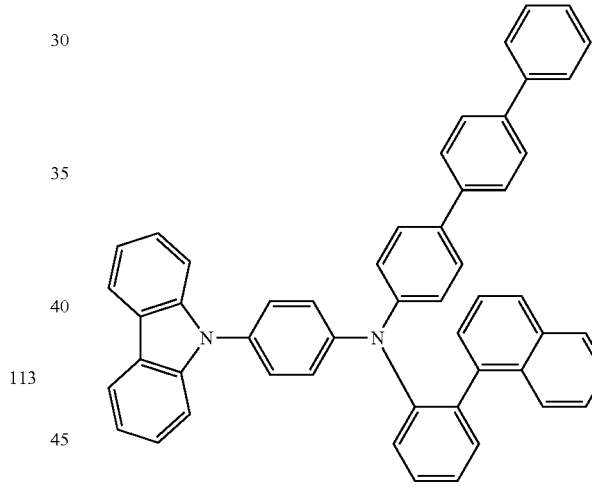
115
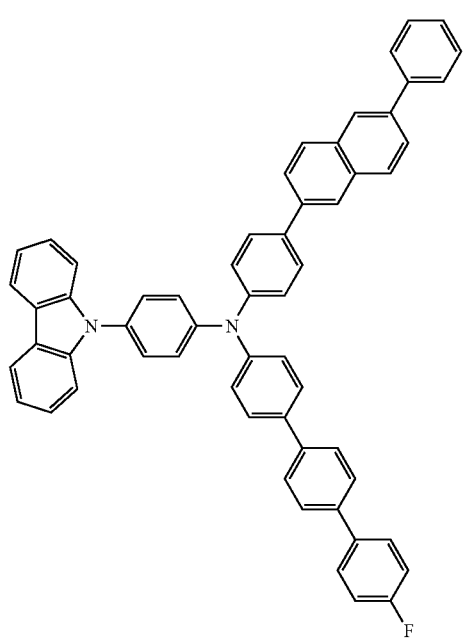
113
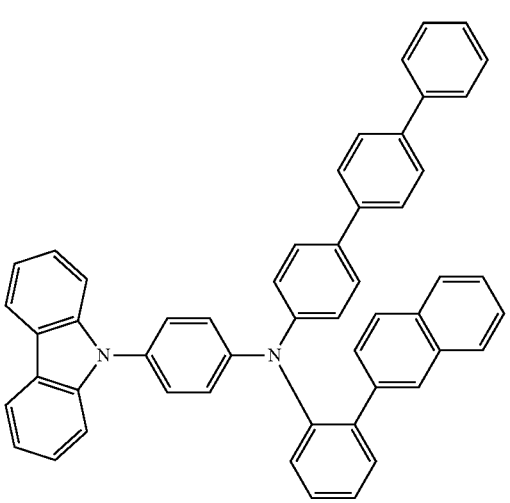
116

117
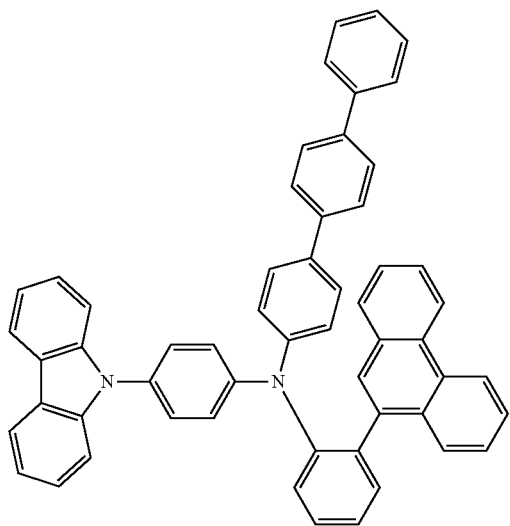
118
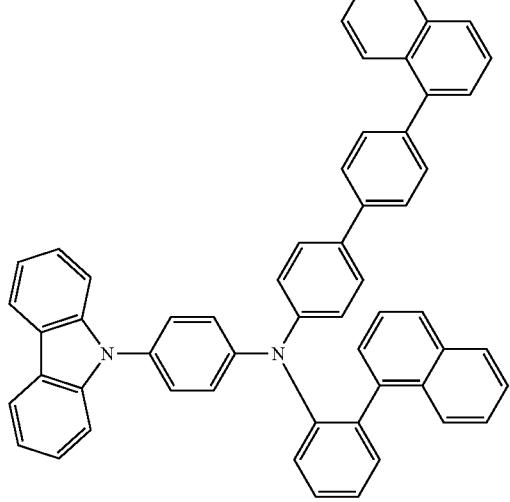
119
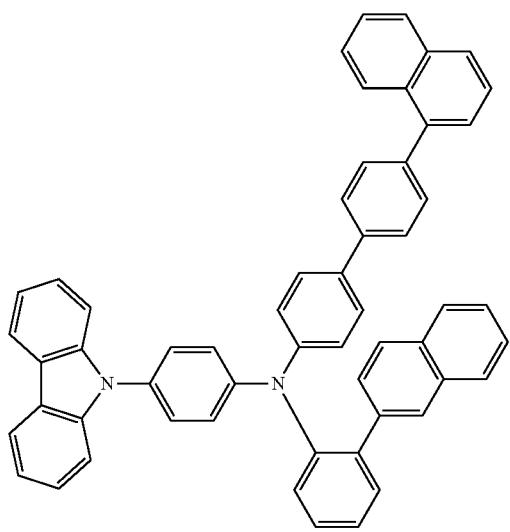
120
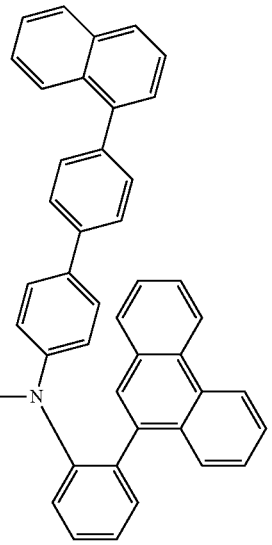
121
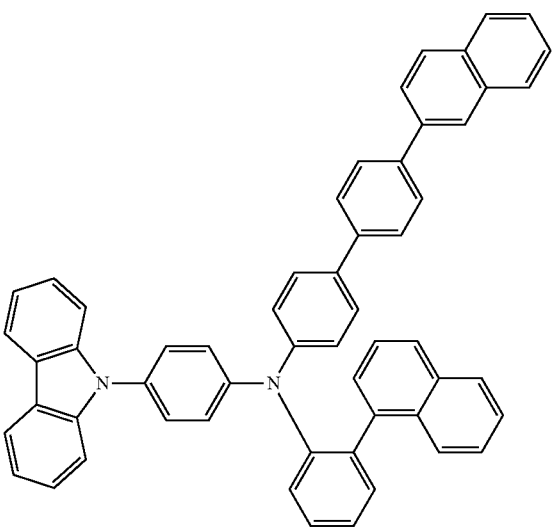
122
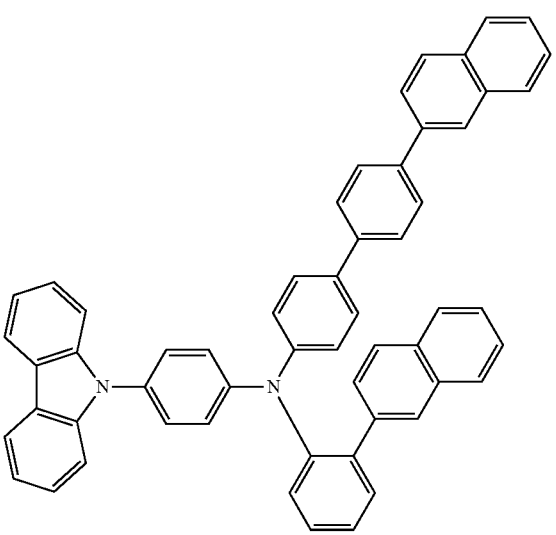

123
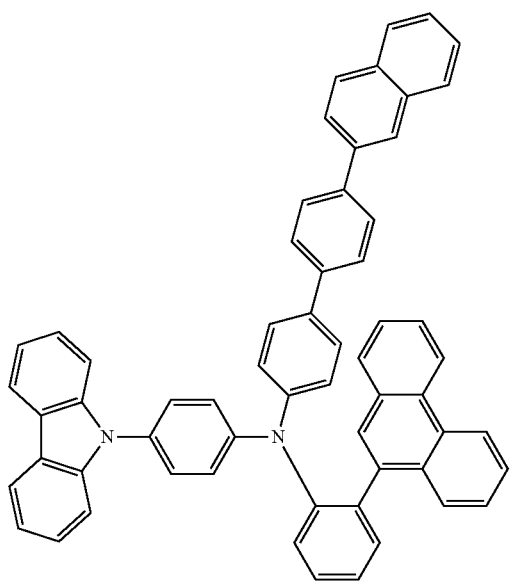
126
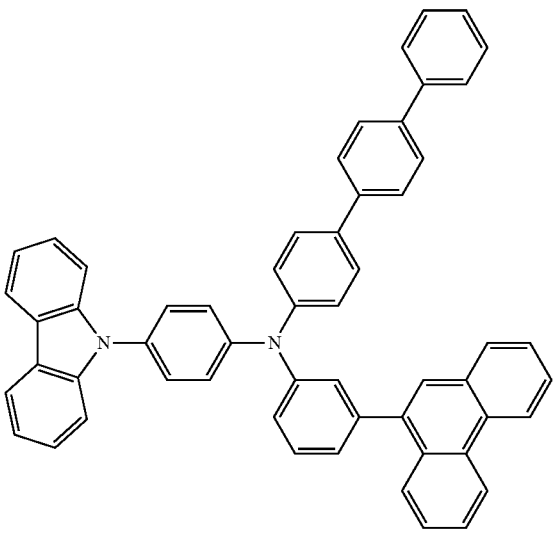
124
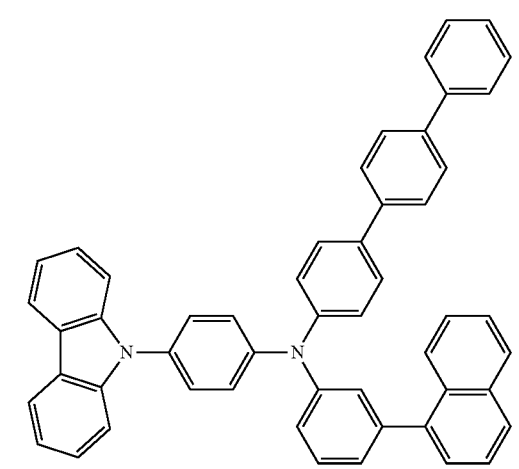
127
125
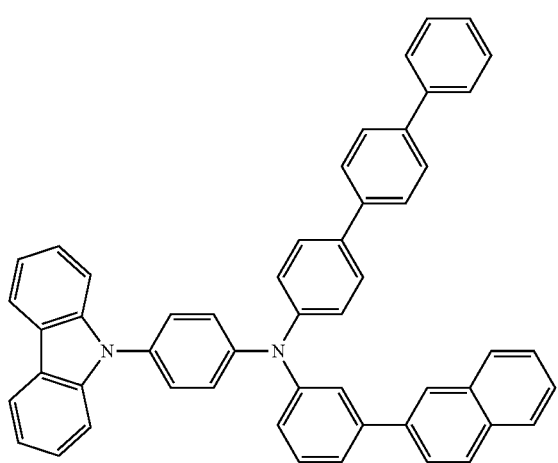
128
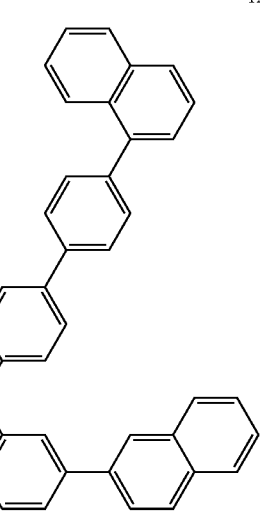

129
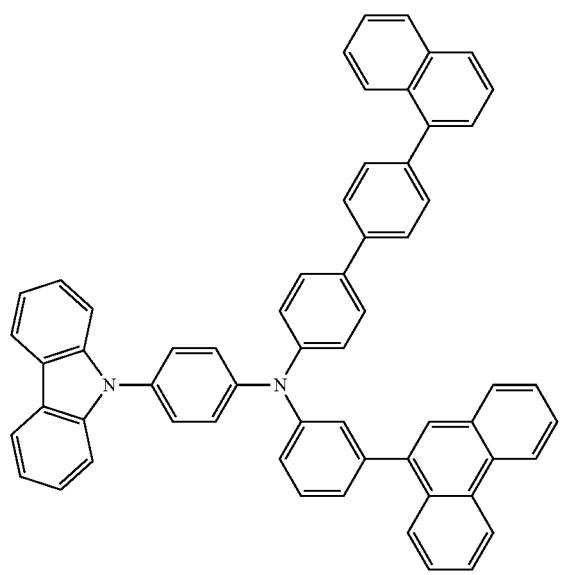
130
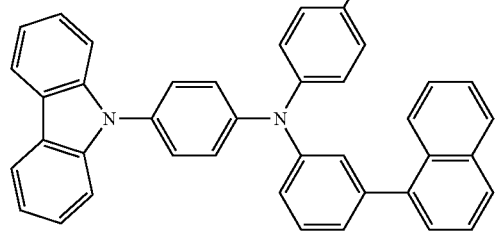
131
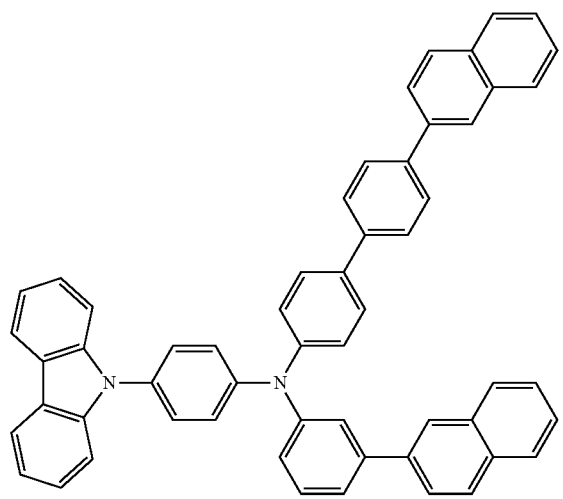
132
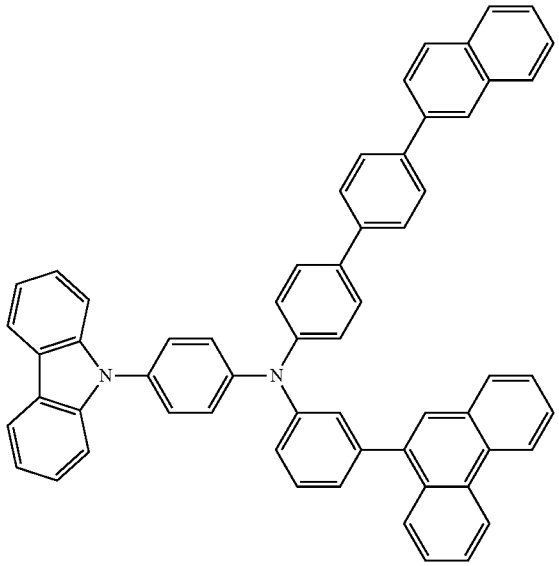
133
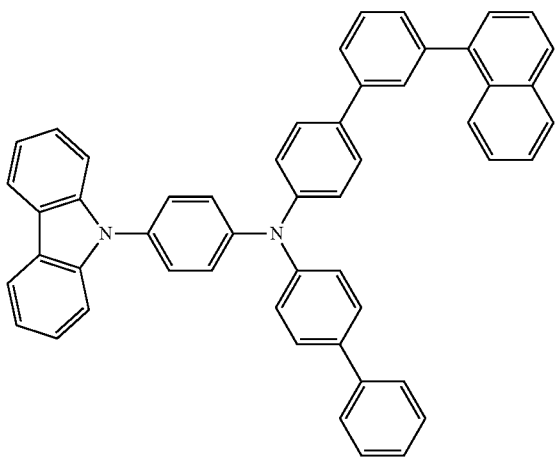
134
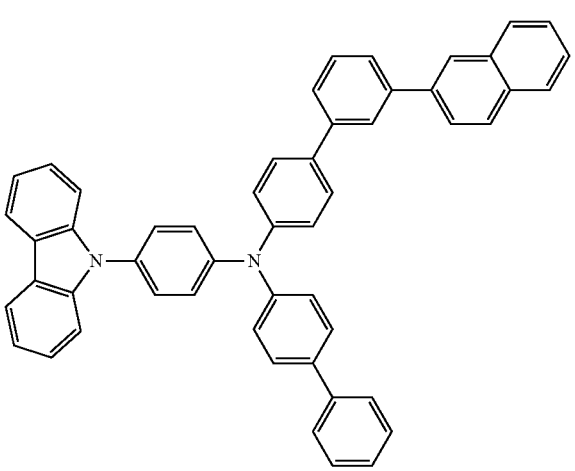

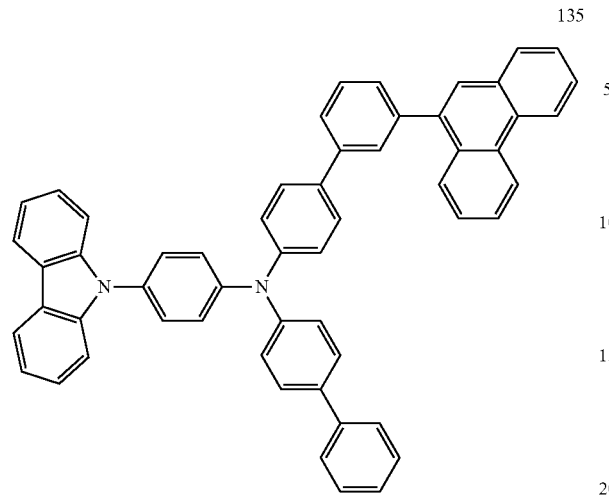
135
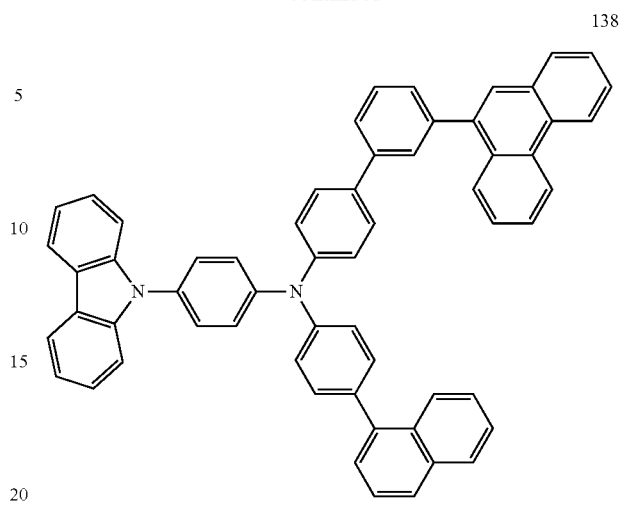
138
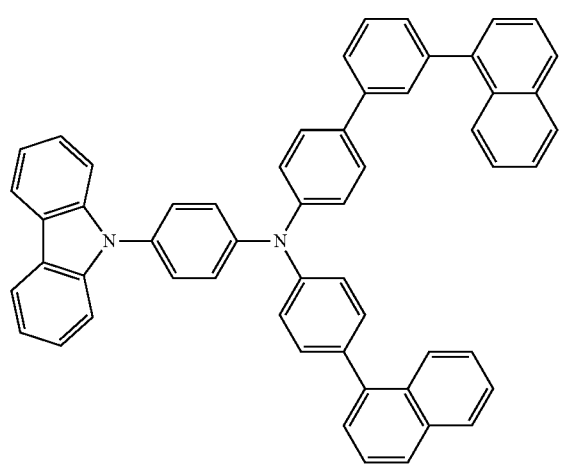
136
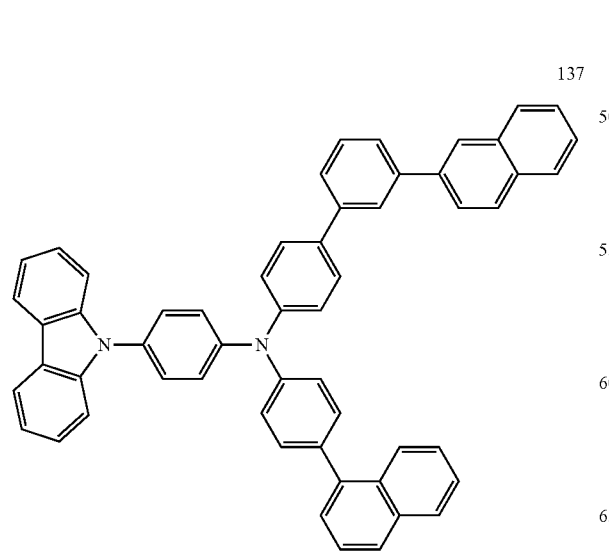
137
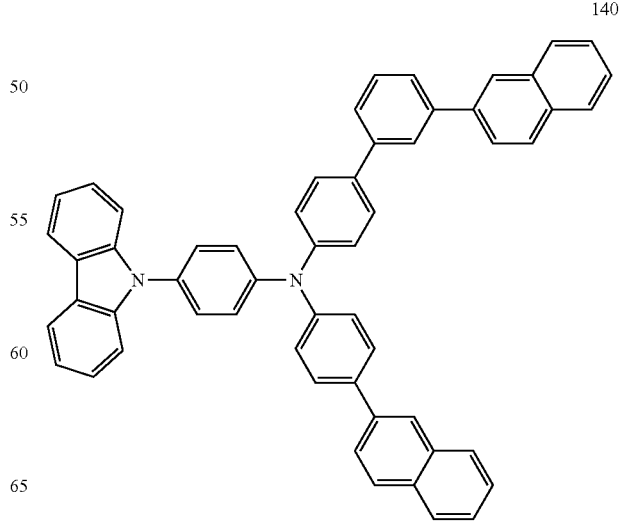
139
140

141
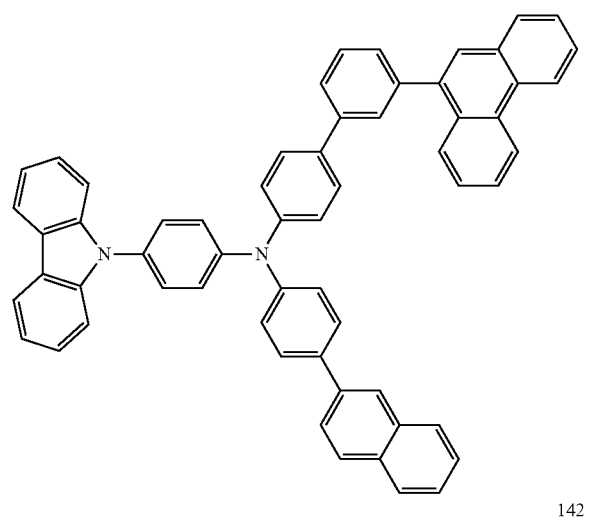
142
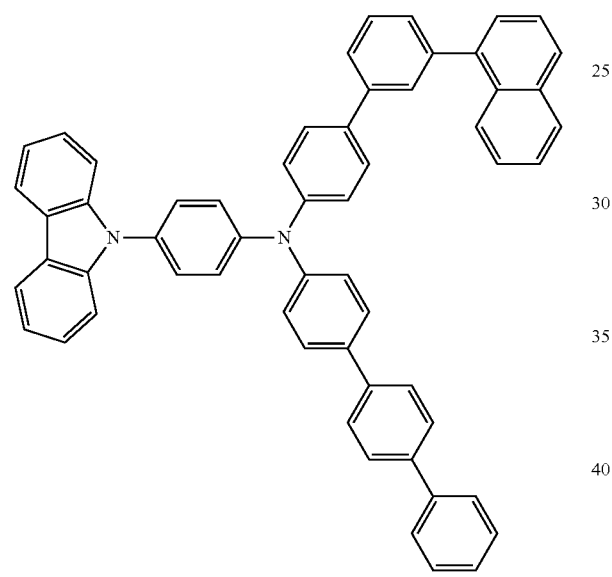
143
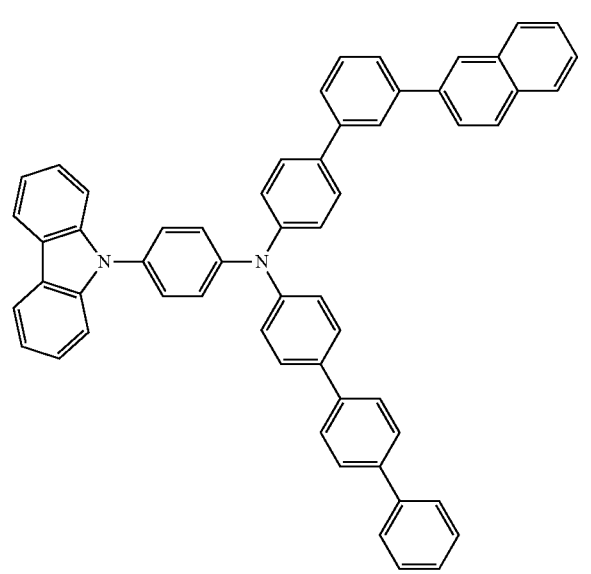
144
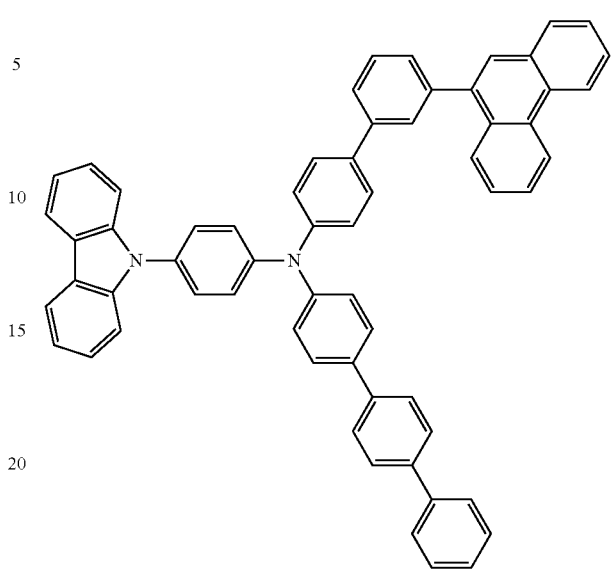
145
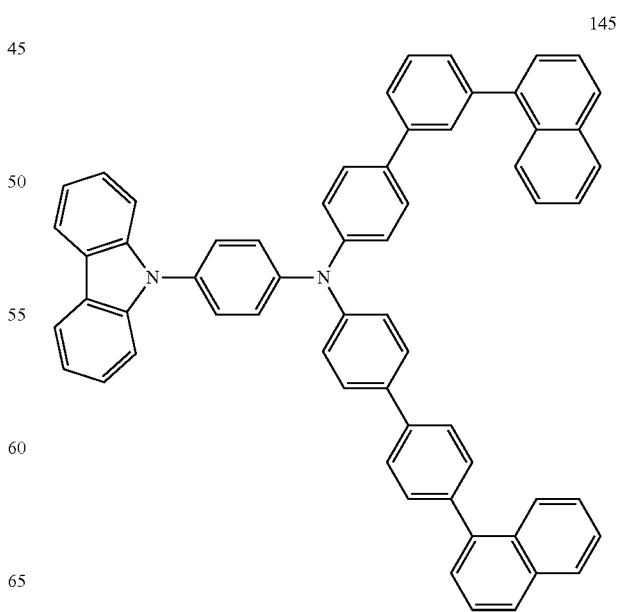

-continued
146
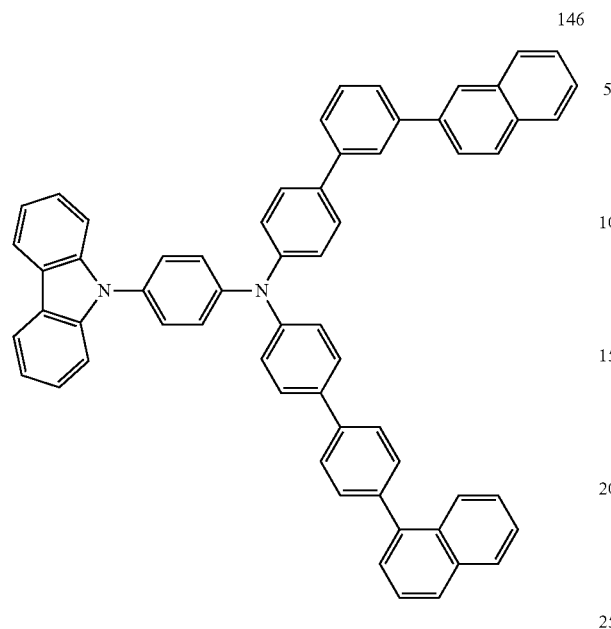
147
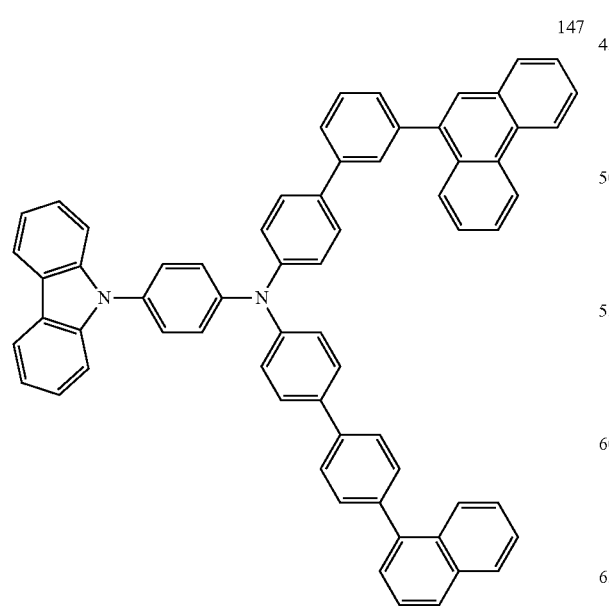
148
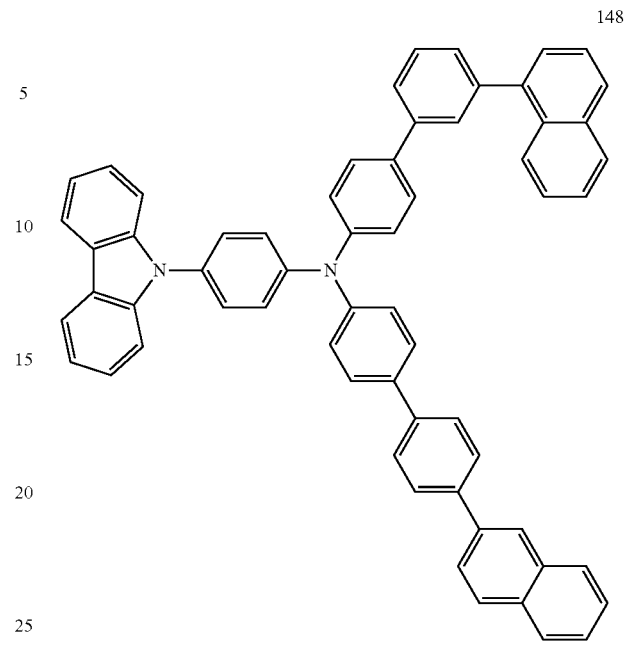
149
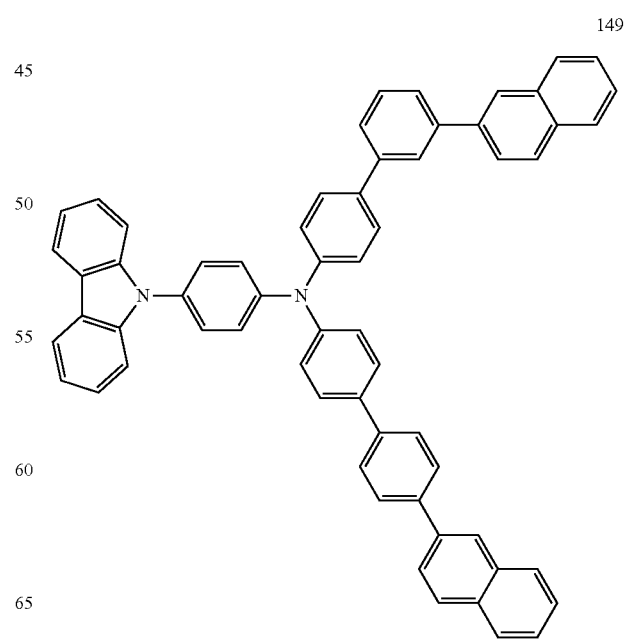

-continued

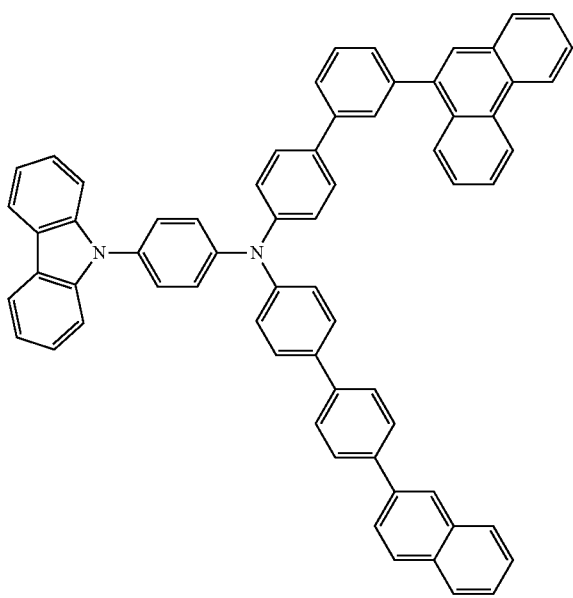

150

The organic electroluminescent device may include an organic layer containing a compound represented by Chemical Formula 1, as described above.

Specifically, the organic layer may include a hole transport layer or a hole transport auxiliary layer and may contain a compound represented by Chemical Formula 1.

The organic layer may include at least one selected from the group consisting of a hole injection layer, a hole transport layer, a hole transport auxiliary layer, an electron transport auxiliary layer, an electron transport layer and an electron injection layer, in addition to an organic layer containing a compound represented by Chemical Formula 1.

In one embodiment, the organic electroluminescent device may include a hole transport auxiliary layer containing a compound represented by Chemical Formula 1.

FIG. 1 illustrates an organic electroluminescent device 10 according to one embodiment of the present disclosure. In FIG. 1, the organic electroluminescent device 10 may sequentially include an anode 1, a hole injection layer 2, a hole transport layer 3, a hole transport auxiliary layer 7, a light emission layer 4, an electron transport layer 5, and a cathode 6.

The anode 1 provides holes into the light emission layer 4. The anode 1 may include a conductive material having a high work function to easily provide holes. When the organic electroluminescent device 10 is applied to as a bottom emission type organic light emitting display, the anode 1 may be embodied as a transparent electrode made of a transparent conductive material. When the organic electroluminescent device is applied to as a top emission type organic light emitting display, the anode 1 may have a multilayer structure in which a transparent electrode layer made of a transparent conductive material and a reflective layer are stacked vertically.

The cathode 6 provides electrons into the light emission layer 4. The cathode 6 may include a conductive material having a low work function to easily provide electrons. When the organic electroluminescent device is applied to as a bottom emission type organic light emitting display, the cathode 6 may be embodied as a reflective electrode made of a metal. When the organic electroluminescent device is applied to as a top emission type organic light emitting display, the cathode 6 may be embodied as a transmissive electrode made of a thin metal.

The light emission layer 4 may emit red (R), green (G), or blue (B) light, and may be made of a phosphor or a fluorescent material.

When the light emission layer 4 emits red light, the light emission layer 4 may contain a host material including CBP (carbazole biphenyl) or mCP (1,3-bis(carbazol-9-yl)). The light emission layer 4 may contain a phosphor dopant including one selected from the group consisting of PIQIr (acac) (bis(1-phenylisoquinoline)acetylacetonate iridium), PQIr(acac) (bis(1-phenylquinoline)acetylacetonate iridium), PQIr (tris(1-phenylquinoline)iridium), PtOEP (octaethylporphyrin platinum), and combinations thereof. Alternatively, the light emission layer 4 may contain a fluorescent material including PBD:Eu(DBM)3(Phen) or perylene. However, the present disclosure is not limited thereto.

When the light emission layer 4 emits green light, the light emission layer 4 may contain a host material including CBP or mCP. The light emission layer 4 may contain a phosphor including a dopant material including Ir(ppy)3 (fac tris (2-phenylpyridine) iridium). Alternatively, the light emission layer 4 may contain a fluorescent material including Alq3 (tris (8-hydroxyquinolino) aluminum). However, the present disclosure is not limited thereto.

When the light emission layer 4 emits blue light, the light emission layer 4 may contain a host material including CBP or mCP, and may contain a phosphor dopant including (4,6-F2ppy)2Irpic. Alternatively, the light emission layer 4 may contain a fluorescent material including one selected from the group consisting of spiro-DPVBi, spiro-6P, distilbenzene (DSB), distriarylene (DSA), PFO-based polymer and PPV-based polymer, and combinations thereof. Alternatively, the light emission layer 4 may contain a compound of Chemical Formula 1 as a blue fluorescent material. However, the present disclosure is not limited thereto.

The hole injection layer 2 may serve to facilitate the injection of holes. The hole injection layer 2 may include one or more selected from the group consisting of, for example, cupper phthalocyanine (CuPc), poly(3,4)-ethylenedioxythiophene (PEDOT), polyaniline (PANI), N,N-di-naphthyl-N,N'-diphenyl benzidine (NPD) and combinations thereof. However, the present disclosure is not limited thereto.

The hole transport layer 3 may contain a material electrochemically stabilized via cationization (i.e., loss of electrons) as a hole transport material. Alternatively, a material that produces a stable radical cation may be a hole transport material. The hole transport layer 3 may contain a compound represented by Chemical Formula 1. Detailed descriptions of the compound represented by Chemical Formula 1 are as described above.

The hole transport layer 3 may further contain an additional hole transport material.

The additional hole transport material may be a material containing an aromatic amine and this being easily to be cationized. For example, the additional hole transport material may include one selected from the group consisting of NPD (N,N-dinaphthyl-N,N'-diphenylbenzidine), TPD (N,N'-bis-(3-methylphenyl)-N,N'-bis-(phenyl)-benzidine), Spiro-TAD (2,2',7,7'-tetrakis(N,N-dimethylamino)-9,9-spirofluorene), MTDATA (4,4',4-Tris(N-3-methylphenyl-N-phenylamino)-triphenylamine), and combinations thereof. However, the present disclosure is not limited thereto.

The hole transport auxiliary layer 7 may contain a compound represented by Chemical Formula 1. Detailed descriptions of the compound represented by Chemical Formula 1 are as described above.

The hole transport auxiliary layer 7 may further contain an additional hole transport auxiliary material other than the compound represented by Chemical Formula 1.

The additional hole transport auxiliary material may include one selected from the group consisting of TCTA (tris[4-(diethylamino)phenyl]amine), N-(biphenyl-4-yl)-9,9-dimethyl-N-(4-(9-phenyl-9H-carbazol-3-yl)phenyl)-9H-fluoren-2-amine, tri-p-tolylamine, TAPC (1,1-bis(4-(N,N'-di(ptolyl)amino)phenyl)cyclohexane), MTDATA, mCP, mCBP, CuPC, DNTPD (N,N'-bis[4-[bis(3-methylphenyl)amino]phenyl]-N,N'-diphenyl-[1,1'-biphenyl]-4,4'-diamine), TDAPB, and combinations thereof. However, the present disclosure is not limited thereto.

The electron transport auxiliary layer 8 may be located between the electron transport layer 5 and the light emission layer 4. The electron transport auxiliary layer 8 may further contain a hole blocking material.

The hole blocking material may include one selected from the group consisting of, for example, oxadiazole, triazole, phenanthroline, benzoxazole, benzothiazole, benzimidazole, triazine, and a combination thereof. However, the present disclosure is not limited thereto.

The electron transport layer 5 receives electrons from the cathode. The electron transport layer 5 transfers the supplied electrons to the light emission layer 4.

The electron transport layer 5 serves to facilitate the transport of electrons, and the electron transport layer 5 may contain an electron transport material.

The electron transport material may be a material electrochemically stabilized via anionization (that is, via obtaining electrons). Alternatively, a material producing stable radical anions may be an electron transport material. Alternatively, a material including a heterocyclic ring and thus being easily to be anionized using a hetero atom may be an electron transport material.

For example, the electron transport material may include one selected from the group consisting of PBD (2-(4-biphenylyl)-5-(4-tert-butylphenyl)-1,3,4oxadiazole), TAZ (3-(4-biphenyl)4-phenyl-5-tert-butylphenyl-1,2,4-triazole), spino-PBD, TPBi (2,2',2-(1,3,5-benzinetriyl)-tris(1-phenyl-1-H-benzimidazole), oxadiazole, triazole, phenanthroline, benzoxazole, benzthiazole, and combinations thereof. However, the present disclosure is not limited thereto.

For example, the electron transport material may be an organometallic compound. Specifically, the electron transport material may include an organoaluminum compound or organolithium compound such as Alq3 (tris(8-hydroxyquinolino)aluminum), Liq (8-hydroxyquinolinolatolithium), BAlq (bis(2-methyl-8-quinolinolate)-4-(phenylphenolato) aluminium), and SAlq. However, the present disclosure is not limited thereto.

Specifically, the organometallic compound may be an organolithium compound.

More specifically, a ligand bound to lithium of the organolithium compound may be a hydroxyquinoline based ligand.

The organic layer may further include an electron injection layer.

The electron injection layer serves to facilitate the injection of electrons. The electron injection material may include one selected from the group consisting of Alq3 (tris(8-hydroxyquinolino)aluminum), PBD, TAZ, spiro-PBD, BAlq, SAN, and a combination thereof. However, the present disclosure is not limited thereto. Alternatively, the electron injection layer may be made of a metal compound. The metal compound may include, for example, at least one selected from the group consisting of LiQ, LiF, NaF, KF, RbF, CsF, FrF, $BeF_2$, $MgF_2$, $CaF_2$, $SrF_2$, $BaF_2$ and $RaF_2$. However, the present disclosure is not limited thereto.

The organic layer may further include one selected from the group consisting of a hole injection layer, a hole transport layer, a hole transport auxiliary layer, an electron transport auxiliary layer, an electron injection layer, and combinations thereof in addition to the electron transport layer. Each of the hole injection layer, the hole transport layer, the hole transport auxiliary layer, the electron transport auxiliary layer, the electron transport layer and the electron injection layer may be formed of a single layer or a stack of a plurality of layers.

An organic electroluminescent device according to the present disclosure may be applied to an organic light emitting display such as a mobile device and TV. For example, FIG. 2 is a schematic cross-sectional view of an organic light emitting display 3000 according to an exemplary embodiment of the present disclosure.

Figure 2:
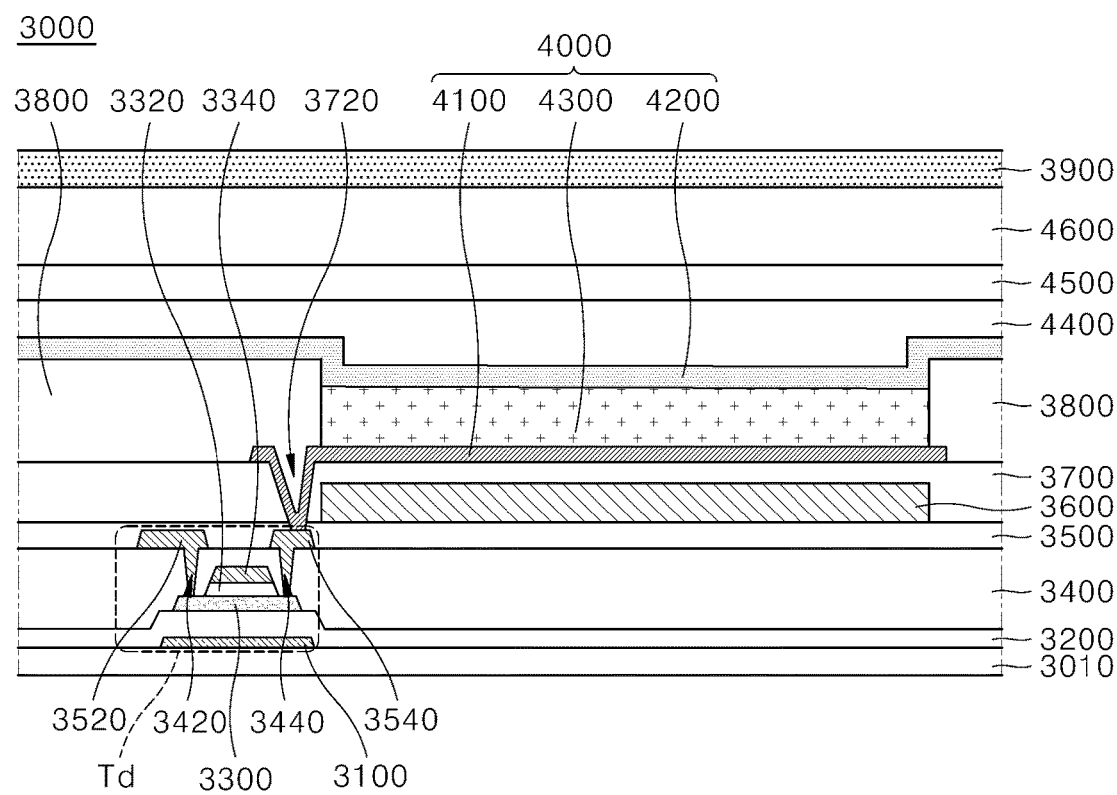
FIG. 2 is a schematic cross-sectional view of an organic light emitting display device including an organic electroluminescent device according to one embodiment of the present disclosure.

As shown in FIG. 2, the organic light emitting display 3000 may include a substrate 3010, an organic electroluminescent device 4000, and an encapsulation film 3900 covering the organic electroluminescent device 4000. A driving thin film transistor Td as a driving element, and the organic electroluminescent device 4000 connected to the driving thin film transistor Td are positioned on the substrate 3010.

Although not shown, following components are disposed on the substrate 3010: a gate line, and a data line crossing each other to define a pixel region, a power line extending in parallel with and spaced from one of the gate line and the data line, a switching thin film transistor connected to the power line and the gate line, and a storage capacitor connected to one electrode of the switching thin film transistor and the power line.

The driving thin film transistor Td is connected to the switching thin film transistor, and includes a semiconductor layer 3100, a gate electrode 3340, a source electrode 3520, and a drain electrode 3540.

The semiconductor layer 3100 is formed on the substrate 3010 and may be made of an oxide semiconductor material, polycrystalline silicon, an alloy of molybdenum titanium (MoTi), or the like. When the semiconductor layer 3100 is made of an oxide semiconductor material, a light blocking pattern (not shown) may be formed below the semiconductor layer 3100. The light blocking pattern prevents light from entering the semiconductor layer 3100 to prevent the semiconductor layer 3100 from being degraded by light. Alternatively, the semiconductor layer 3100 may be made of polycrystalline silicon. In this case, impurities may be doped into both edges of the semiconductor layer 3100.

A buffer layer 3200 made of an insulating material is formed on the semiconductor layer 3100 over an entire face of the substrate 3010. The buffer layer 3200 may be made of an inorganic insulating material such as silicon oxide or silicon nitride.

The active layer 3300 made of a conductive material such as a metal is formed on the buffer layer 3200 in a position corresponding to a center region of the semiconductor layer 3100. The active layer 3300 may be made of an oxide semiconductor layer. For example, the active layer 3300 may be made of an amorphous semiconductor of indium, gallium and zinc oxide (IGZO).

The gate electrode 3340 is formed on the active layer 3300 while a gate insulating layer 3320 is interposed therebetween. The gate insulating layer 3320 may be made of, for example, silicon oxide. The gate electrode 3340 formed of, for example, a double metal layer of a Cu film and a MoTi alloy film may be formed on the gate insulating layer 3320.

An interlayer insulating layer 3400 made of an insulating material is formed on the active layer 3300 and the gate electrode 3340 as positioned on the buffer layer 3200 over the entire face of the substrate 3010. The interlayer insulating layer 3400 may be made of an inorganic insulating material such as silicon oxide or silicon nitride, or may be made of an organic insulating material such as benzocyclobutene or photo-acryl.

The interlayer insulating layer 3400 has first and second active layer contact holes 3420 and 3440 defined therein exposing both sides of the active layer 3300 respectively. The first and second active layer contact holes 3420 and 3440 are positioned adjacent to both sides of the gate electrode 3340 respectively and are spaced apart from the gate electrode 3340.

The source electrode 3520 and the drain electrode 3540 made of a conductive material such as metal are formed on the interlayer insulating layer 3400. The source electrode 3520 and the drain electrode 3540 are spaced apart from each other while the gate electrode 3340 is positioned therebetween. The source electrode 3520 and the drain electrode 3540 contact both sides of the active layer 3300 respectively via the first and second active layer contact holes 3420 and 3440 respectively. The source electrode 3520 is connected to the power line (not shown).

The semiconductor layer 3100, the active layer 3300, the gate electrode 3340, the source electrode 3520, and the drain electrode 3540 may form the driving thin film transistor Td. The driving thin film transistor Td may have a coplanar structure in which the gate electrode 3340, the source electrode 3520, and the drain electrode 3540 are positioned above the semiconductor layer 3100.

In contrast, the driving thin film transistor Td may have an inverted staggered structure in which the gate electrode is disposed under the semiconductor layer, while the source electrode and the drain electrode are positioned above the semiconductor layer. In this case, the semiconductor layer may be made of amorphous silicon. The switching thin film transistor (not shown) may have a structure substantially the same as that of the driving thin film transistor Td.

An insulating film 3500 having a drain contact hole 3720 defined therein exposing the drain electrode 3540 of the driving thin film transistor Td may be formed to cover the driving thin film transistor Td. The insulating film 3500 may be made of an inorganic insulating material or an organic insulating material.

In one embodiment, the organic light emitting display 3000 may include a color filter 3600 that absorbs light generated from the organic electroluminescent device 4000. For example, the color filter 3600 may absorb red (R), green (G), blue (B), and white (W) light. In this case, red, green, and blue color filter patterns for absorbing light may be formed separately on corresponding pixel areas respectively. A corresponding color filter pattern may overlap an organic layer 4300 of an organic electroluminescent device that emits light of a corresponding wavelength band to be absorbed. Adopting the color filter 3600 may allow the organic light emitting display 3000 to implement full color.

For example, when the organic light emitting display 3000 is of a bottom emission type, the color filter 3600 may be disposed above the insulating film 3500 in a corresponding position to the corresponding organic electroluminescent device 4000. In an alternative embodiment, when the organic light emitting display 3000 is of the top emission type, the color filter 3600 may be positioned above the corresponding organic electroluminescent device 4000, that is, above the second electrode 4200. In one embodiment, the color filter 3600 may be formed to a thickness of about 2 µm to about 5 µm. In this case, the organic electroluminescent device 4000 may have the structure shown in FIG. 1.

An overcoat layer 3700 is formed to cover the color filter 3600 formed on the insulating layer 3500. The overcoat layer 3700 may be made of an organic material such as photoacryl (PAC).

The first electrode 4100 is formed on the overcoat layer 3700. The first electrode 4100 is patterned with a bank layer 3800 to corresponding to each pixel region. The first electrode 4100 is connected to the drain electrode 3540 of the driving thin film transistor Td via the drain contact hole 3720 penetrating the insulating film 3500 and the overcoat layer 3700. Accordingly, the active layer 3300 of the driving thin film transistor Td is electrically connected to the first electrode 4100.

The first electrode 4100 may be an anode and may be made of a conductive material having a relatively large work function value. For example, the first electrode 410 may be made of a transparent conductive material such as of ITO, IZO or ZnO.

In one embodiment, when the organic light emitting display 3000 is of a top emission type, a reflective electrode or a reflective layer may be further formed below the first electrode 4100. For example, the reflective electrode or the reflective layer may be made of one of aluminum (Al), silver (Ag), nickel (Ni), and aluminum-palladium-copper (APC) alloy.

The bank layer 3800 is formed on the overcoat layer 3700 to cover edges of the first electrode 4100 and the overcoat layer 3700. The bank layer 3800 exposes a central region of the first electrode 4100 corresponding to each pixel region.

The organic layer 4300 is formed on the first electrode 4100.

The second electrode 4200 is formed on the organic layer 4300. The second electrode 4200 may be disposed in the entirety of a display area and may be used as a cathode and may be made of a conductive material having a relatively small work function. For example, the second electrode 4200 may be made of one of aluminum (Al), magnesium (Mg), and aluminum-magnesium alloy (AlMg).

The first electrode 4100, the organic layer 4300, and the second electrode 4200 forum the organic electroluminescent device 4000.

A first passivation layer 4400 and a second passivation layer 4500 are sequentially stacked on the second electrode 4200. As shown in FIG. 2, the first passivation layer 4400 may be formed on an entirety of the second electrode 4200. Then, the second passivation layer 4500 may be formed on the first passivation layer 4400. Thus, moisture, hydrogen, and oxygen may be prevented from penetrating into the organic layer 4300 and the second electrode 4200. That is, the first passivation layer 4400 is formed on the second electrode 4200 to prevent the organic layer 4300 and the second electrode 4200 from being damaged by moisture, oxygen, or the like, or thus from having deteriorated light emission characteristics. For example, the first passivation layer 4400 may be made of an anthracene-based compound, Alq3, or the like.

The first passivation layer 4400 may be deposited on the second electrode 4200 uniformly and evenly. Since the first passivation layer 4400 is uniformly and evenly deposited, the second passivation layer 4500 is also uniformly deposited on the first passivation layer 4400. As such, the first and second protective layers 4400 and 4500 that are evenly and uniformly formed may prevent penetration of water or oxygen into the organic electroluminescent device 4000, such that the lifetime of the organic electroluminescent device 4000 can be improved.

The second passivation layer 4500 may be formed between the organic electroluminescent device 4000 and an adhesive film 4600 to prevent the organic electroluminescent device 4000 from being damaged by moisture, oxygen, or the like, or from having deteriorated light emission characteristics. The second passivation layer 4500 is formed to be in contact with the adhesive film 4600, thereby preventing moisture, hydrogen, oxygen, and the like from flowing into the organic electroluminescent device 4000. The second passivation layer 4500 may be made of an inorganic insulating layer such as silicon nitride, silicon oxide, or silicon oxynitride.

The adhesive film 4600 may be formed on the second passivation layer 4500. In this connection, in order to prevent external moisture from penetrating into the organic electroluminescent device 4000, an encapsulation film 3900 may be formed on the adhesive film 4600. That is, the encapsulation film 3900 is formed on the second passivation layer 4500. The encapsulation film 3900 may adhere to the second passivation layer 4500 via the adhesive film 4600.

After the adhesive film 4600 is applied to a front face of the second passivation layer 4500 or a back face of the encapsulation film 3900, the encapsulation film 3900 may adhere to the substrate 3010 on which the organic electroluminescent device 4000 is formed via the adhesive film 4600.

The adhesive film 4600 may be made of, for example, an epoxy adhesive.

The encapsulation film 3900 may be embodied as, for example, a double metal layer of a Fe film and a Ni film. Alternatively, the encapsulation film 3900 may be embodied as a triple layer structure (not shown) in which a first inorganic layer, an organic layer, and a second inorganic layer are sequentially stacked vertically. However, the present disclosure is not limited thereto.

Hereinafter, Examples and Comparative Examples of the present disclosure are described. The Present Examples are merely examples of the present disclosure. The present disclosure is not limited to the Present Examples as described below.

EXAMPLES

Hereinafter, compounds used in the Present Examples and Comparative Examples were synthesized as follows.

Synthesis Example 1

Preparation of Compound 1

1-A) Preparation of Intermediate 1-A

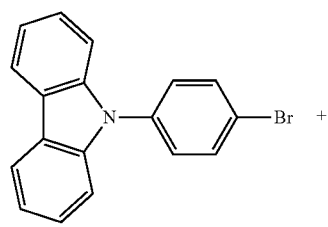

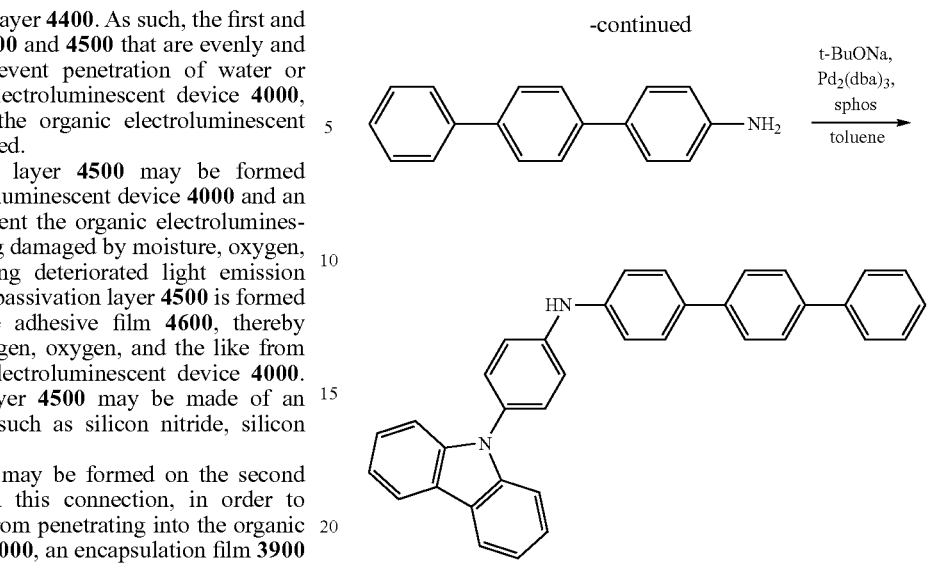

Under nitrogen stream, 9-(4-bromophenyl)-9H-carbazole (50.0 g, 155.2 mmol), [1,1':4',1''-terphenyl]-4-amine (41.88 g, 170.7 mmol), sodium tert butoxide (29.83 g, 310.4 mmol), tris(dibenzylideneacetone)dipalladium (0) (2.84 g, 3.10 mmol), 2-dicyclohexylphosphino-2',6'-dimethoxybiphenyl (2.55 g, 6.21 mmol), and toluene 800 mL were added into a 2000 mL flask and were stirred therein while being refluxed. After completion of the reaction, a toluene layer was extracted using 500 mL of water. An extracted solution was treated with MgSO$_4$ to remove residual water, and concentrated under reduced pressure, and purified using column chromatography. The resulting solid is subjected to recrystallization using dichloromethane/heptane, thereby obtaining 57.10 g of an intermediate 1-A in 75.6% yield.

1-B) Preparation of Compound 1

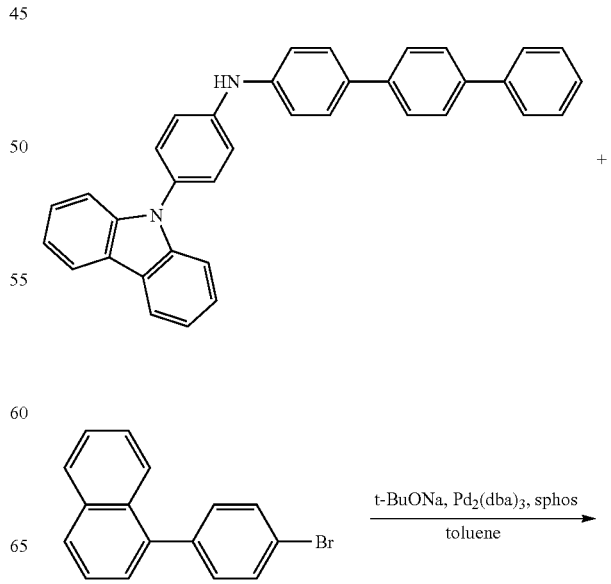

-continued

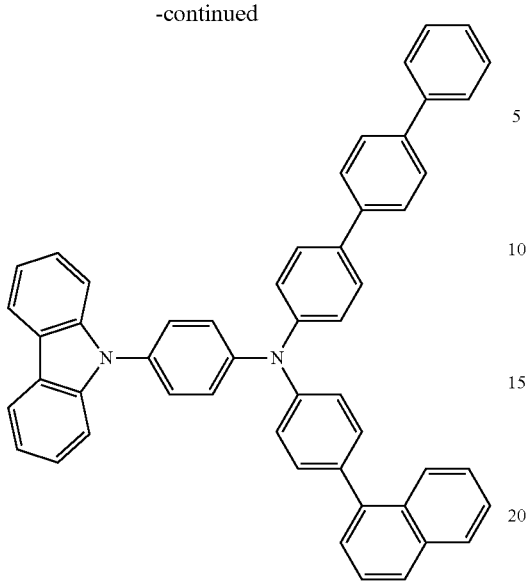

Under nitrogen stream, N-(4-(9H-carbazol-9-yl)phenyl)-[1,1':4',1''-terphenyl]-4-amine (8.0 g, 16.44 mmol), 1-(4-bromophenyl)naphthalene (5.12 g, 18.08 mmol), sodium tert butoxide (3.16 g, 32.88 mmol), tris(dibenzylideneacetone)dipalladium (0) (0.30 g, 0.33 mmol), 2-dicyclohexylphosphino-2',6'-dimethoxybiphenyl (0.27 g, 0.66 mmol), and 100 mL of toluene were added into a 250 mL flask and were stirred therein while being refluxed. After completion of the reaction, a toluene layer was extracted using 50 mL of water. An extracted solution was treated with MgSO$_4$ to remove residual water, and concentrated under reduced pressure, and purified using column chromatography. The resulting solid is subjected to recrystallization using dichloromethane/heptane, thereby obtaining 6.85 g of Compound 1 in 60.5% yield.

MS (MALDI-TOF) m/z: 688 [M]+

Synthesis Example 2

Preparation of Compound 2

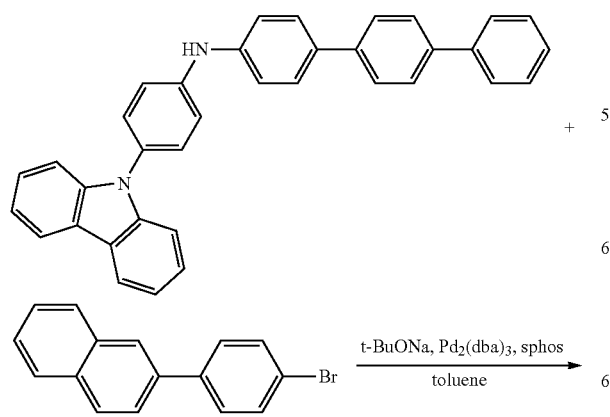

-continued

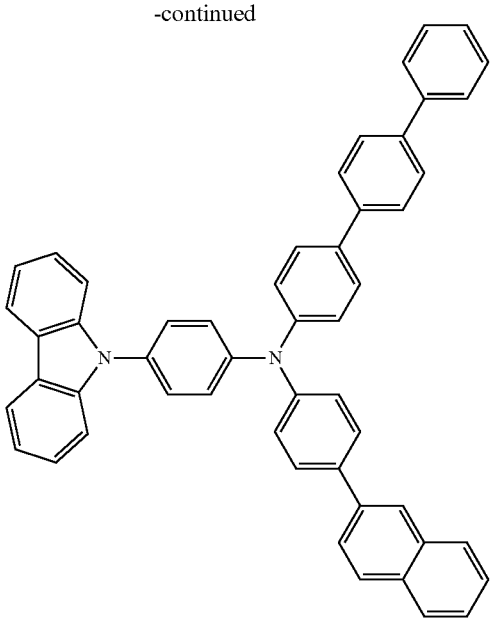

6.07 g of Compound 2 is synthesized at 53.6% yield in the same manner as in the preparation of Compound 1, except that 2-(4-bromophenyl)naphthalene (5.12 g, 18.08 mmol) was used instead of 1-(4-bromophenyl)naphthalene.

MS (MALDI-TOF) m/z: 688 [M]+

Synthesis Example 3

Preparation of Compound 3

3-A) Preparation of Intermediate 3-A

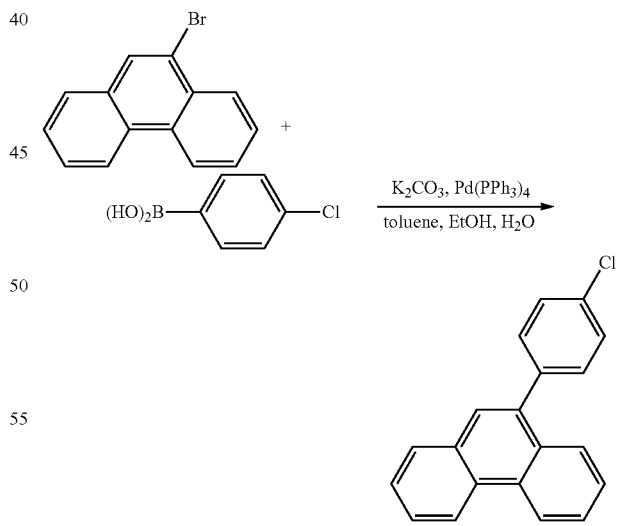

Under nitrogen stream, 9-bromophenanthrene (40.0 g, 155.6 mmol), (4-chlorophenyl)boronic acid (26.76 g, 171.1 mmol), potassium carbonate (43.0 g, 311.1 mmol), tetrakis(triphenylphosphine)palladium (0) (5.39 g, 4.67 mmol), toluene (300 mL), EtOH (100 mL) and H$_2$O (100 mL) were added into a 1000 mL flask and were stirred therein while being refluxed. After completion of the reaction, a toluene layer was extracted using toluene and water. An extracted solution was treated with MgSO$_4$ to remove residual water, and concentrated under reduced pressure, and purified using column chromatography. The resulting solid is subjected to recrystallization using dichloromethane/heptane, thereby obtaining 38.5 g of an intermediate 3-A in 85.7% yield.

3-B) Preparation of Compound 3

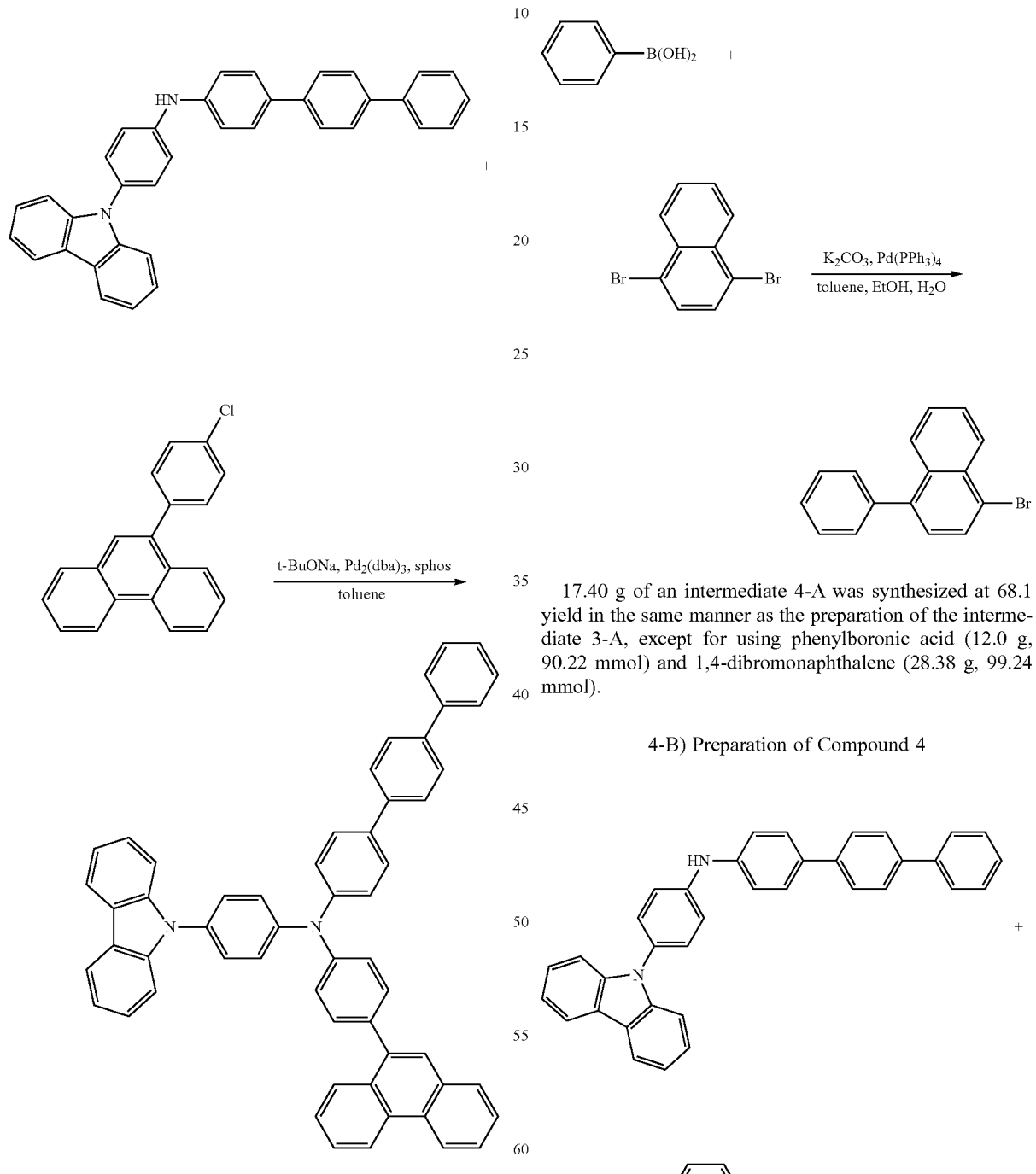

6.37 g of Compound 3 was synthesized at 52.4% yield in the same manner as the preparation of Compound 1, except that 9-(4-chlorophenyl)phenanthrene (5.22 g, 18.08 mmol) was used instead of 1-(4-bromophenyl) naphthalene.

MS (MALDI-TOF) m/z: 738 [M]+

Synthesis Example 4

Preparation of Compound 4

4-A) Preparation of Intermediate 4-A

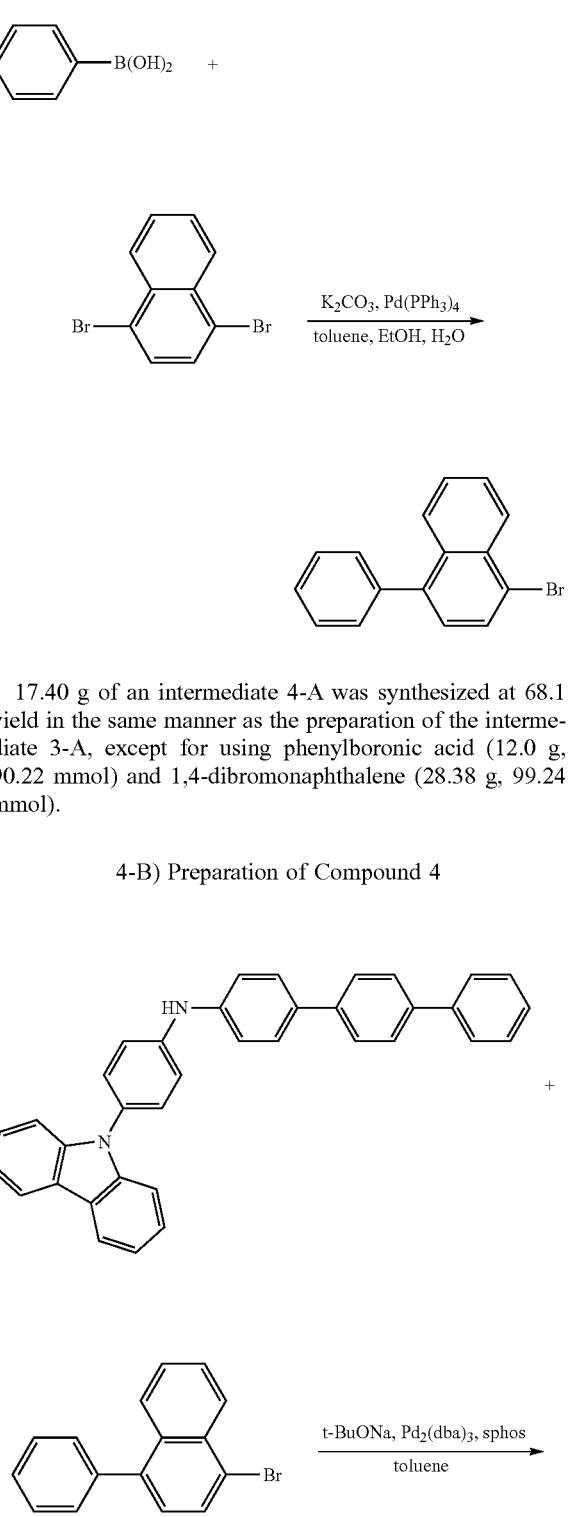

17.40 g of an intermediate 4-A was synthesized at 68.1 yield in the same manner as the preparation of the intermediate 3-A, except for using phenylboronic acid (12.0 g, 90.22 mmol) and 1,4-dibromonaphthalene (28.38 g, 99.24 mmol).

4-B) Preparation of Compound 4

-continued

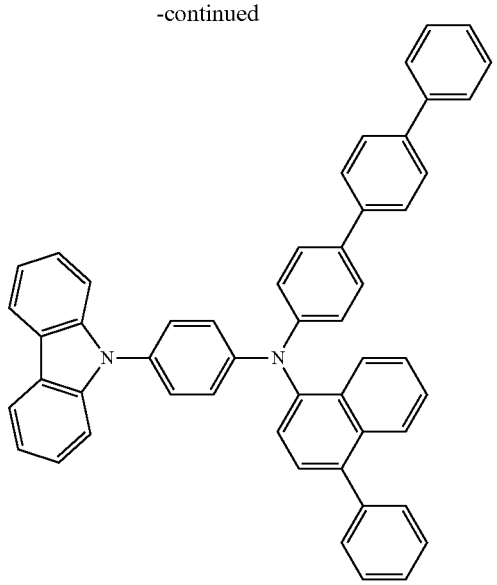

6.01 g of Compound 2 was synthesized at 55.8% yield in the same manner as in the preparation of Compound 1, except that 1-bromo-4-phenylnaphthalene (5.12 g, 18.80 mmol) was used instead of 1-(4-bromophenyl)naphthalene.
MS (MALDI-TOF) m/z: 688 [M]+

Synthesis Example 5

Preparation of Compound 11

5-A) Preparation of Intermediate 5-A

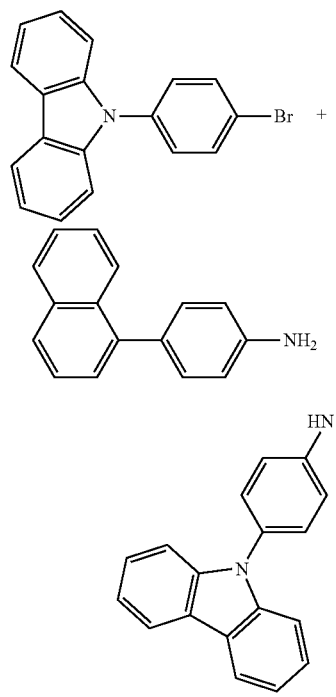

45.10 g of an intermediate 5-A was synthesized at 63.1% yield in the same manner as in the preparation of the intermediate 1-A, except using 4-(naphthalen-1-yl)aniline (37.43 g, 170.7 mmol) instead of [1,1':4',1'-terphenyl]-4-amine.

5-B) Preparation of Intermediate 5-B

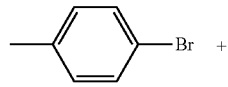

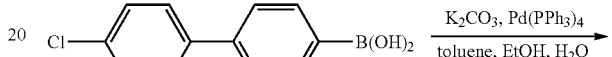

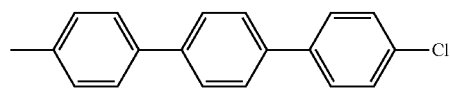

11.85 g of an intermediate 5-B was produced at 72.7% yield in the same manner as the preparation of the intermediate 3-A except for using 1-bromo-4-methylbenzene (10.0 g, 58.47 mmol) and (4'-chloro-[1,1'-biphenyl]-4-yl)boronic acid (14.95 g, 64.31 mmol).

5-C) Preparation of Compound 11

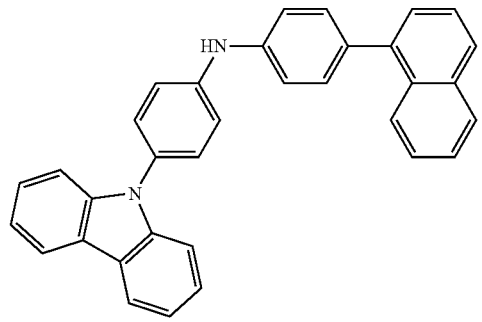

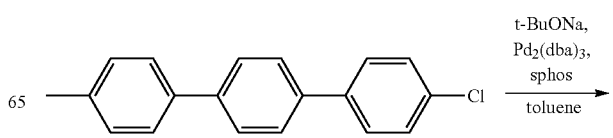

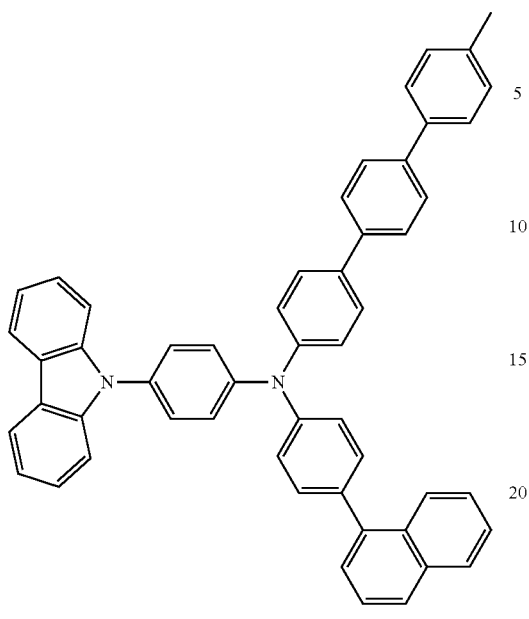

5.44 g of Compound 11 was produced at a yield of 50.9% in the same manner as in the preparation of Compound 1, except that N-(4-(9H-carbazol-9-yl)phenyl)-4-(naphthalen-1-yl)aniline (7.0 g, 15.20 mmol) and 4-chloro-4'-methyl-1,1':4',1''-terphenyl (4.66 g, 16.72 mmol).

MS (MALDI-TOF) m/z: 702 [M]+

Synthesis Example 6

Preparation of Compound 15

6-A) Preparation of Intermediate 6-A

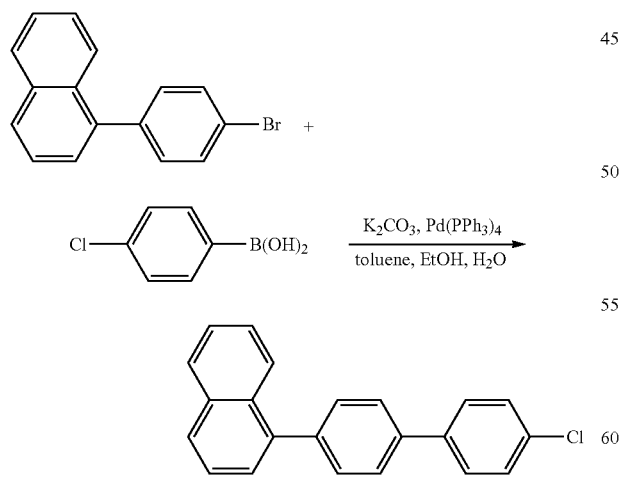

39.82 g of an intermediate 6-A was produced at 81.3% yield in the same manner as the preparation of the intermediate 3-A, except that 1-(4-bromophenyl)naphthalene (44.06 g, 155.6 mmol) was used instead of 9-bromophenanthrene.

6-B) Preparation of Compound 15

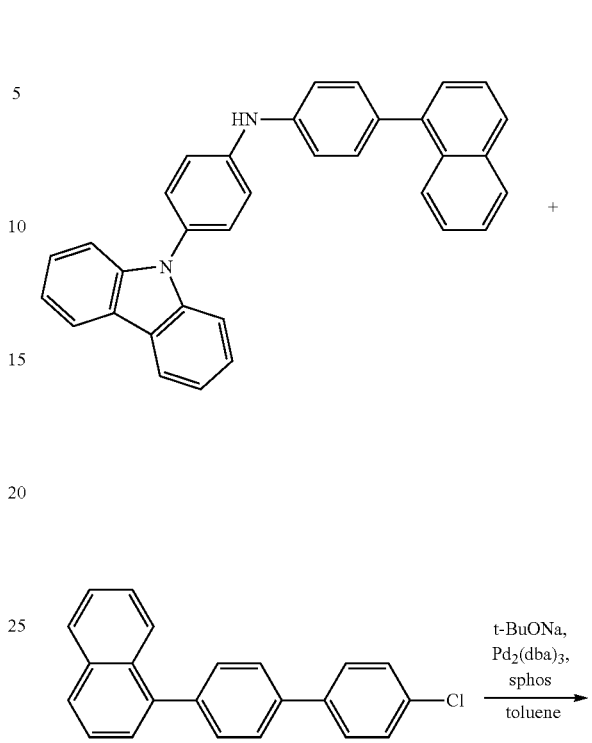

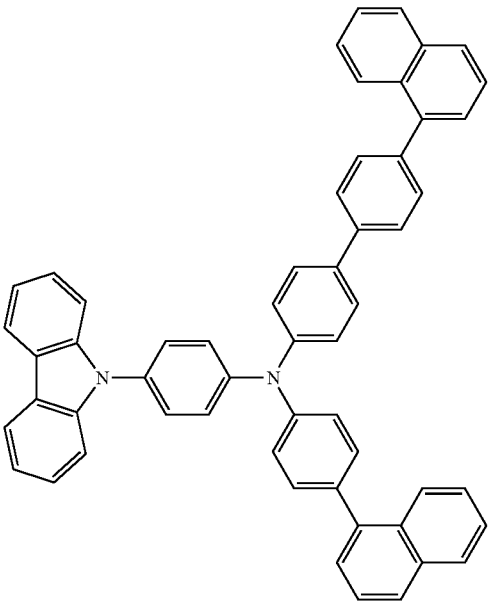

6.21 g of Compound 15 was produced at 55.3% yield in the same manner as the preparation of Compound 1 except that N-(4-(9H-carbazol-9-yl)phenyl)-4-(naphthalen-1-yl)aniline (7.0 g, 15.20 mmol) and 1-(4'-chloro-[1,1'-biphenyl]-4-yl)naphthalene (5.26 g, 16.72 mmol).

MS (MALDI-TOF) m/z: 738 [M]+

Synthesis Example 7

Preparation of Compound 21

7-A) Preparation of Intermediate 7-A

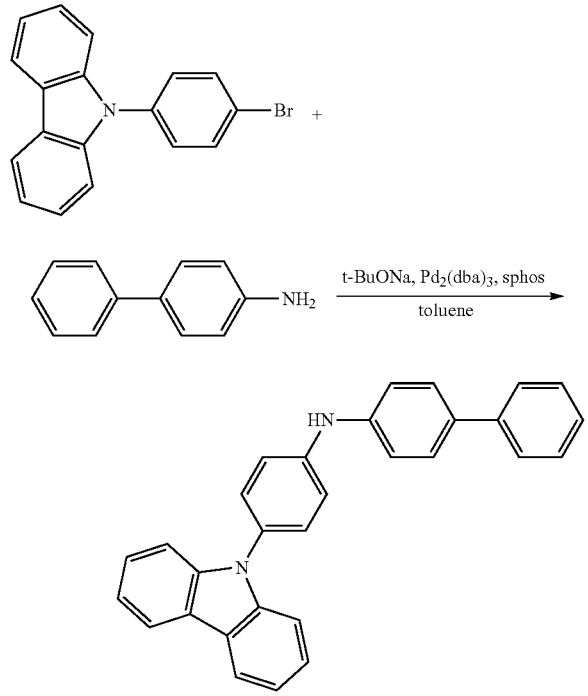

49.75 g of an intermediate 7-A was obtained at 78.1% yield in the same manner as the preparation of the intermediate 1-A, except that [1,1'-biphenyl]-4-amine (28.89 g, 170.7 mmol) was used instead of [1,1':4',1''-terphenyl]-4-amine.

7-B) Preparation of Compound 21

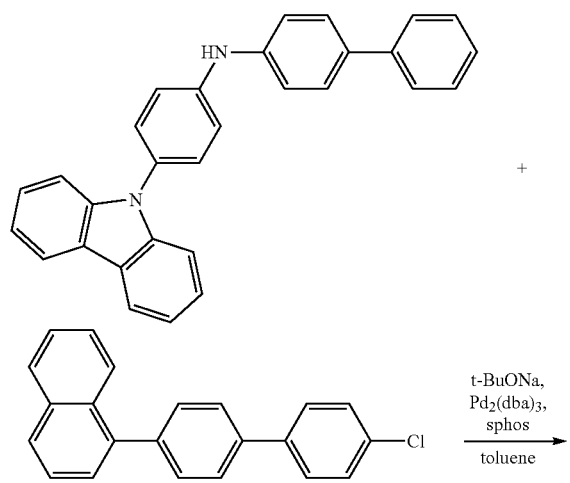

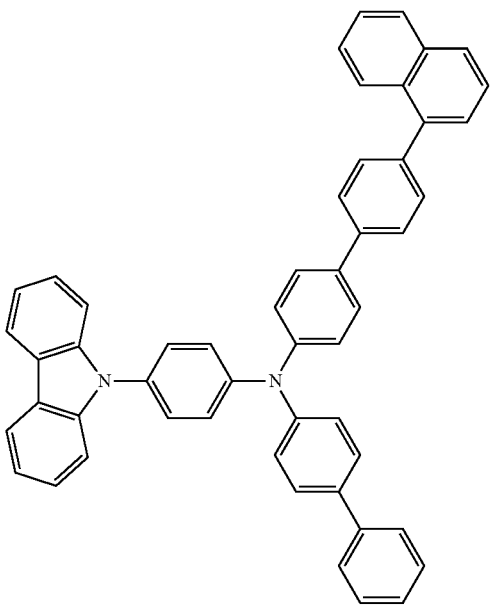

5.30 g of Compound 21 was produced at 52.6% yield in the same manner as in the preparation of Compound 1, except that N-(4-(9H-carbazol-9-yl)phenyl)-[1,1'-biphenyl]-4-amine (6.0 g, 14.62 mmol) and 1-(4'-chloro-[1,1'-biphenyl]-4-yl)naphthalene (5.05 g, 16.08 mmol) were used.

MS (MALDI-TOF) m/z: 688 [M]+

Synthesis Example 8

Preparation of Compound 26

8-A) Preparation of Intermediate 8-A

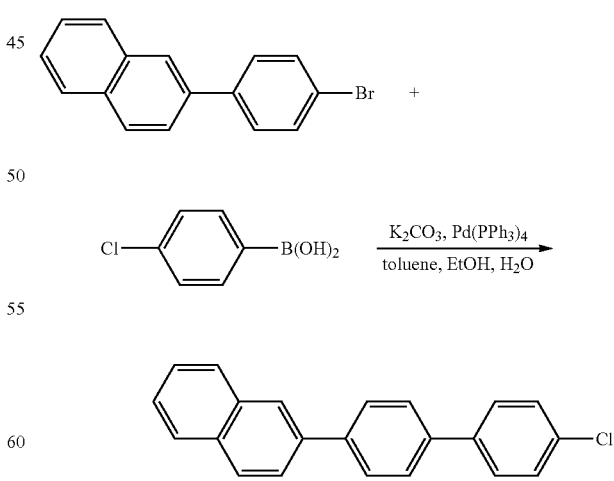

39.82 g of an intermediate 8-A was obtained at 81.3% yield in the same manner as the preparation of the intermediate 3-A except for using 2-(4-bromophenyl)naphthalene (44.06 g, 155.6 mmol) instead of 9-bromophenanthrene.

8-B) Preparation of Compound 26

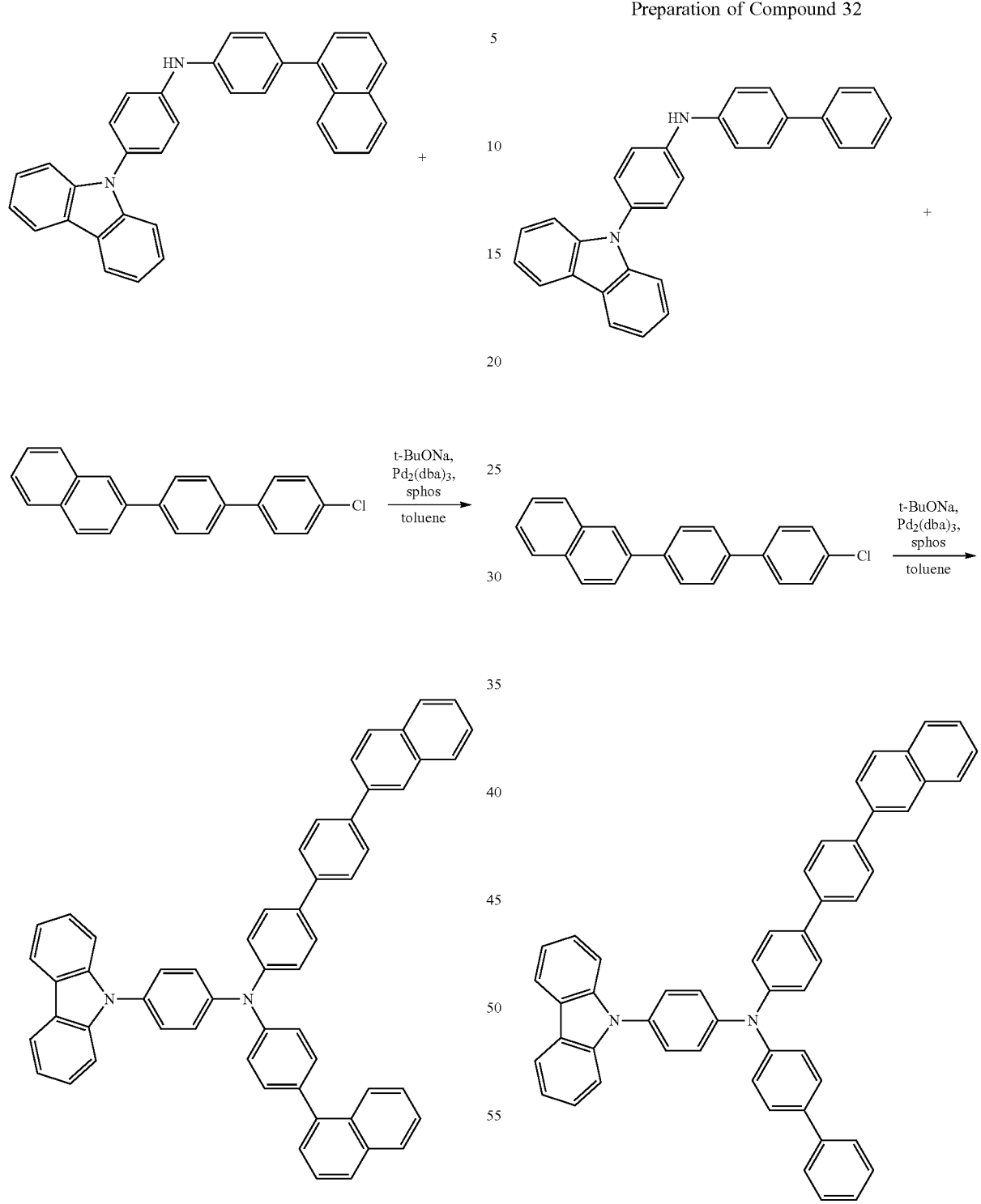

5.72 g of Compound 26 was produced at a yield of 50.9% in the same manner as in the preparation of Compound 1 except for using N-(4-(9H-carbazol-9-yl)phenyl)-4-(naphthalen-1-yl)aniline (7.0 g, 15.20 mmol) and 2-(4'-chloro-[1,1'-biphenyl]-4-yl)naphthalene (5.26 g, 16.72 mmol).

MS (MALDI-TOF) m/z: 738 [M]+

Synthesis Example 9

Preparation of Compound 32

5.52 g of Compound 32 was produced at a yield of 54.8% in the same manner as in the preparation of Compound 1 except for using N-(4-(9H-carbazol-9-yl)phenyl)-[1,1'-biphenyl]-4-amine (6.0 g, 14.62 mmol) and 2-(4'-chloro-[1,1'-biphenyl]-4-yl)naphthalene (5.05 g, 16.08 mmol).

MS (MALDI-TOF) m/z: 688 [M]+

Synthesis Example 10

Preparation of Compound 43

10-A) Preparation of Intermediate 10-A

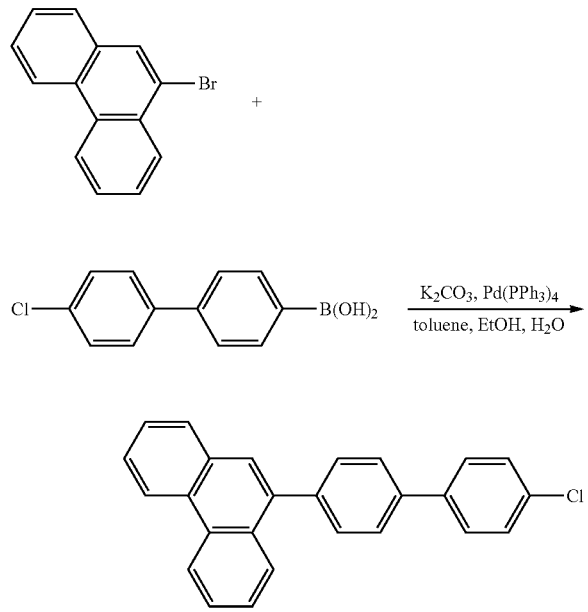

43.25 g of an intermediate 10-A was produced at 76.2% yield in the same manner as in the preparation of the intermediate 3-A except for using (4'-chloro-[1,1'-biphenyl]-4-yl)boronic acid (39.78 g, 171.1 mmol) instead of (4-chlorophenyl)boronic acid.

10-B) Preparation of Compound 43

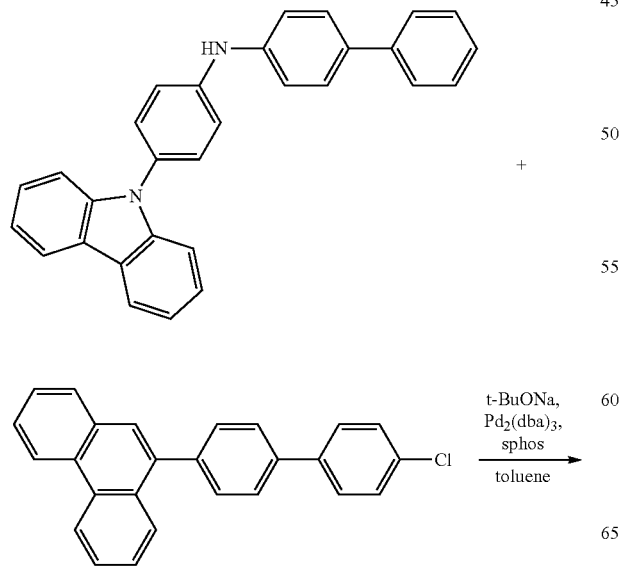

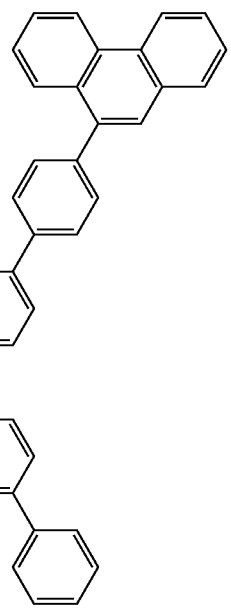

5.46 g of Compound 43 was produced at 50.6% yield in the same manner as the preparation of Compound 1 except for using N-(4-(9H-carbazol-9-yl)phenyl)-[1,1'-biphenyl]-4-amine (6.0 g, 14.62 mmol) and 9-(4'-chloro-[1,1'-biphenyl]-4-yl)phenanthrene (5.87 g, 16.08 mmol).

MS (MALDI-TOF) m/z: 738 [M]+

Synthesis Example 11

Preparation of Compound 48

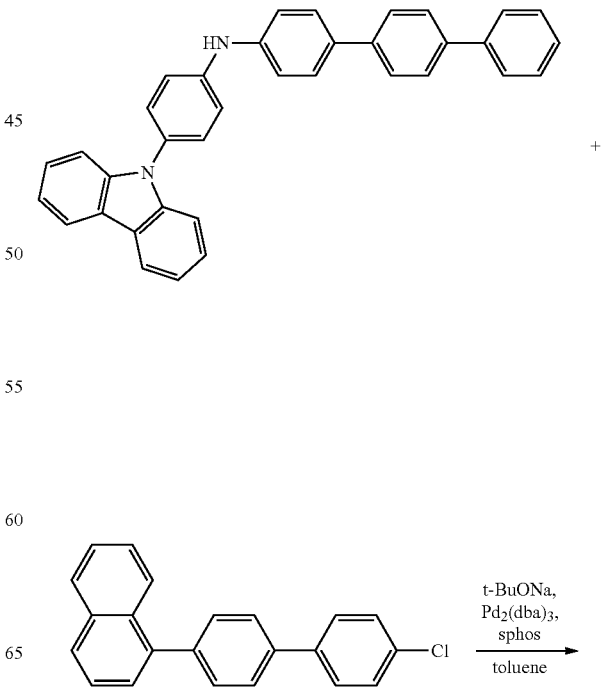

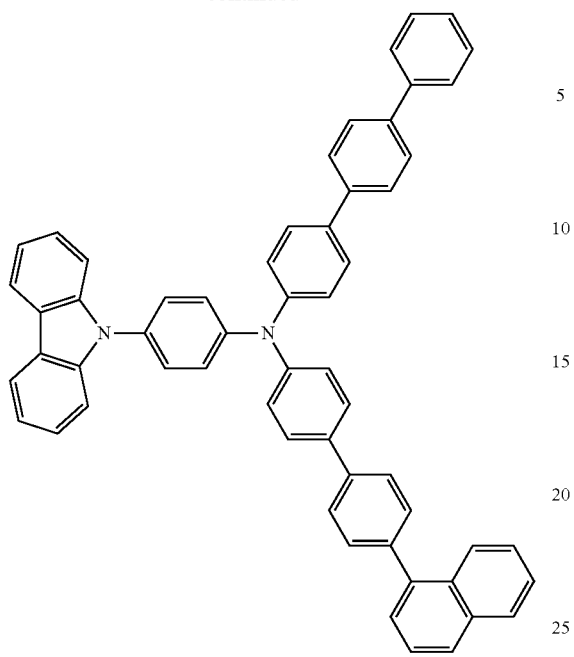

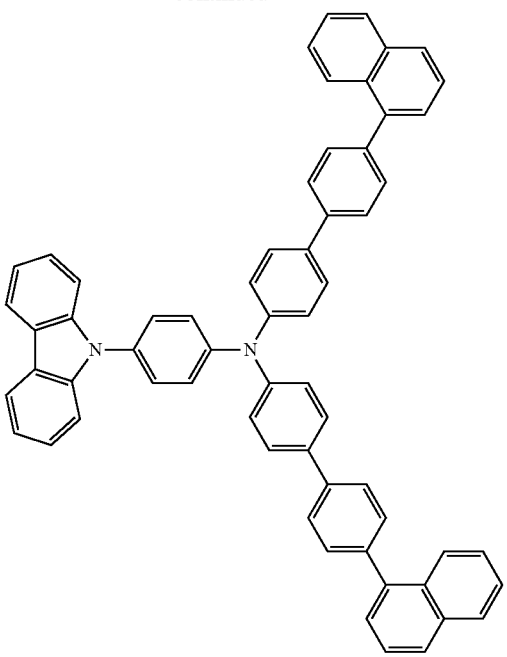

6.48 g of Compound 48 was produced at a yield of 54.0% in the same manner as in the preparation of Compound 1 except that 1-(4'-chloro-[1,1'-biphenyl]-4-yl) naphthalene (5.69 g, 18.08 mmol) was used instead of 1-(4-bromophenyl)naphthalene.

MS (MALDI-TOF) m/z: 764 [M]+

Compound 49 was obtained in 8.25 g, and at 52.3% yield in the same manner as in the preparation of Compound 1 except that 4-(9H-carbazol-9-yl)aniline (5.0 g, 19.36 mmol) and 1-(4'-chloro-[1,1'-biphenyl]-4-yl)naphthalene (13.41 g, 42.58 mmol) were used.

MS (MALDI-TOF) m/z: 814 [M]+

Synthesis Example 12

Preparation of Compound 49

Synthesis Example 13

Preparation of Compound 55

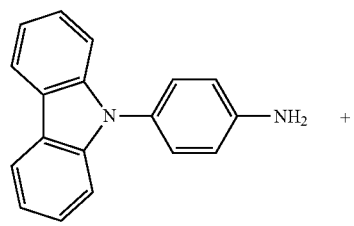 +

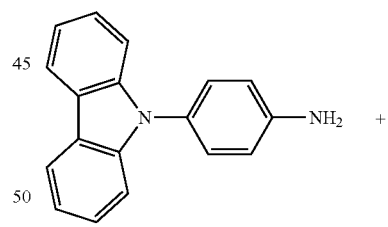 +

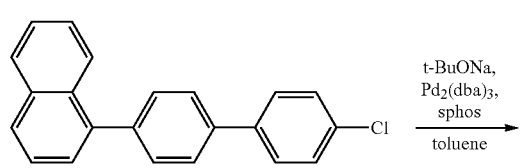 t-BuONa, Pd$_2$(dba)$_3$, sphos, toluene →

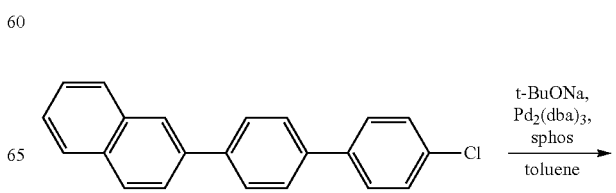 t-BuONa, Pd$_2$(dba)$_3$, sphos, toluene →

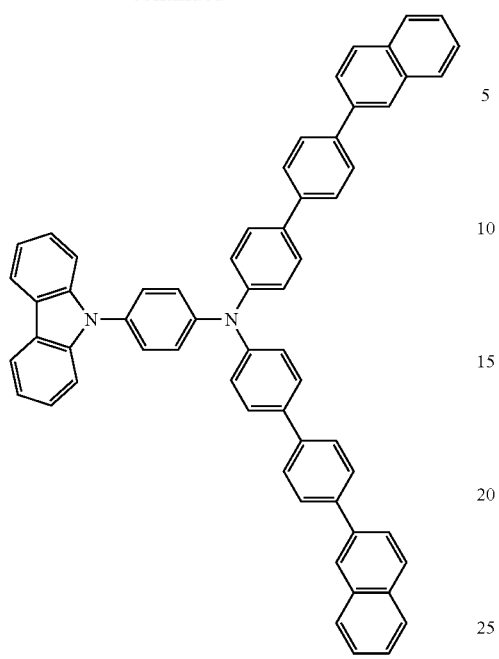

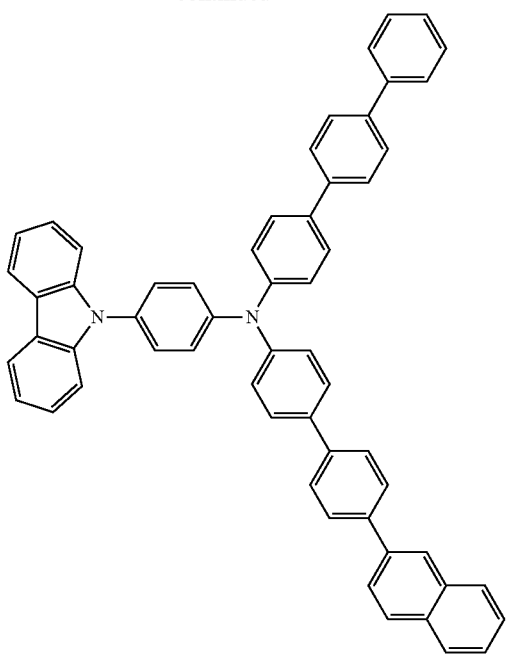

Compound 55 was obtained in 7.86 g and at 49.8% yield in the same manner as in the preparation of Compound 1 except that 4-(9H-carbazol-9-yl)aniline (5.0 g, 19.36 mmol) and 2-(4'-chloro-[1,1'-biphenyl]-4-yl)naphthalene (13.41 g, 42.58 mmol) were used.

MS (MALDI-TOF) m/z: 814 [M]+

Synthesis Example 14

Preparation of Compound 59

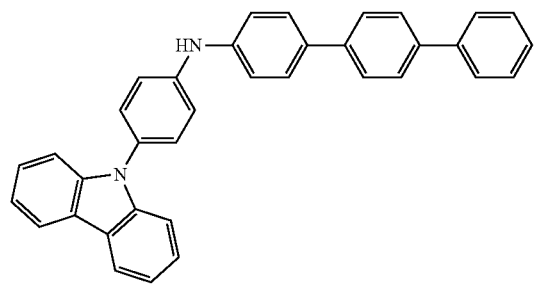

+

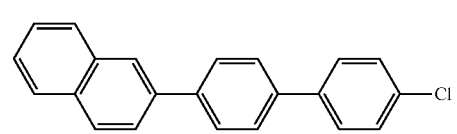 → (t-BuONa, Pd$_2$(dba)$_3$, sphos, toluene)

6.59 g of Compound 59 was prepared at a yield of 54.0% in the same manner as in preparation of Compound 1 except that 2-(4'-chloro-[1,1'-biphenyl]-4-yl)naphthalene (5.69 g, 18.08 mmol) was used instead of 1-(4-bromophenyl)naphthalene.

MS (MALDI-TOF) m/z: 764 [M]+

Synthesis Example 15

Preparation of Compound 63

+

→ t-BuONa, Pd$_2$(dba)$_3$, sphos, toluene

-continued

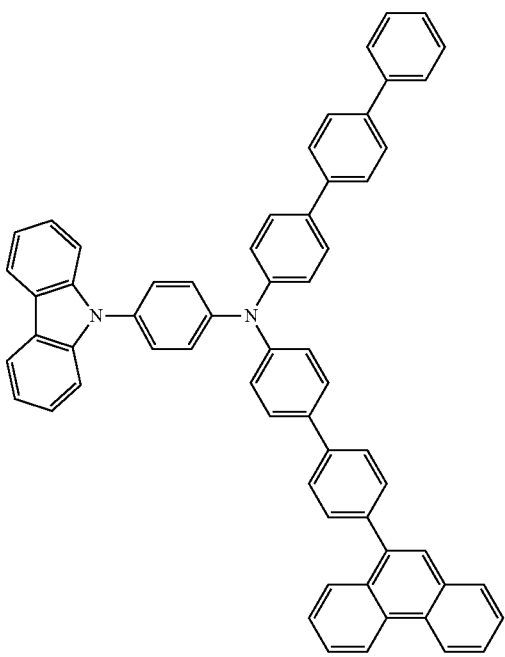

Compound 63 was obtained in 6.87 g and at 51.3% yield in the same manner as in the preparation of Compound 1 except for using 9-(4'-chloro-[1,1'-biphenyl]-4-yl)phenanthrene (6.60 g, 18.08 mmol) instead of 1-(4-bromophenyl)naphthalene.

MS (MALDI-TOF) m/z: 814 [M]+

Synthesis Example 16

Preparation of Compound 118

16-A) Preparation of Intermediate 16-A 15.31 g of an intermediate 16-A was prepared at 62.0% yield in the same manner as the preparation of the intermediate 3-A, except that 1-naphthalene boronic acid (15.0 g, 87.21 mmol) and 1-bromo-2-iodobenzene (27.14 g, 95.94 mmol) were used.

16-B) Preparation of Intermediate 16-B

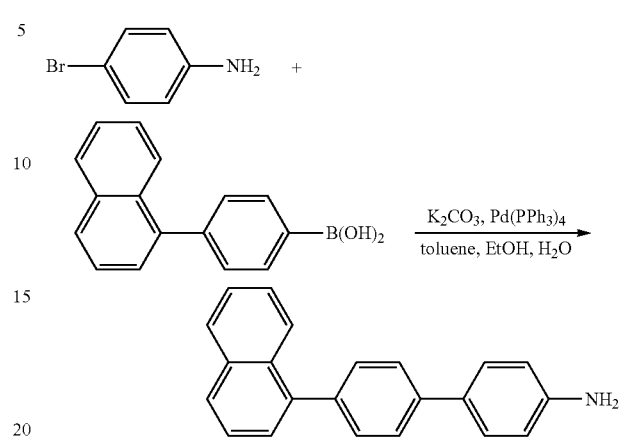

17.90 g of an intermediate 16-B was obtained at 69.5% yield in the same manner as the preparation of the intermediate 3-A, except for using 4-bromoaniline (15.0 g, 87.19 mmol) and (4-(naphthalen-1-yl)phenyl)boronic acid (27.14 g, 95.91 mmol).

16-C) Preparation of Intermediate 16-C

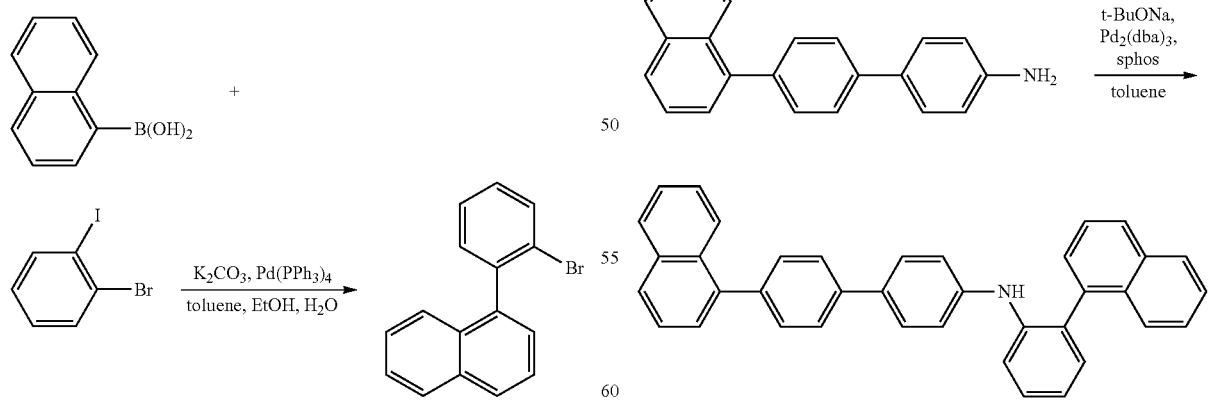

An intermediate 16-C was produced in 12.58 g and at 71.6% yield in the same manner as in the preparation of the intermediate 1-A except for using 1-(2-bromophenyl)naphthalene (10.0 g, 35.31 mmol) and 4'-(naphthalen-1-yl)-[1,1'-biphenyl]-4-amine (11.47 g, 38.85 mmol).

16-D) Preparation of Compound 118

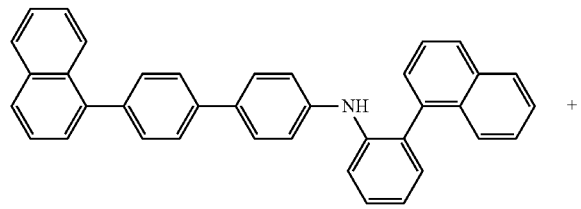

+

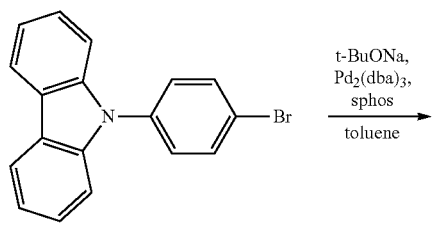

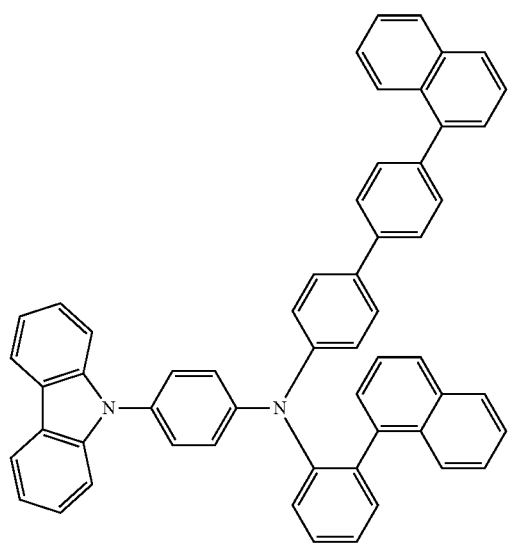

6.25 g of Compound 118 was produced at 52.6% yield in the same manner as the preparation of Compound 1 except for using 4'-(naphthalen-1-yl)-N-(2-(naphthalen-1-yl)phenyl)-[1,1'-biphenyl]-4-amine (8.0 g, 16.08 mmol) and 9-(4-bromophenyl)-9H-carbazole (5.70 g, 17.68 mmol).

MS (MALDI-TOF) m/z: 738 [M]+

Example 1

Organic Electroluminescent Device Preparation

An anode made of ITO was formed on a substrate on which a reflective layer is formed. Then, the anode was subjected to surface treatment with $N_2$ plasma or UV-ozone. HAT-CN was deposited on the anode to a thickness of 10 nm to form a hole injection layer (HIL). Subsequently, a hole transport layer (HTL) was deposited on the HIL by depositing N4,N4,N4',N4'-tetra([1,1'-biphenyl]-4-yl)-[1,1'-biphenyl]-4,4'-diamine on the HL to a thickness of 110 nm.

Vacuum deposition of Compound 1 on the hole transport layer to a thickness of 10 nm was performed to form a hole transport auxiliary layer. While depositing 25 nm of 9,10-bis(2-naphthyl)anthraces (ADN) as a blue light emission layer (EML) on the hole transport auxiliary layer, about 3 wt % of 2,5,8,11-tetra-butyl-perylene (t-Bu-Perylene) as a dopant was doped into the AND. Then, an anthracene derivative and LiQ were mixed with each other at a mass ratio of 1:1 to form a mixture which in turn was deposited on the EML to a thickness of 30 nm to form an electron transport layer (ETL). Then, LiQ was deposited to a thickness of 1 nm on the ETL to form an electron injection layer (EIL). Thereafter, a mixture of magnesium and silver (Ag) in a mass ratio of 9:1 was deposited on the EL to a thickness of 15 nm to form a cathode.

Then, N4,N4'-bis[4-[bis(3-methylphenyl)amino]phenyl]-N4,N4'-diphenyl-[1,1'-biphenyl]-4,4'-diamine (DNTPD) as a capping layer was deposited to a thickness of 60 am on the cathode. Then, a seal cap containing a moisture absorbent was bonded onto the capping layer with a UV curable adhesive to protect the organic electroluminescent device from 02 or moisture in the atmosphere. In this way, the organic electroluminescent device was prepared.

Examples 2 to 16

Organic electroluminescent devices were prepared in the same manner as in Example 1 except for using Compound 2 to Compound 4, and compounds 11, 15, 21, 26, 32, 43, 48, 49, 55, 59, 63, and 118 instead of the compound 1 as the hole transport auxiliary layer in Example 1.

Comparative Examples 1 to 3

Organic electroluminescent devices were prepared in the same manner as in Example 1 except that NPB and following [compound A] to [compound C] were used instead of Compound 1 as the hole transport auxiliary layer in Example 1.

Compound A

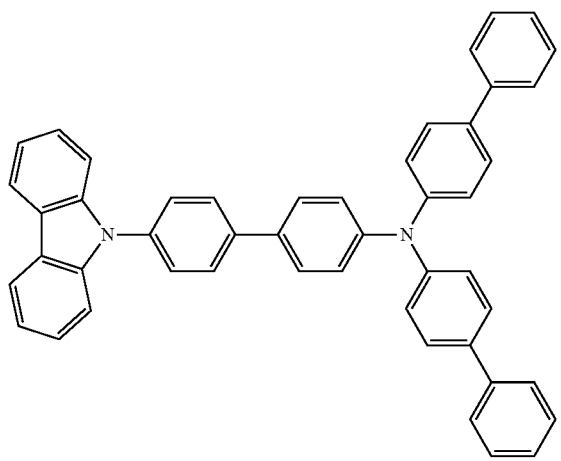

-continued

Compound B

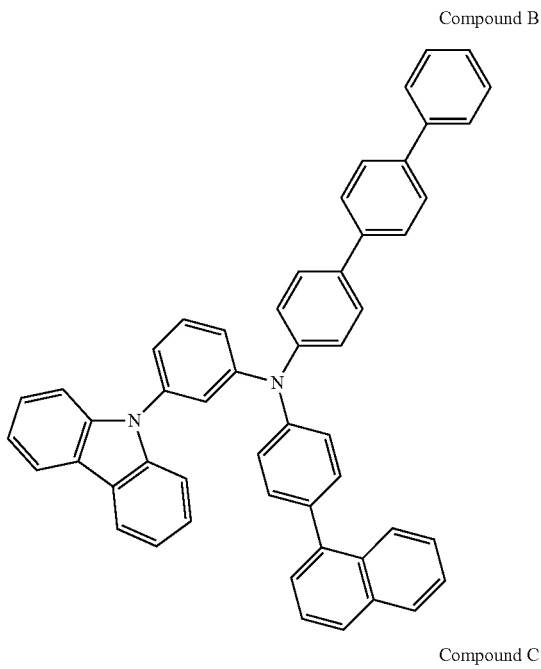

Compound C

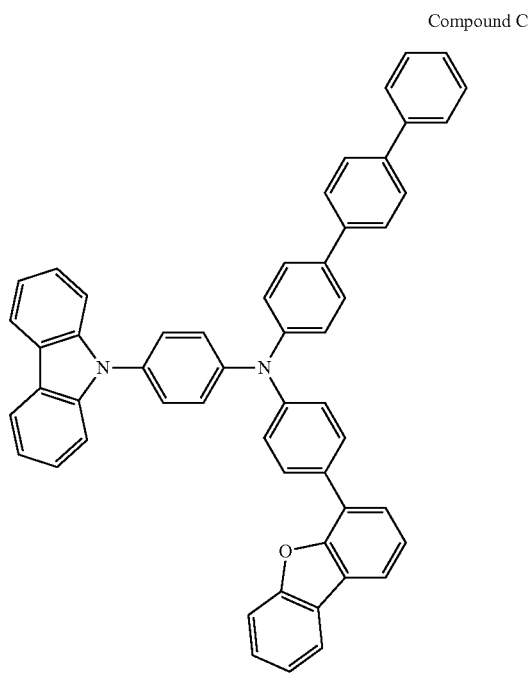

Experimental Example 1

Device Performance Analysis

Electroluminescent characteristics of the organic electroluminescent devices prepared in Examples and Comparative Examples were analyzed under a condition of 10 mA/cm². The life-span characteristics were measured using a time (LT95) (hr) consumed for a current luminance to reach 95% of an initial luminance under a constant current driving condition of 20 mA/cm². Results are shown in Table 1 below.

TABLE 1

| Examples | Hole transport auxiliary layer | V | Cd/A | lm/W | CIEx | CIEy | LT95 (hrs) |
|---|---|---|---|---|---|---|---|
| Example 1 | Compound 1 | 3.74 | 6.2 | 5.2 | 0.14 | 0.049 | 195 |
| Example 2 | Compound 2 | 3.89 | 6.2 | 5 | 0.14 | 0.046 | 165 |
| Example 3 | Compound 3 | 3.96 | 6.0 | 4.8 | 0.141 | 0.044 | 175 |
| Example 4 | Compound 4 | 3.85 | 6.5 | 5.3 | 0.139 | 0.048 | 155 |
| Example 5 | Compound 11 | 3.9 | 5.3 | 4.2 | 0.14 | 0.049 | 170 |
| Example 6 | Compound 15 | 3.93 | 6.9 | 5.5 | 0.142 | 0.045 | 190 |
| Example 7 | Compound 21 | 3.93 | 6.2 | 5.0 | 0.139 | 0.05 | 165 |
| Example 8 | Compound 26 | 3.88 | 6.0 | 4.9 | 0.141 | 0.049 | 195 |
| Example 9 | Compound 32 | 3.91 | 5.9 | 4.7 | 0.14 | 0.045 | 175 |
| Example 10 | Compound 43 | 4.05 | 6.1 | 4.7 | 0.142 | 0.046 | 180 |
| Example 11 | Compound 48 | 3.86 | 6.0 | 4.8 | 0.143 | 0.041 | 170 |
| Example 12 | Compound 49 | 3.88 | 5.9 | 4.7 | 0.143 | 0.141 | 190 |
| Example 13 | Compound 55 | 3.79 | 5.9 | 4.9 | 0.142 | 0.045 | 210 |
| Example 14 | Compound 59 | 3.80 | 6.2 | 5.1 | 0.14 | 0.046 | 175 |
| Example 15 | Compound 63 | 4.0 | 6.0 | 4.7 | 0.141 | 0.044 | 170 |
| Example 16 | Compound 118 | 3.95 | 6.0 | 4.8 | 0.143 | 0.041 | 150 |
| Comparative Example 1 | NPB | 4.21 | 5.6 | 4.2 | 0.139 | 0.05 | 80 |
| Comparative Example 2 | Compound A | 3.88 | 5.8 | 4.7 | 0.14 | 0.049 | 96 |
| Comparative Example 3 | Compound B | 4.05 | 5.7 | 4.8 | 0.141 | 0.047 | 120 |
| Comparative Example 4 | Compound C | 3.96 | 6.0 | 4.8 | 0.142 | 0.047 | 125 |

As evident from the above table 1, the efficiency of the organic electroluminescent devices prepared in Examples 1 to 16 were equivalent to that of the organic electroluminescent devices prepared in Comparative Examples 1 to 4. The lifetimes of the organic electroluminescent devices prepared in Examples 1 to 16 were increased by about 100% compared to the lifespans of the organic electroluminescent devices prepared in Comparative Examples 1 to 4.

As described above, the present disclosure is described with reference to the drawings. However, the present disclosure is not limited by the embodiments and drawings disclosed in the present specification. It will be apparent that various modifications may be made thereto by those skilled in the art within the scope of the present disclosure. Furthermore, although the effect resulting from the features of the present disclosure has not been explicitly described in the description of the embodiments of the present disclosure, it is obvious that a predictable effect resulting from the features of the present disclosure should be recognized.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An organic electroluminescent device, comprising:
a first electrode;
a second electrode; and
at least one organic layer between the first electrode and the second electrode, the at least one organic layer including a light emission layer, and a hole transport layer and a hole transport auxiliary layer between the first electrode and the light emission layer,
wherein the hole transport auxiliary layer includes a compound represented by the following Chemical Formula 1:

Chemical Formula 1

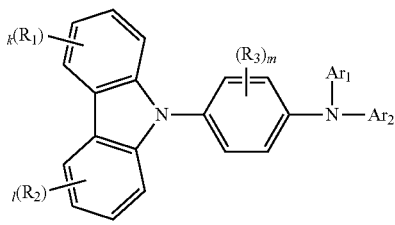

Ar₁ is represented by the following Chemical Formula 2:

Chemical Formula 2

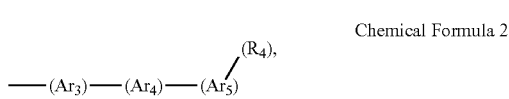

Ar₂ is represented by the following Chemical Formula 3:

Chemical Formula 3

wherein:
each of $Ar_3$ to $Ar_7$ is independently a substituted or unsubstituted C3 to C30 aryl group, and at least one of $Ar_3$ to $Ar_7$ represents a substituted or unsubstituted C8 to C30 aryl group,
each of $R_1$ to $R_5$ is independently selected from the group consisting of hydrogen, deuterium, substituted or unsubstituted C1 to C30 alkyl, substituted or unsubstituted C3 to C30 cycloalkyl, substituted or unsubstituted C6 to C30 aryl, and substituted or unsubstituted C2 to C30 heteroaryl, and
each of k, l and m is independently an integer of 0 to 4,
wherein the at least one organic layer further includes at least one layer selected from the group consisting of a hole injection layer, an electron transport auxiliary layer, an electrode transport layer and an electron injection layer, and
wherein the organic electroluminescent device further comprises a driving thin film transistor including an active layer electrically connected to the first electrode.

2. The organic electroluminescent device of claim 1, further comprising a first passivation film on the second electrode, and a second passivation film on the first passivation film.

3. The organic electroluminescent device of claim 2, wherein the first passivation film is over an entirety of the at least one organic layer and the second electrode.

4. The organic electroluminescent device of claim 2, further comprising an encapsulation film on the second passivation film, wherein the encapsulation film is bonded to the second passivation film via an adhesive film.

5. The organic electroluminescent device of claim 1, wherein the active layer includes an oxide semiconductor material.

6. The organic electroluminescent device of claim 1, wherein the driving thin film transistor includes:
a gate insulating film on the active layer; and
a gate electrode on the gate insulating film.

7. The organic electroluminescent device of claim 1, wherein each of $Ar_3$ to $Ar_7$ is independently a substituted or unsubstituted C8 to C30 condensed polycyclic group.

8. The organic electroluminescent device of claim 1, wherein each of $Ar_3$ to $Ar_7$ is independently substituted or unsubstituted naphthylene, substituted or unsubstituted phenanthrene, substituted or unsubstituted anthracene, or substituted or unsubstituted pyrene.

9. The organic electroluminescent device of claim 1, wherein the compound represented by Chemical Formula 1 is represented by one of the following compounds:

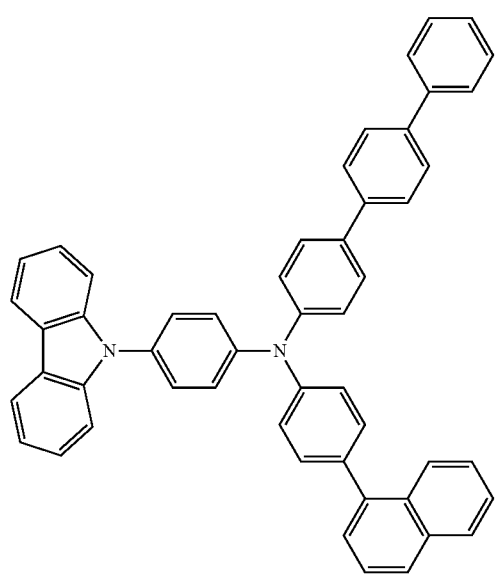

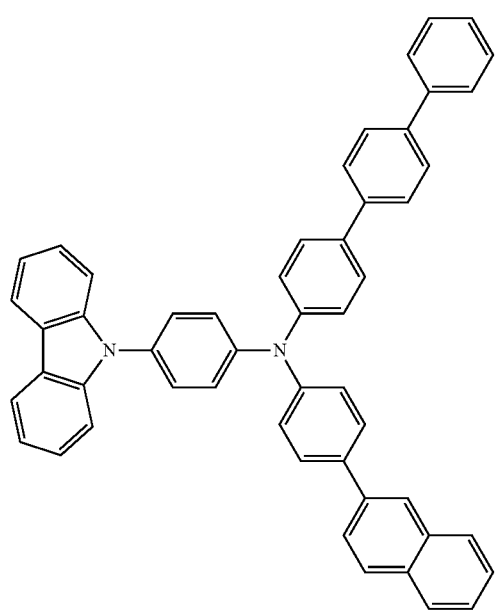

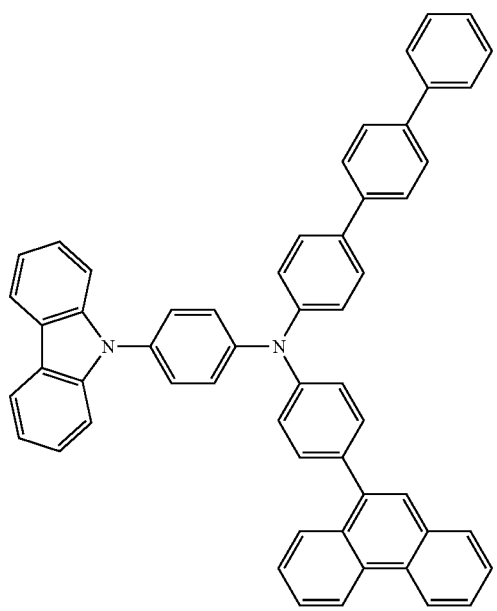
3
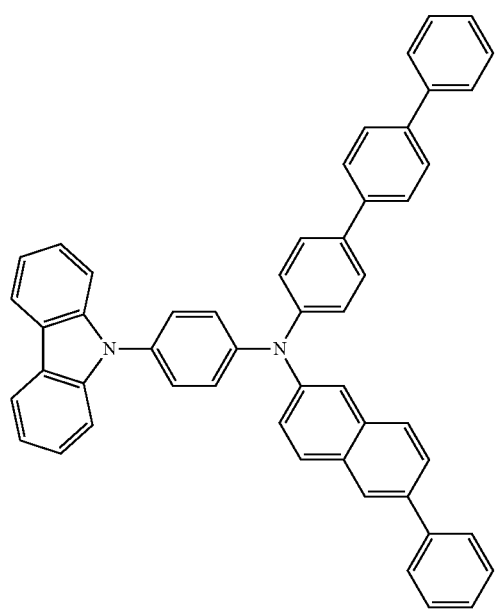
5
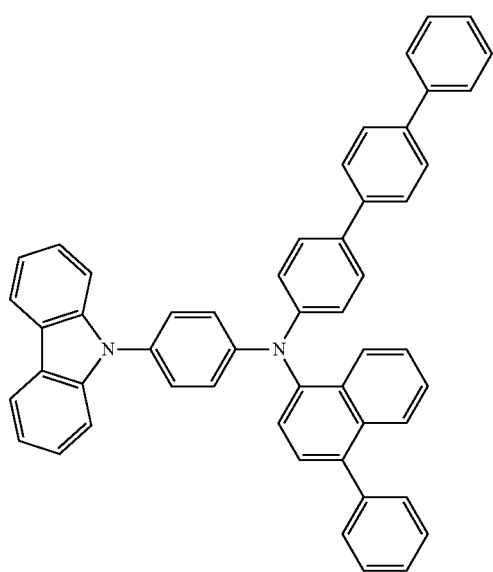
4
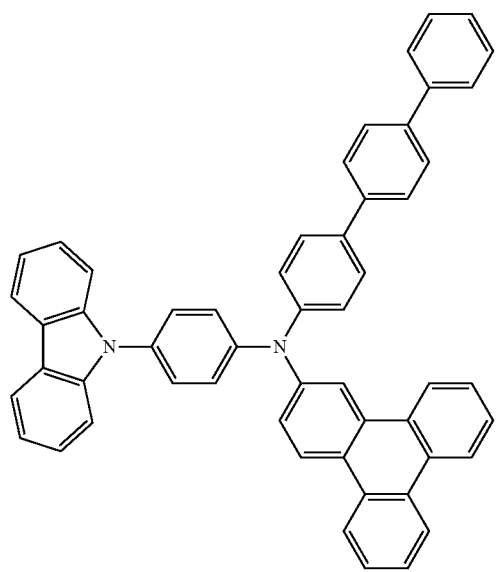
6

111
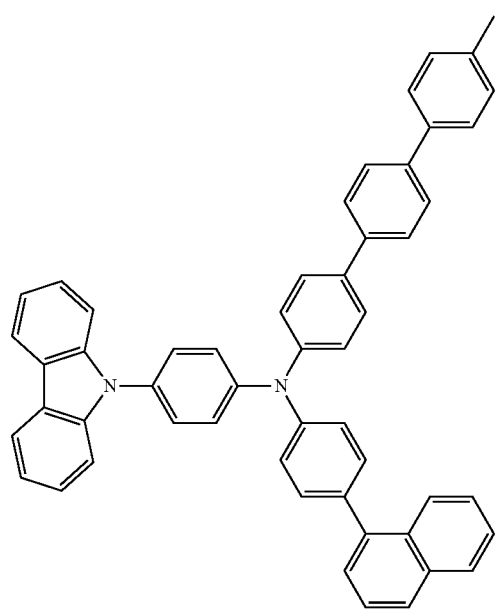
7
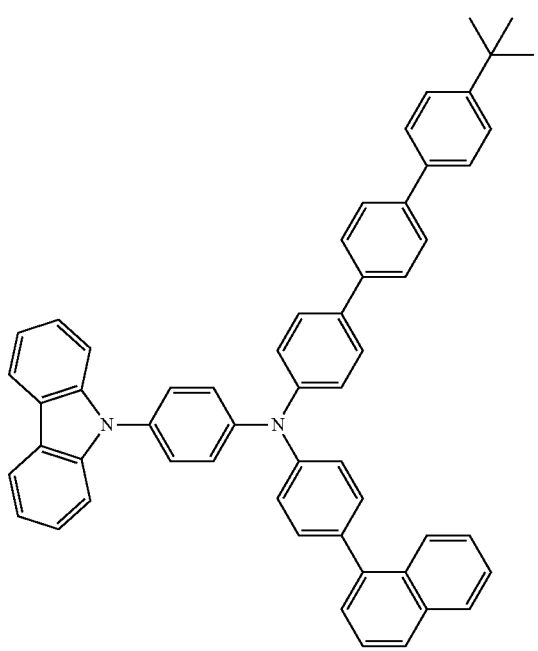
8
112
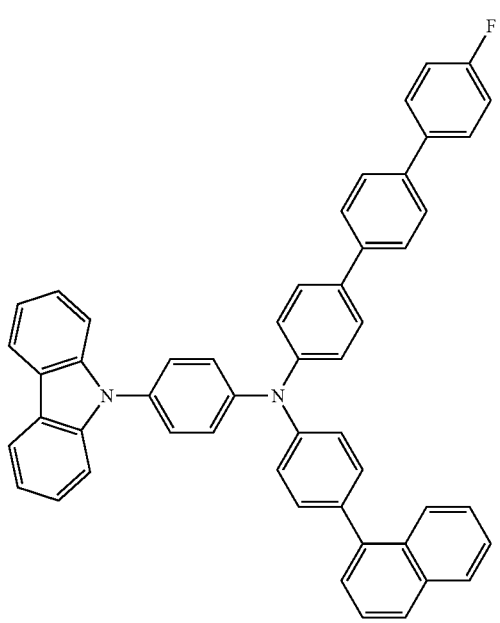
9
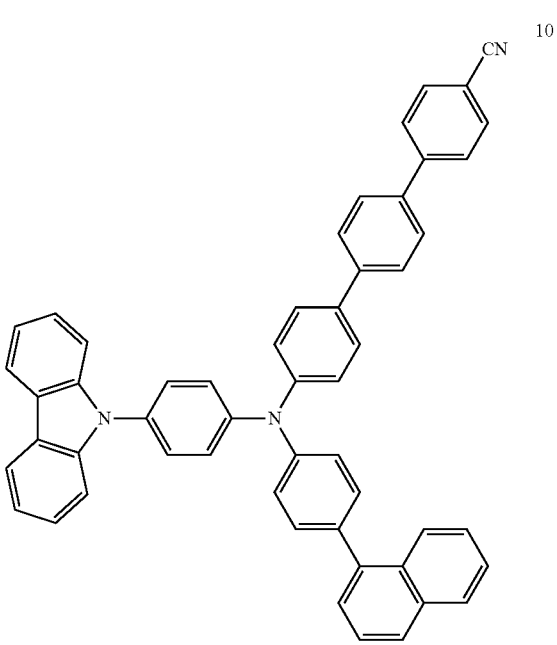
10

11
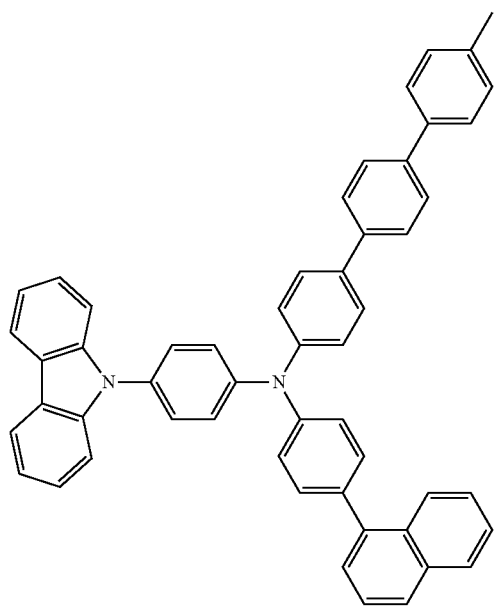
12
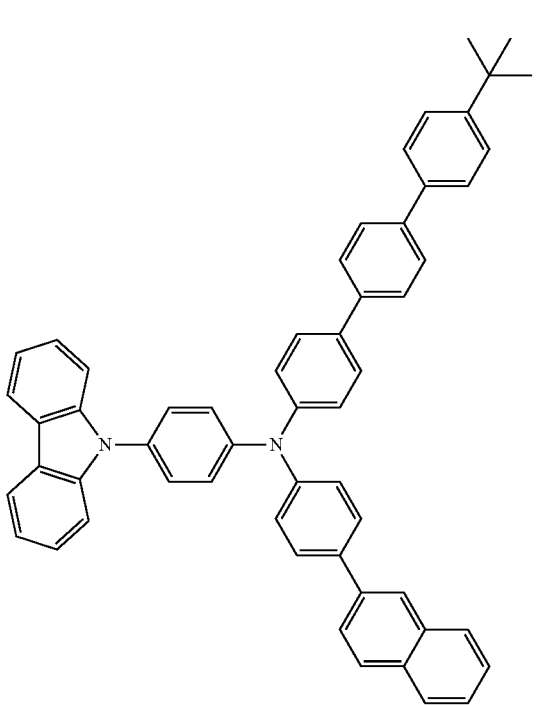
13
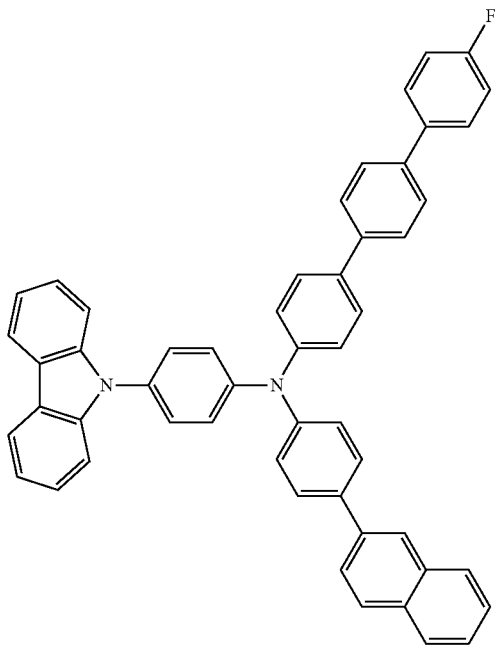
14
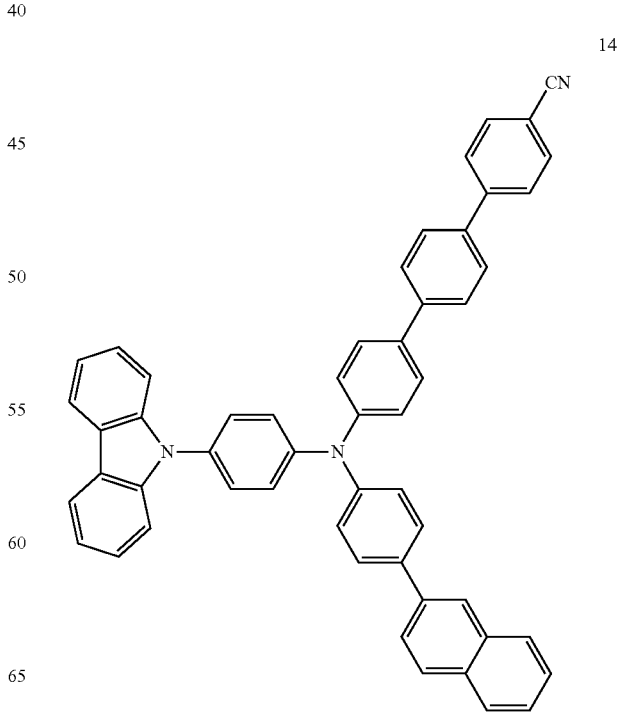

15
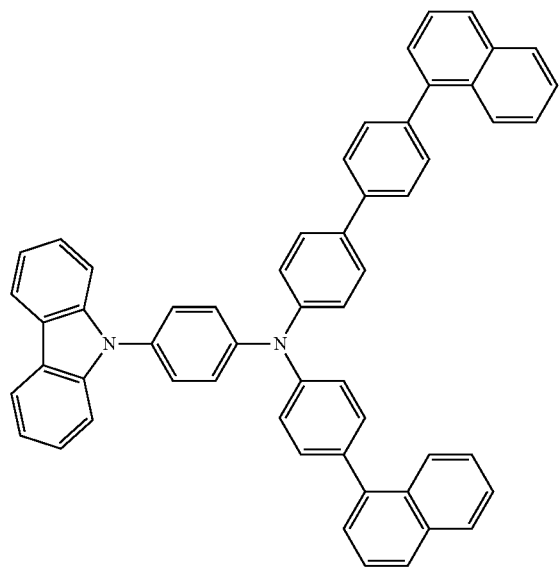
16
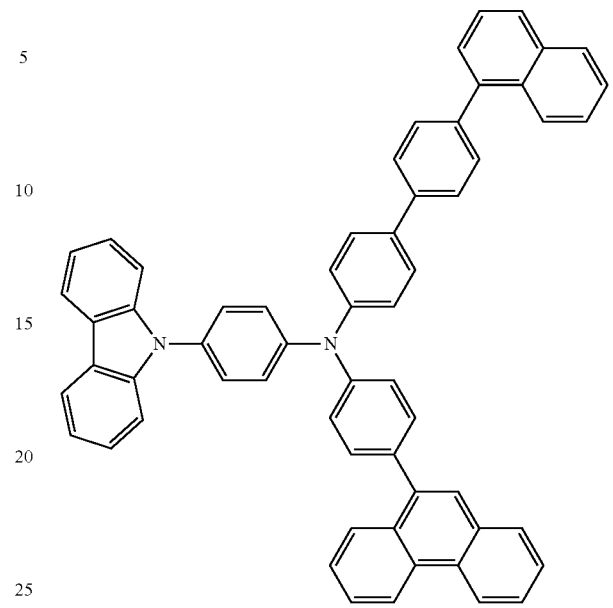
17
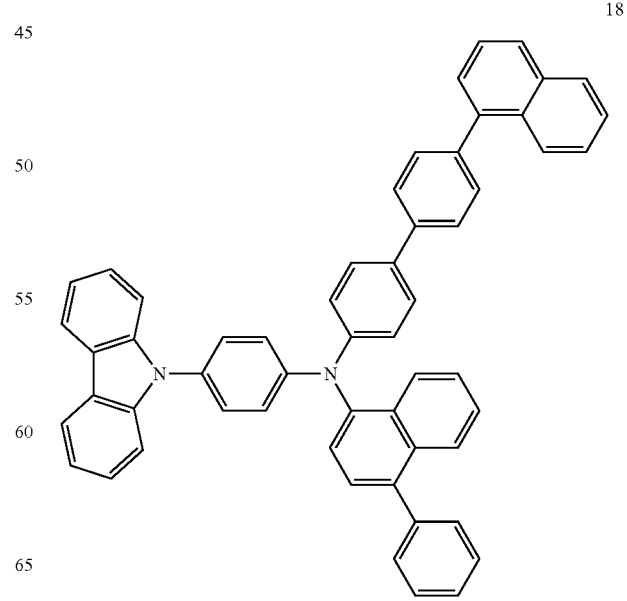
18

19
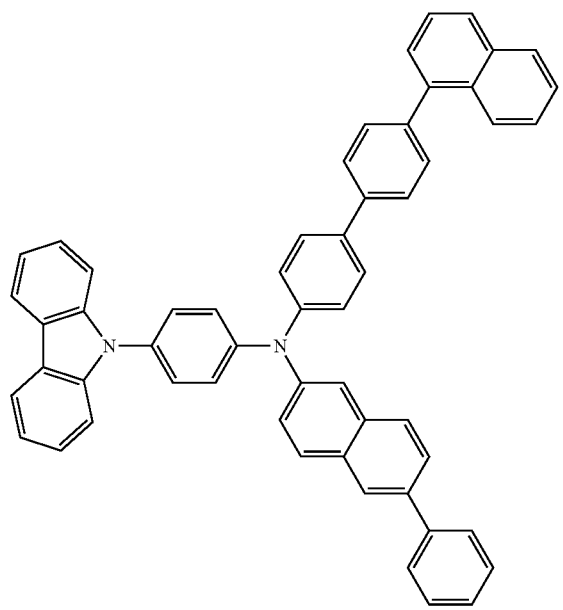
20
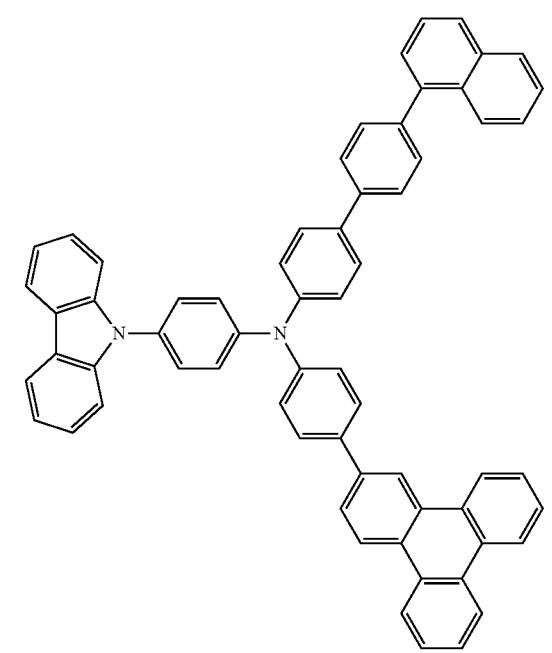
21
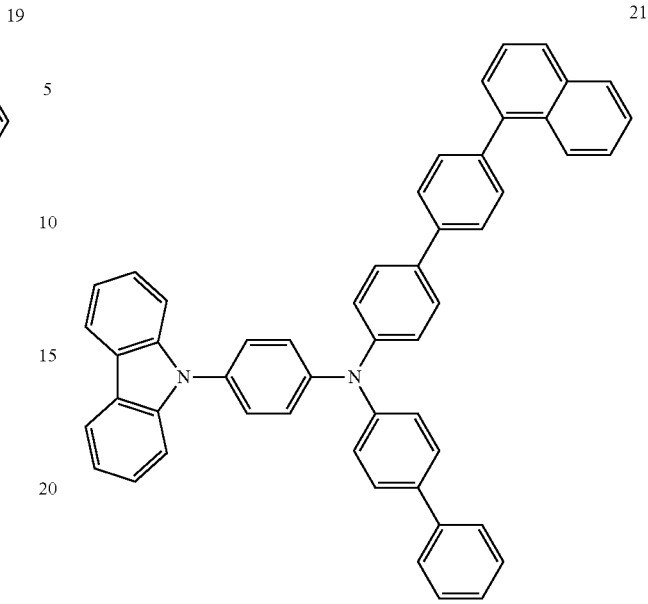
22
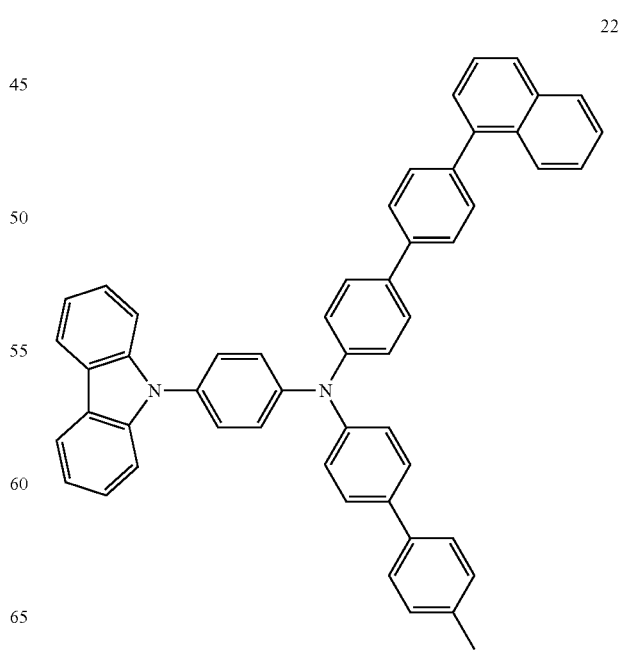

119
23
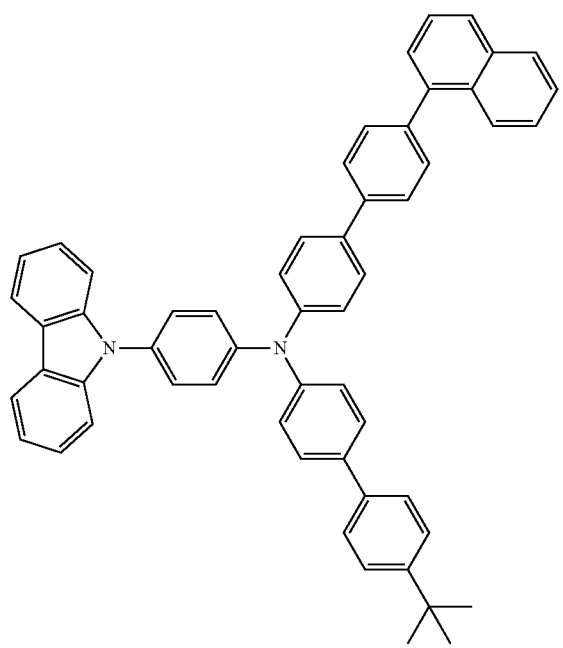
120
25
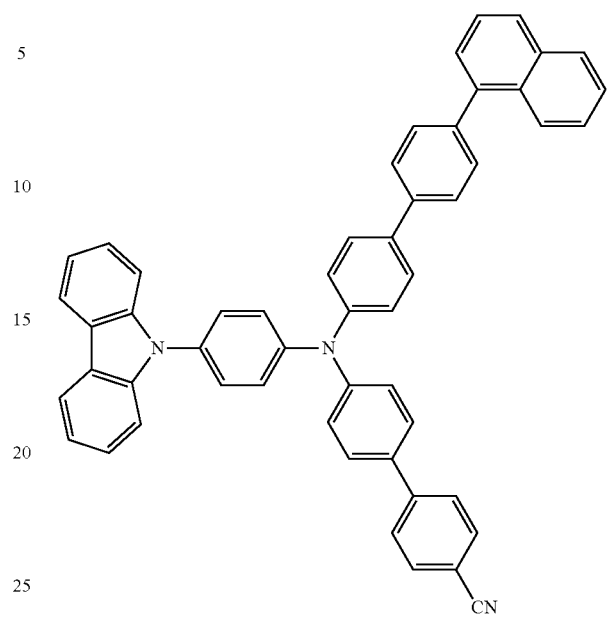
24
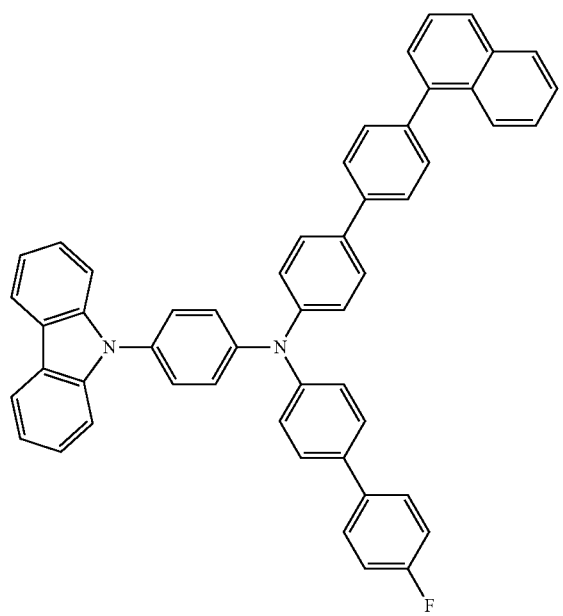
26

27
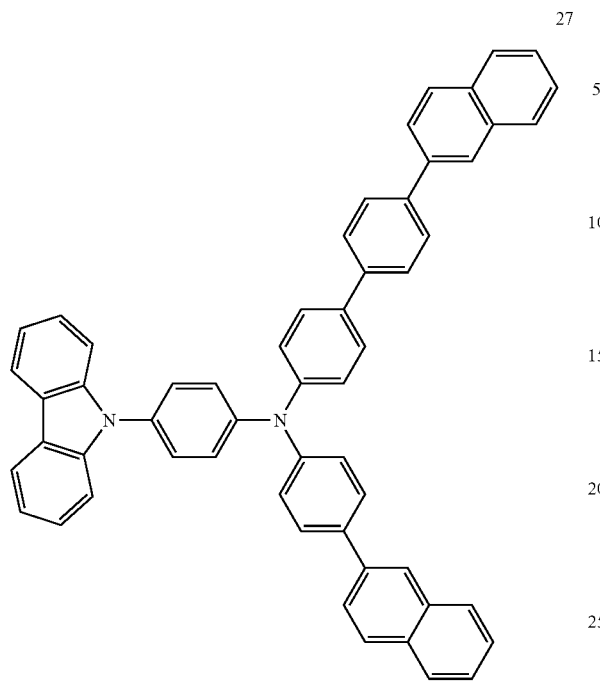
29
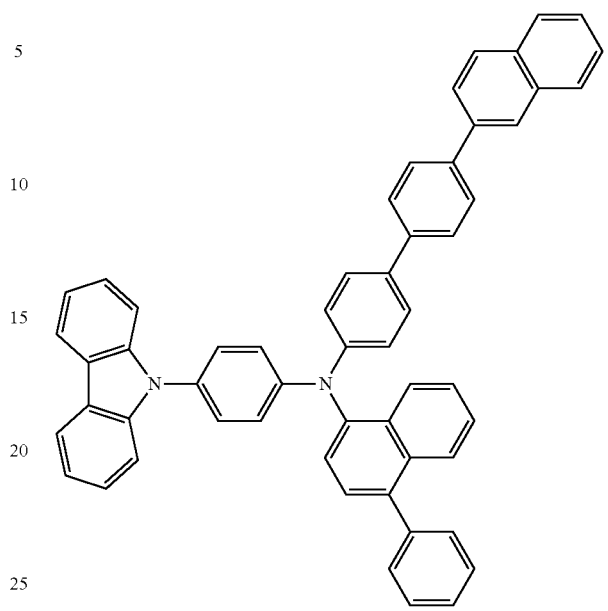
28
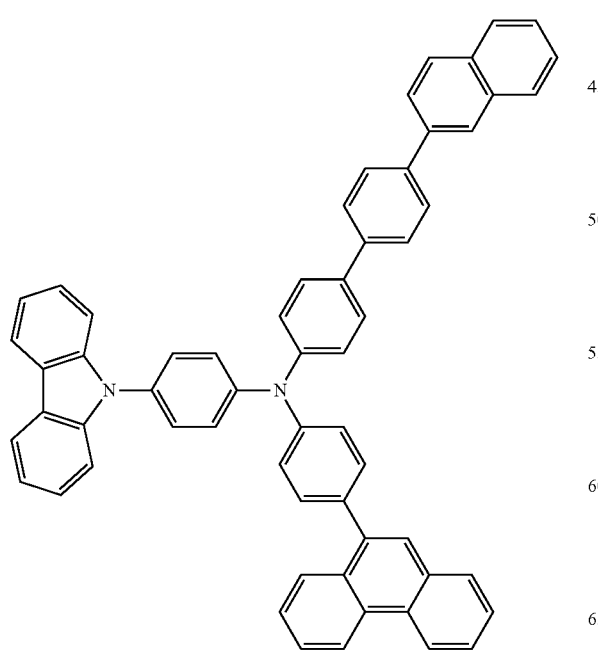
30
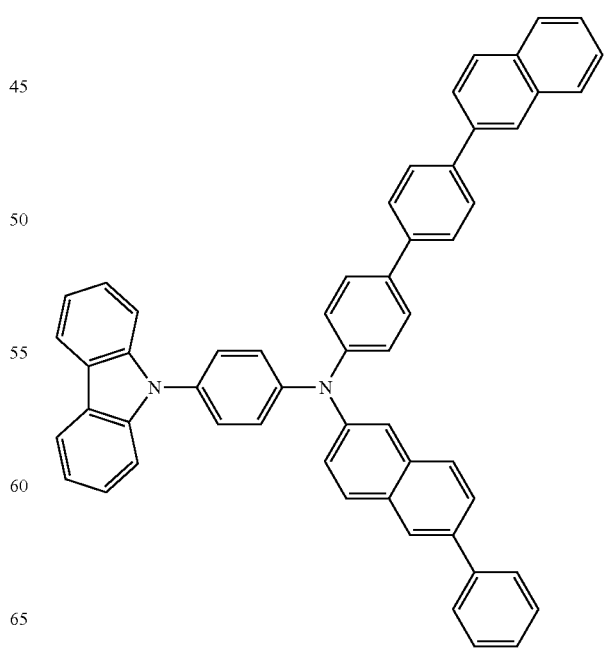

123
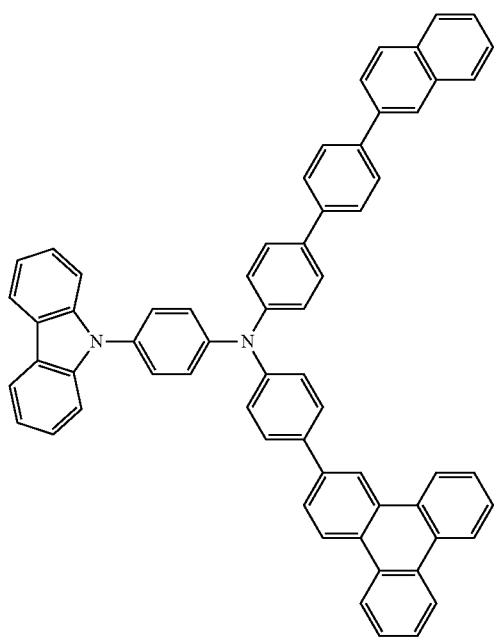
31
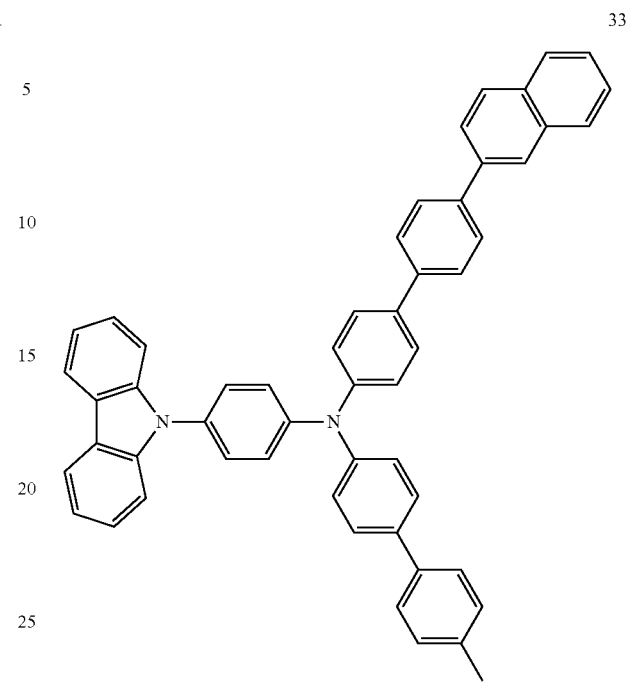
33
124
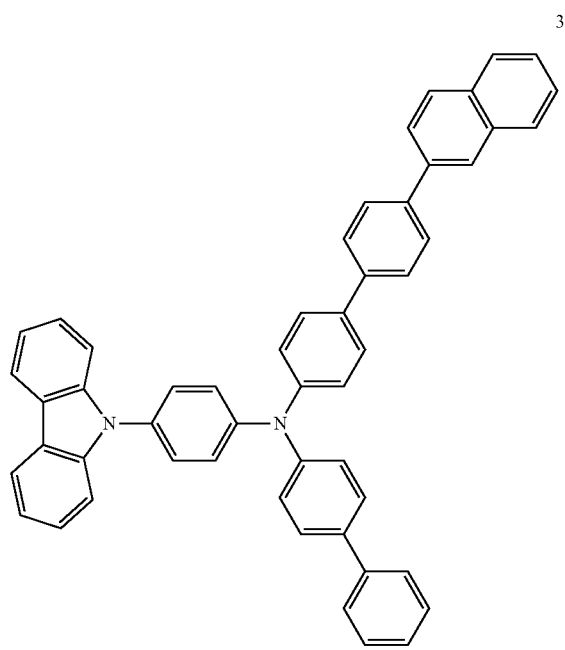
32
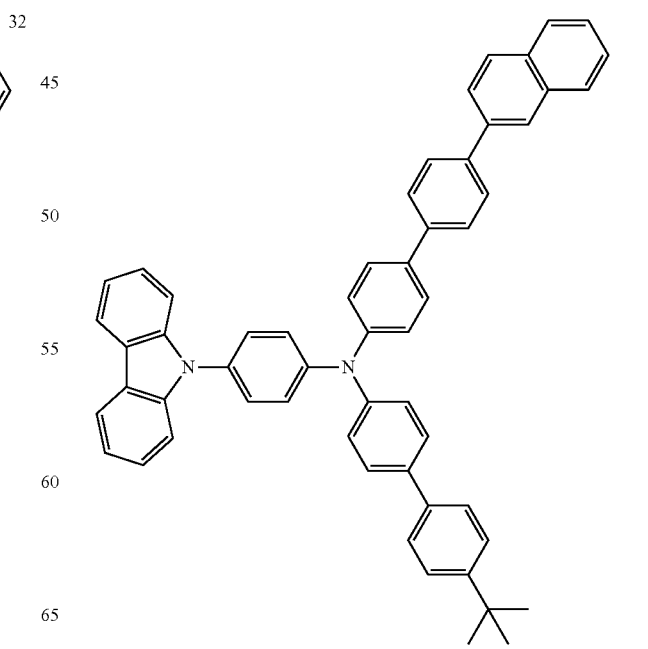
34

35
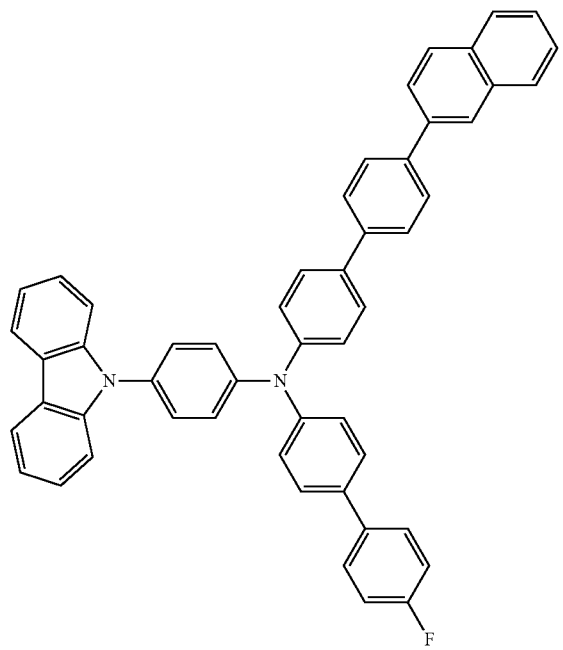
36
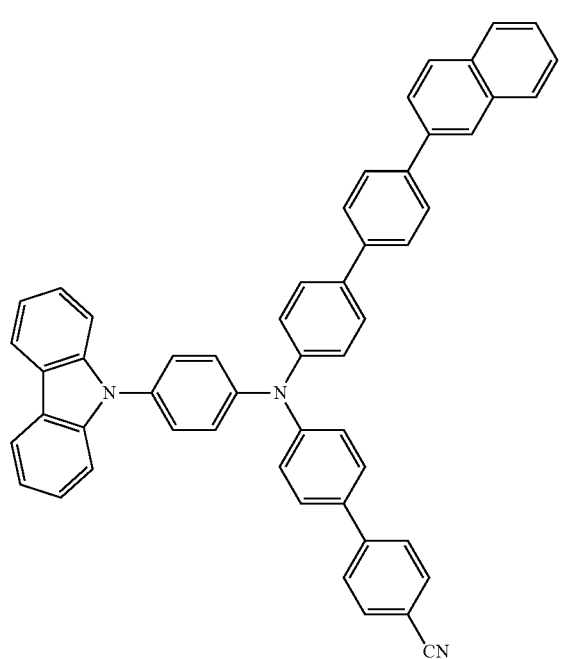
37
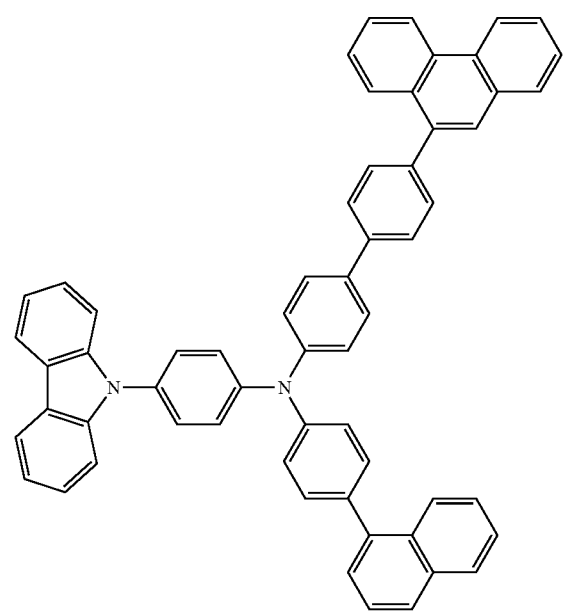
38
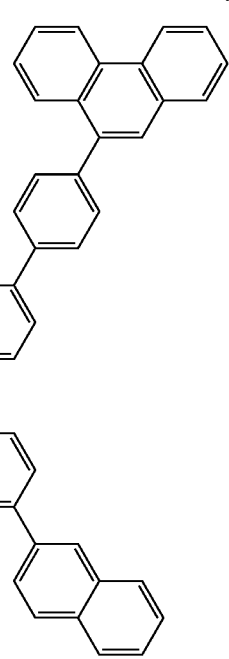

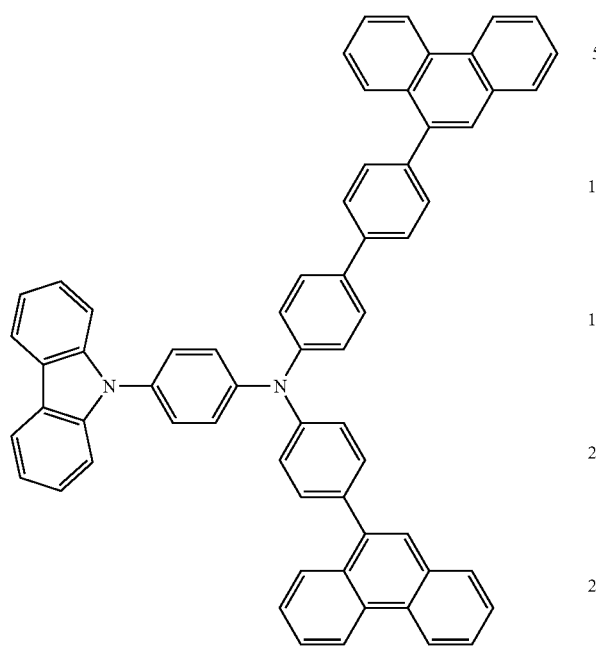
39
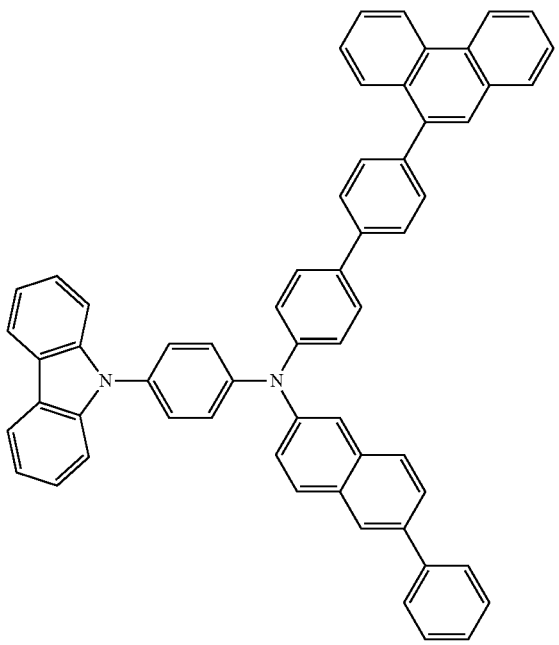
41
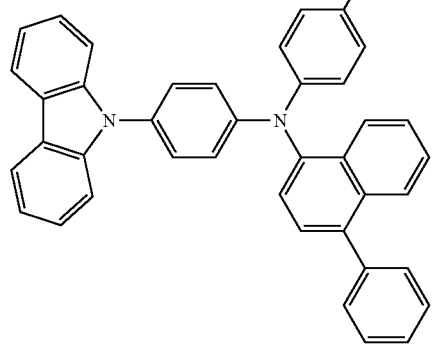
40
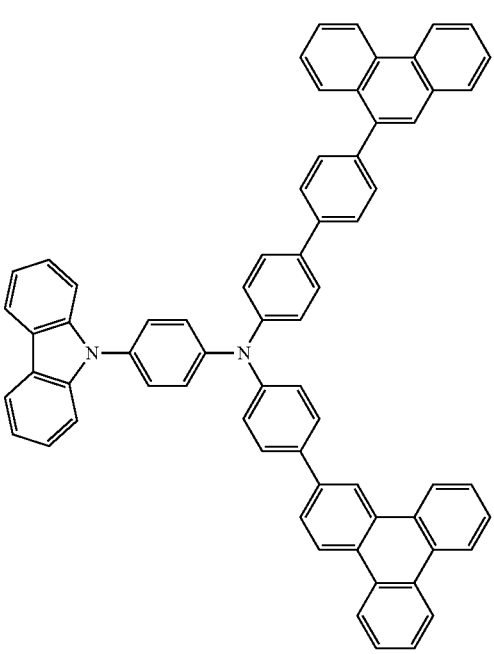
42

43
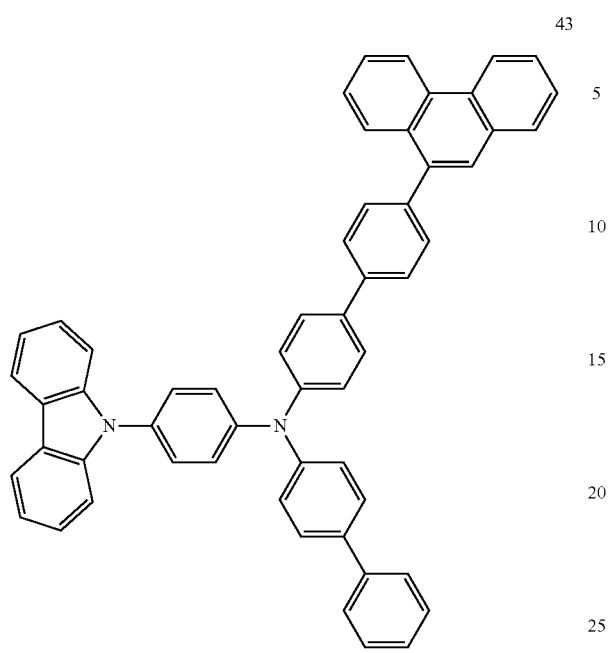
44
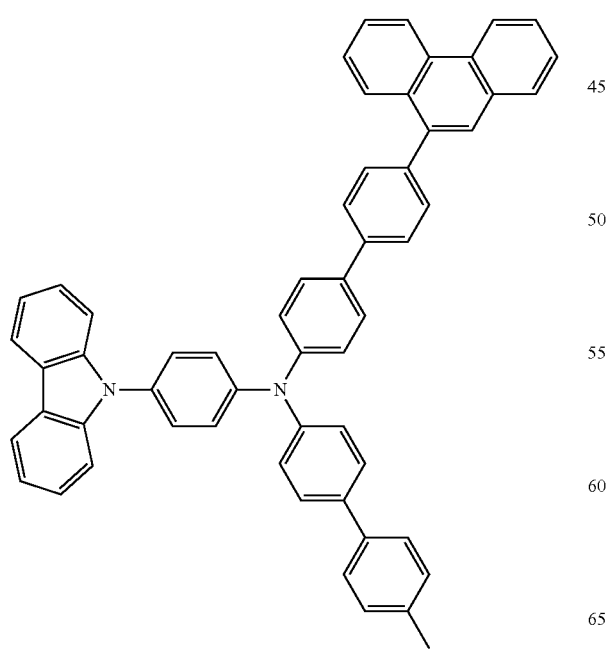
45
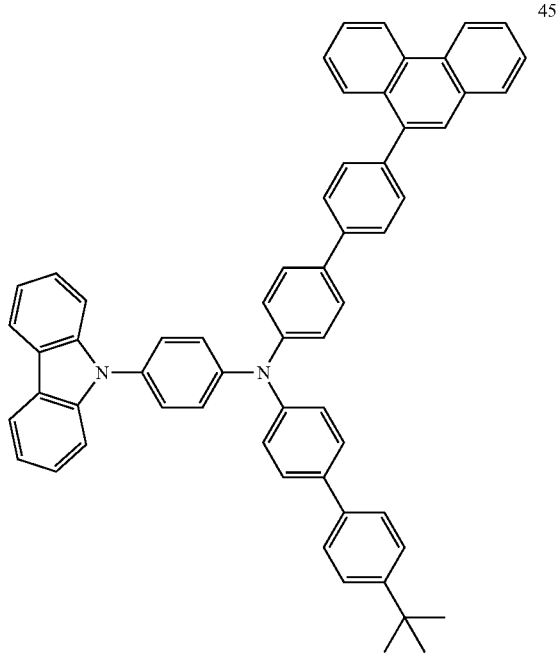
46
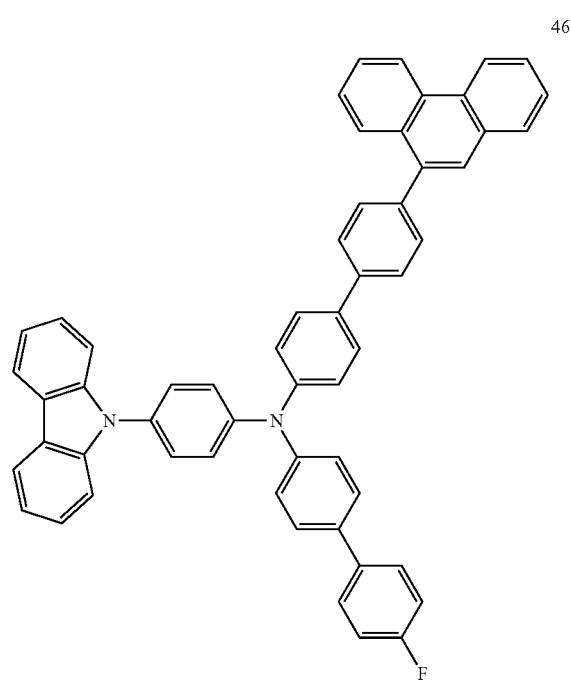

131
-continued
47
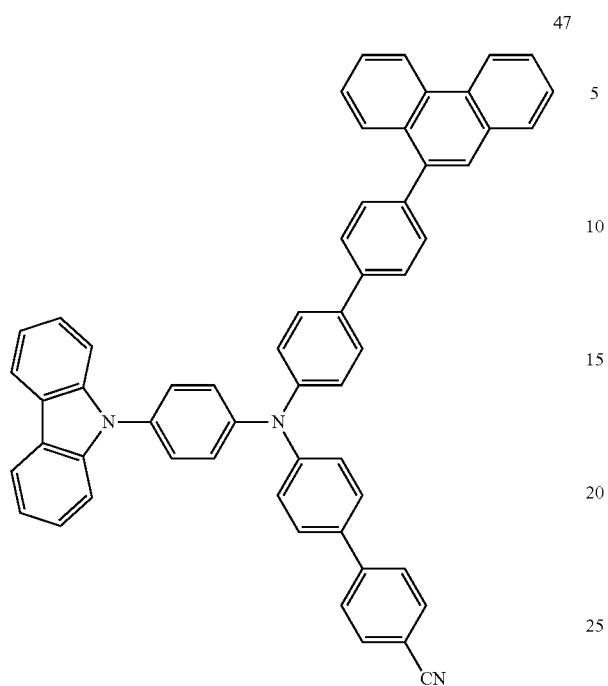
48
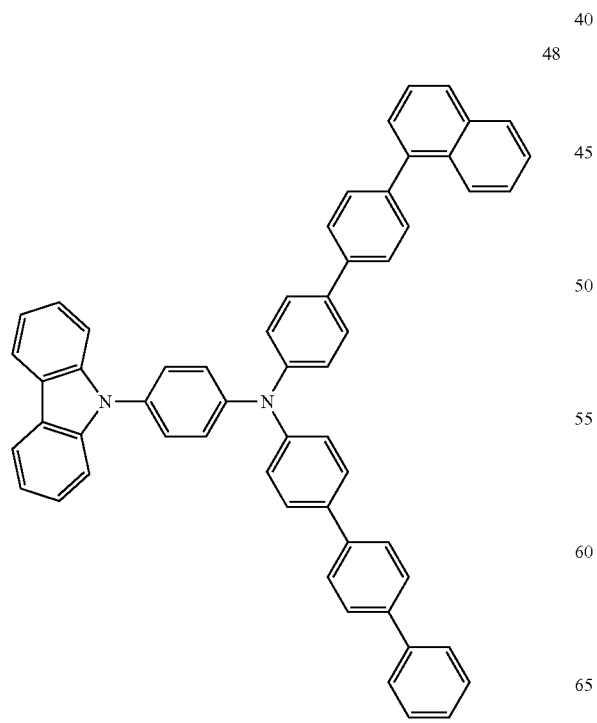
132
-continued
49
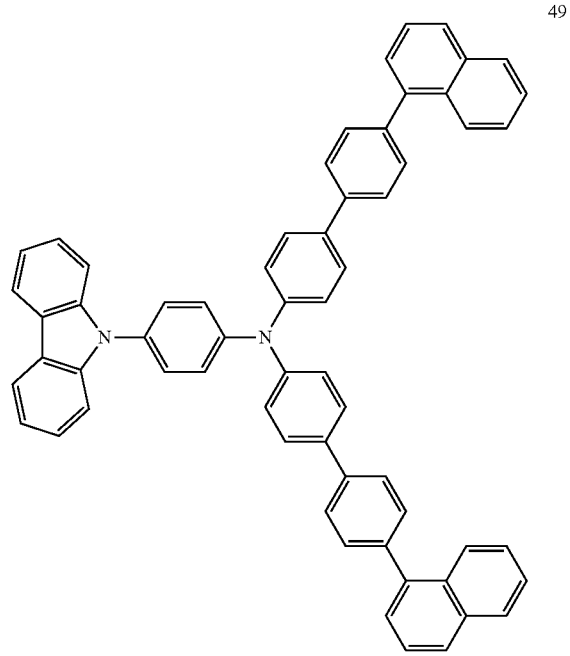
50

51
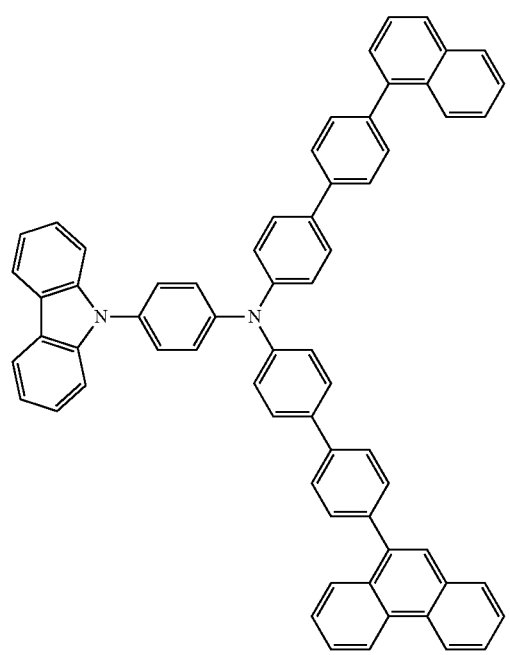
53
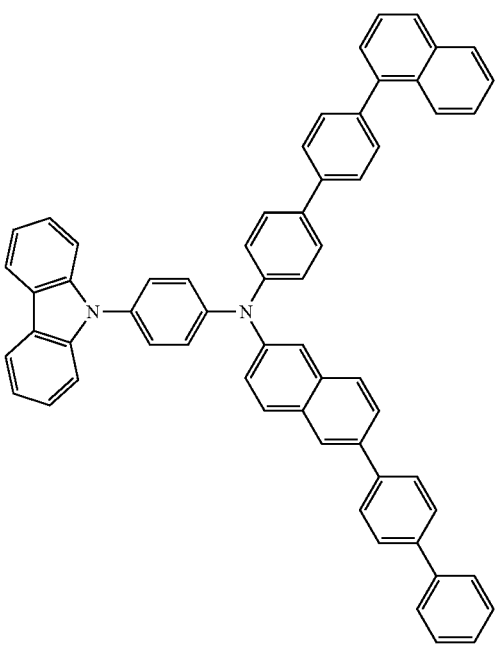
52
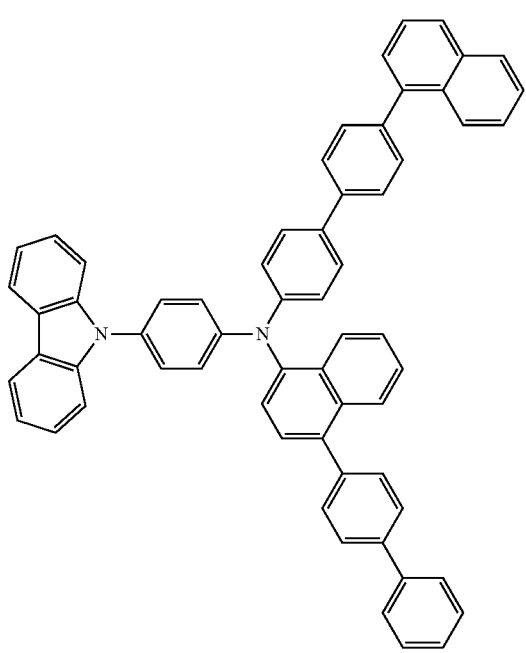
54
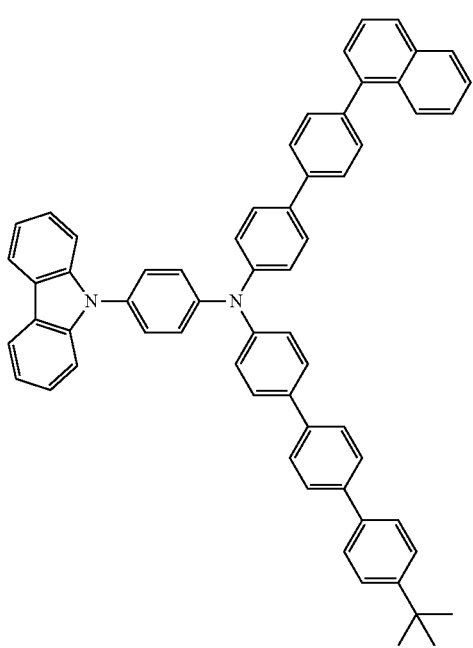

55
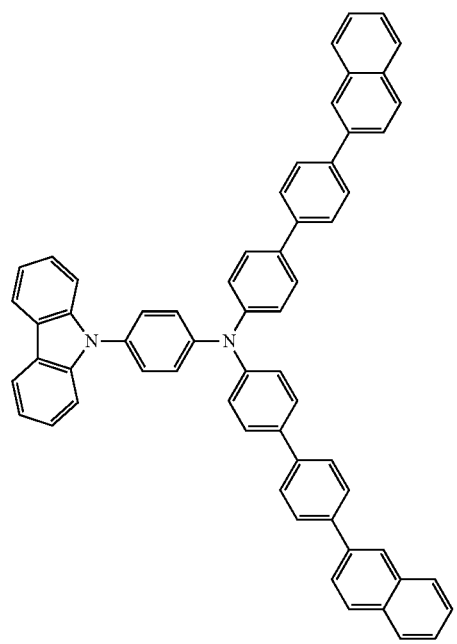
56
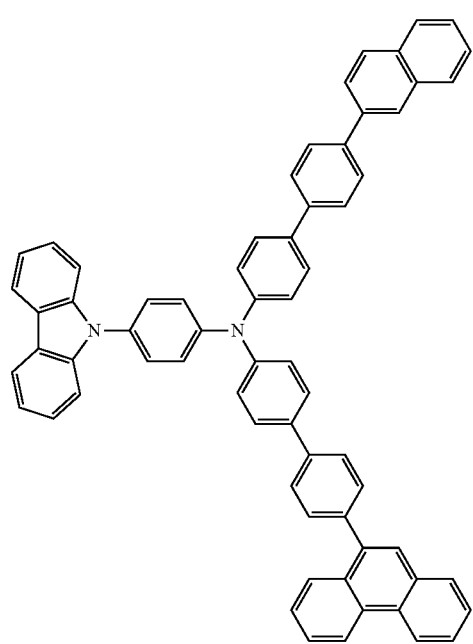
57
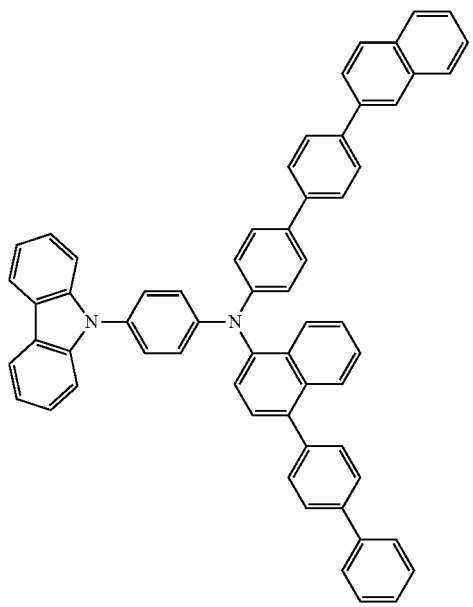
58
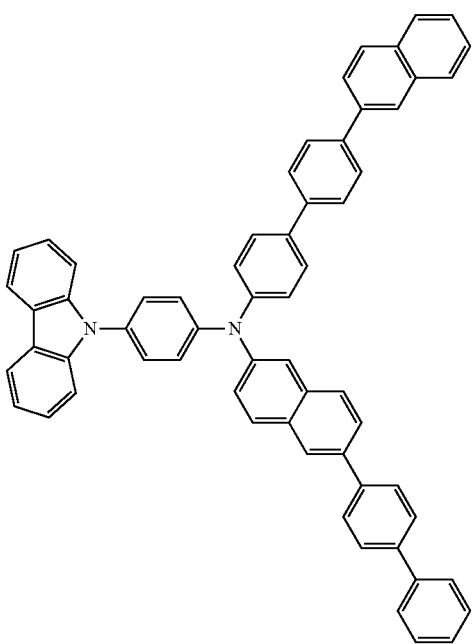

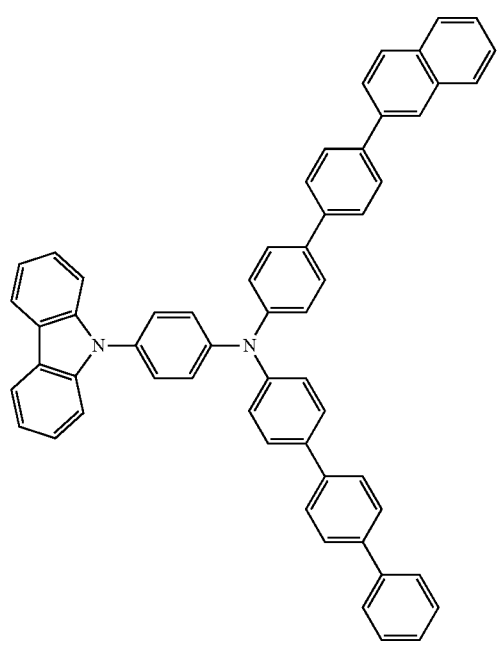
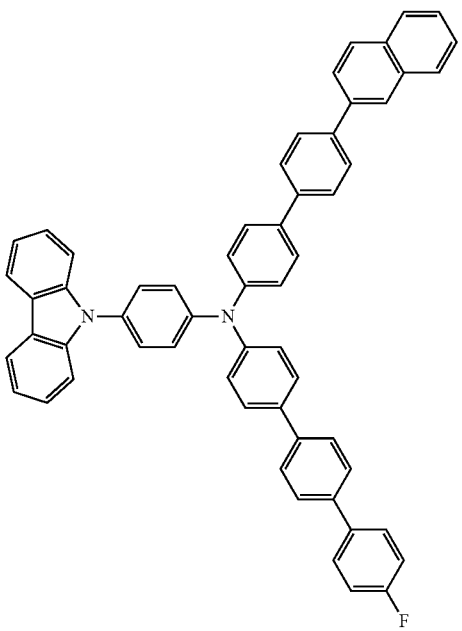
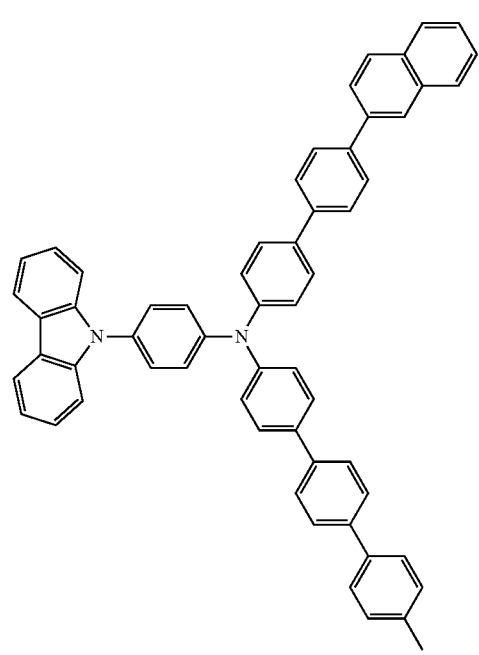
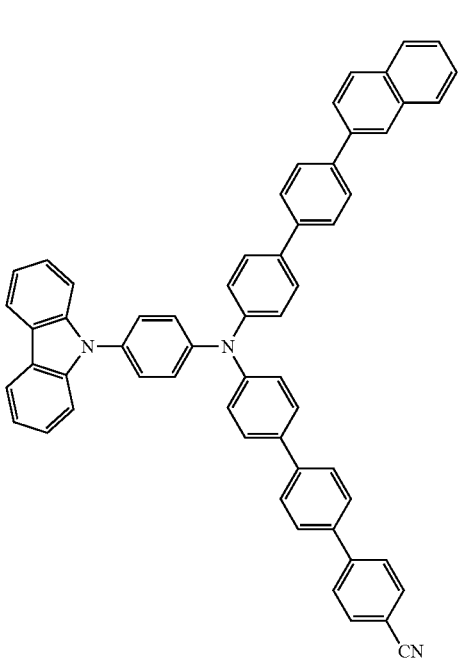

139
-continued
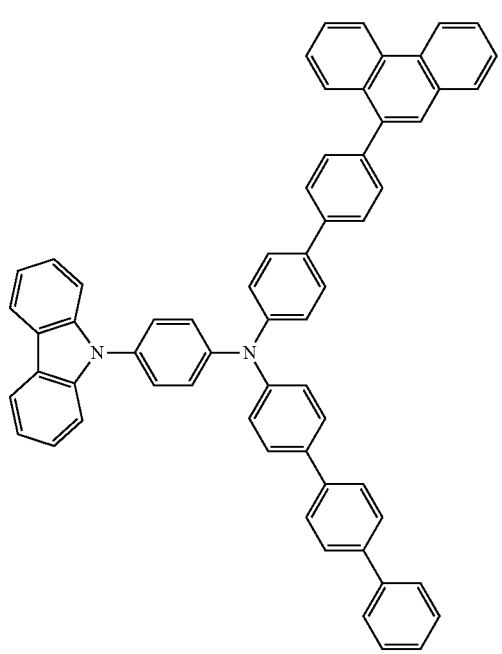
63
140
-continued
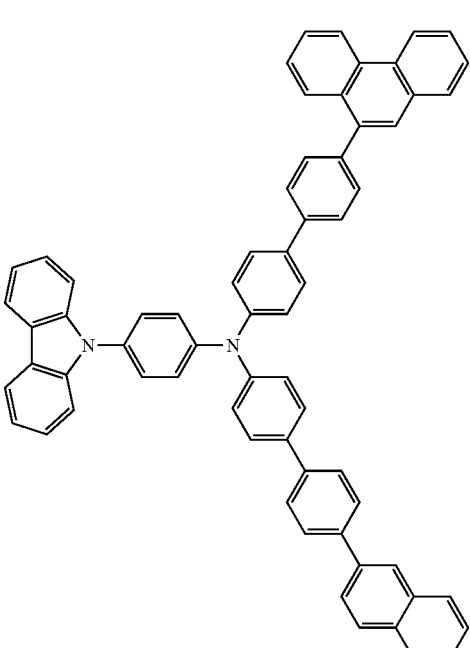
65
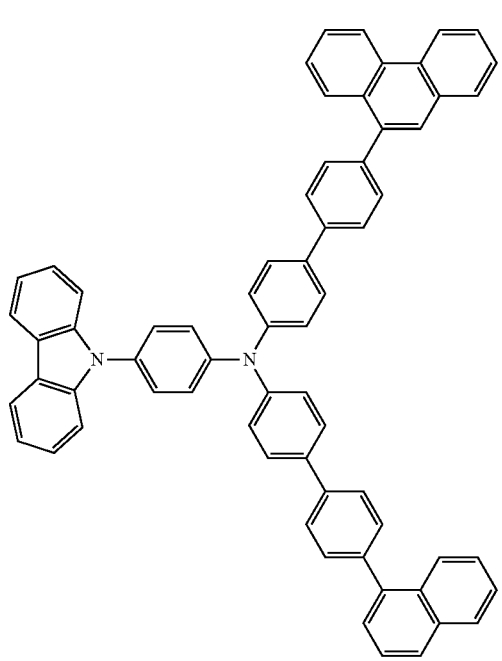
64
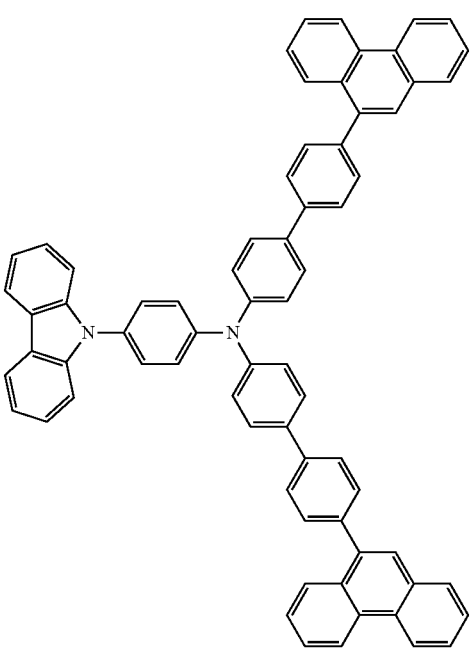
66

-continued
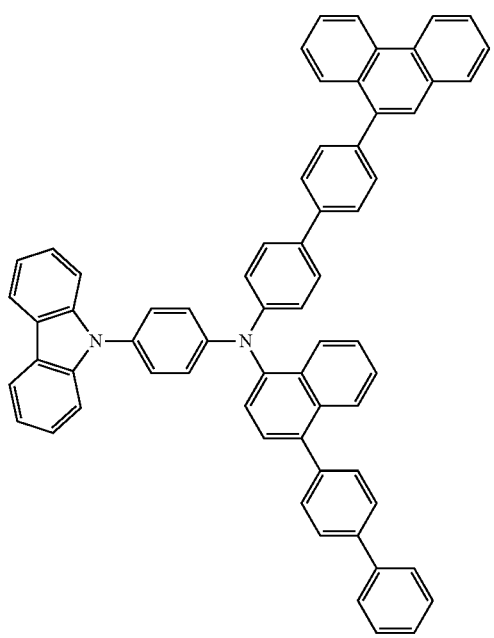
67
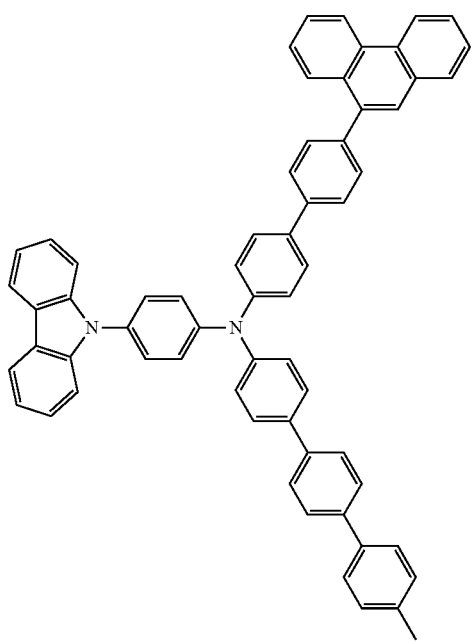
69
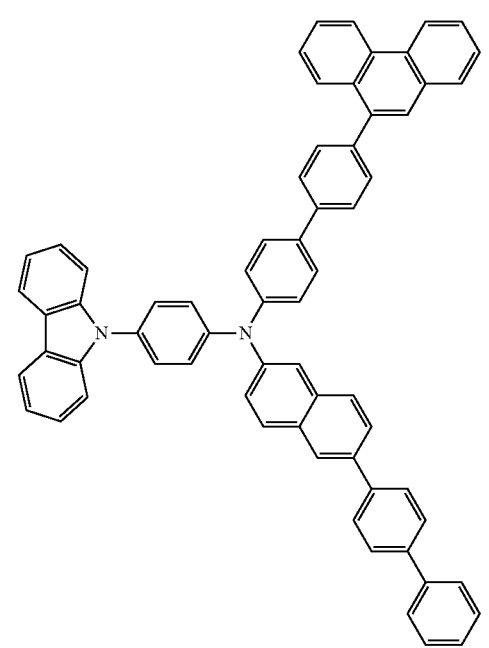
68
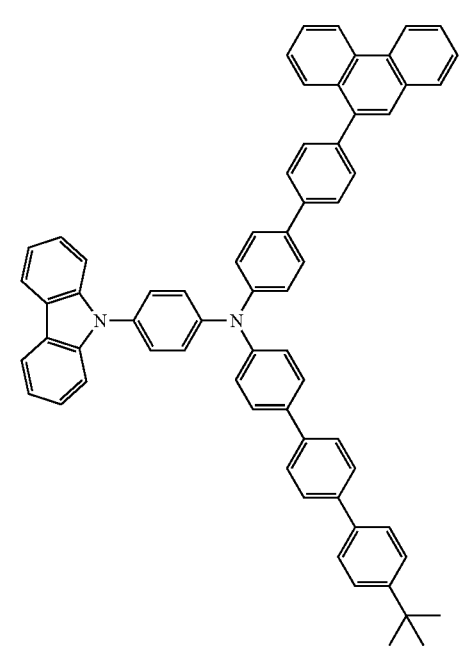
70

71
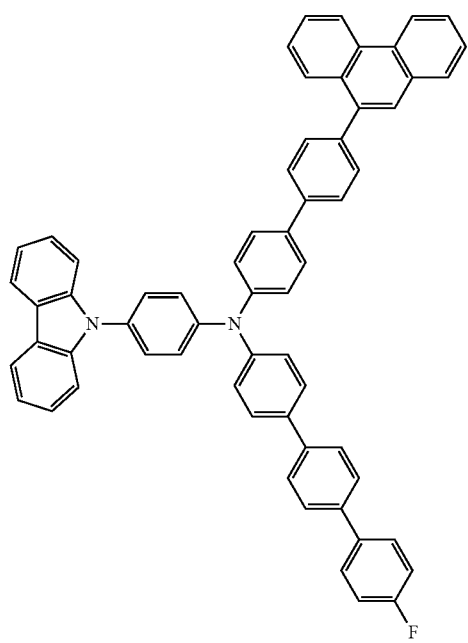
73
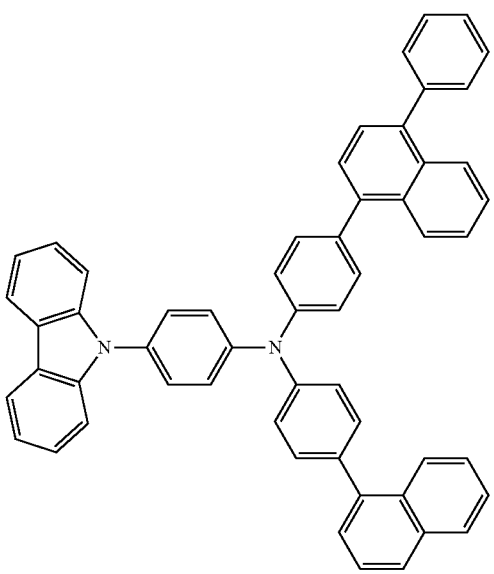
72
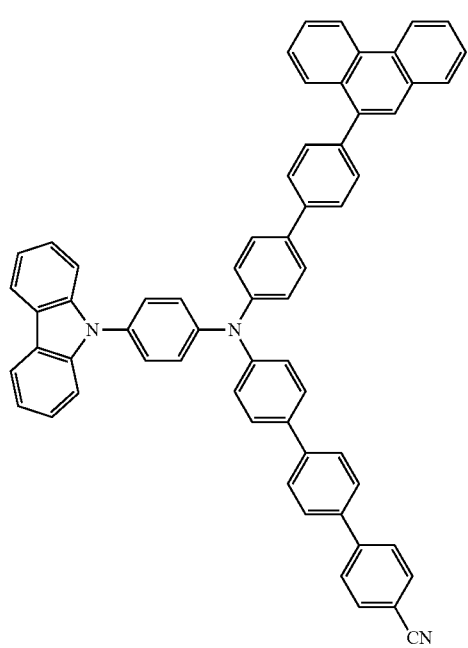
74
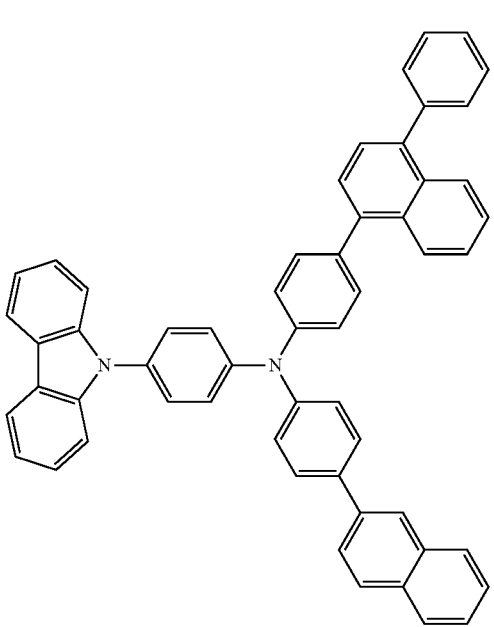

75
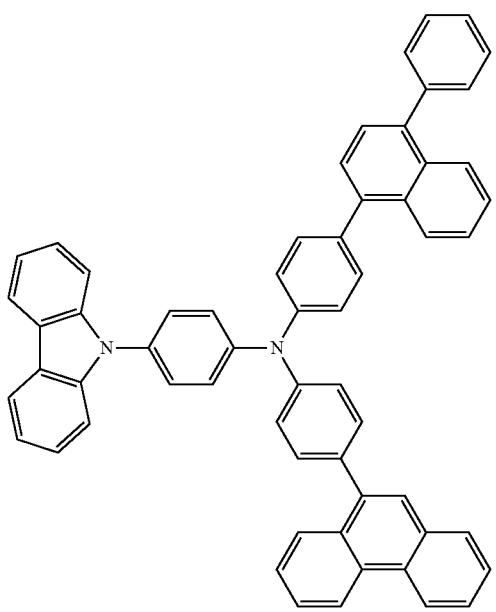
76
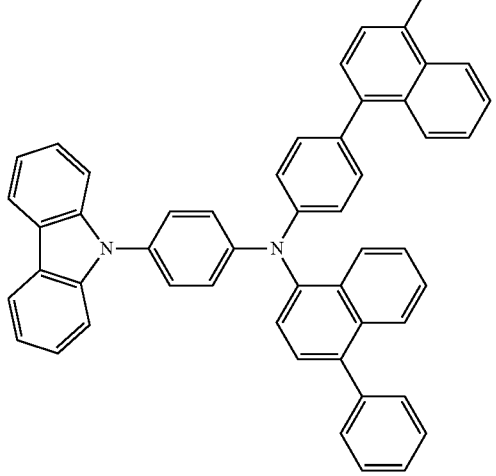
77
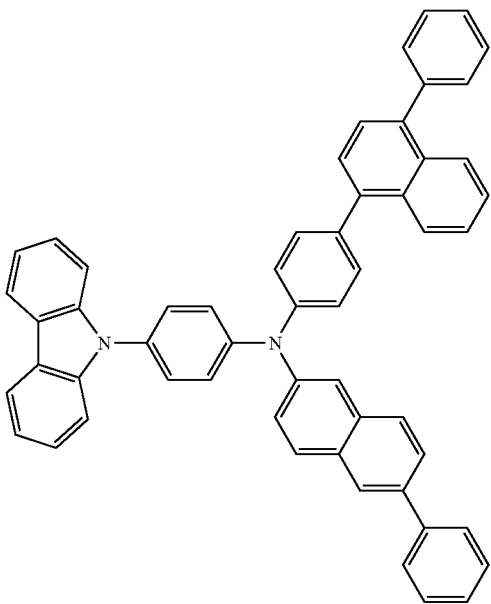
78
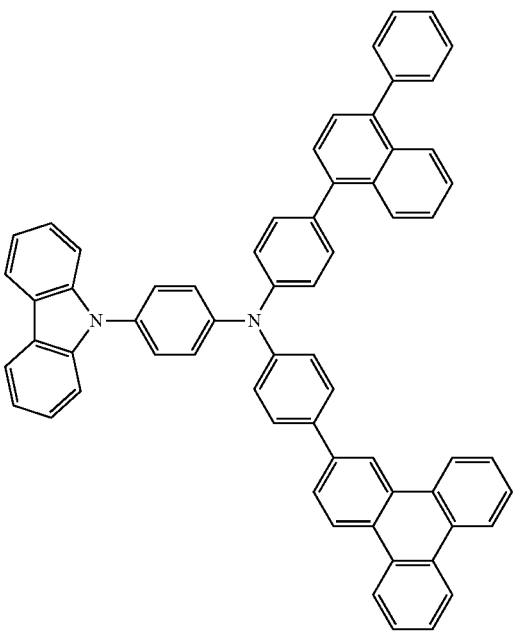

79
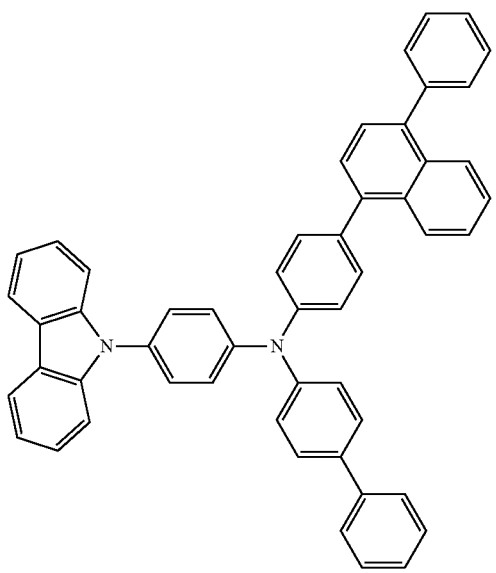
80
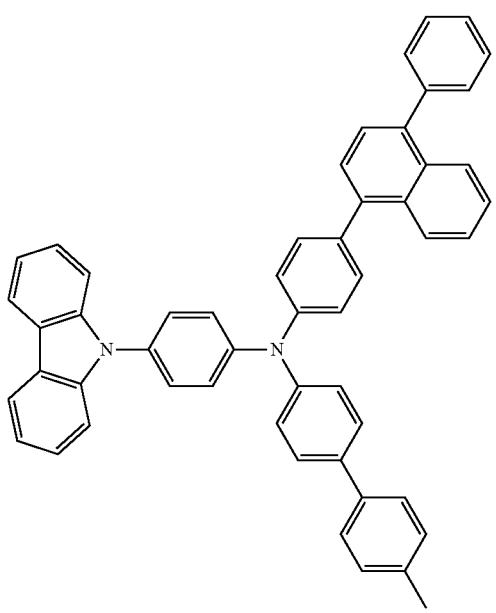
81
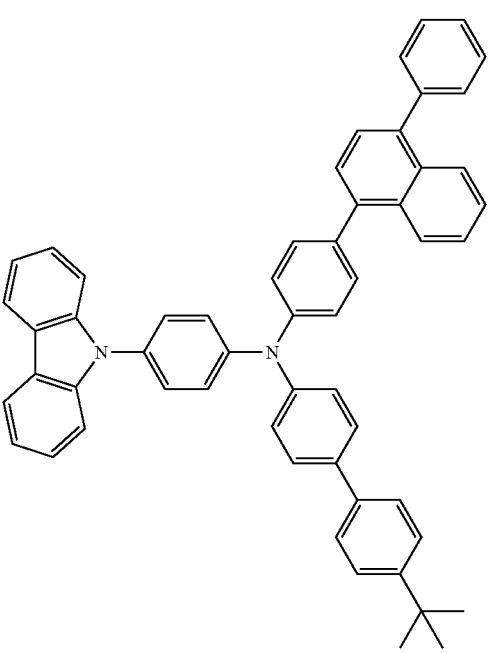
82
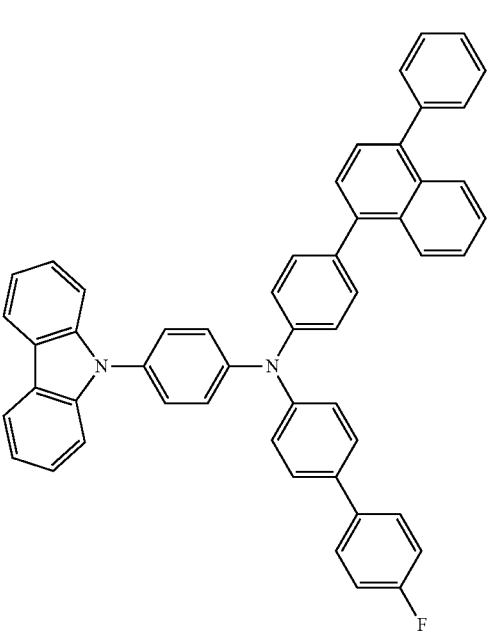

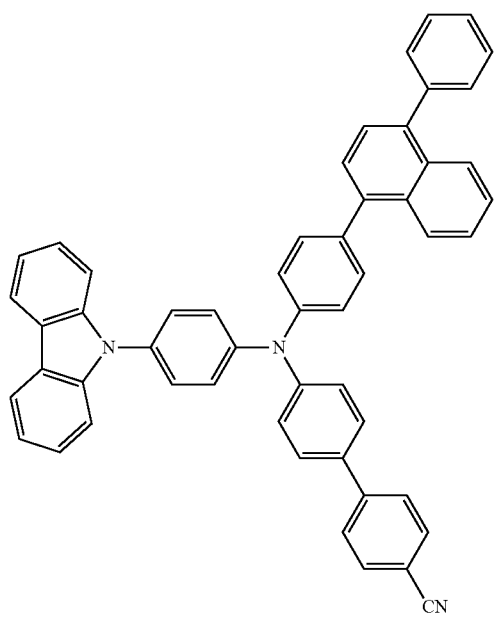
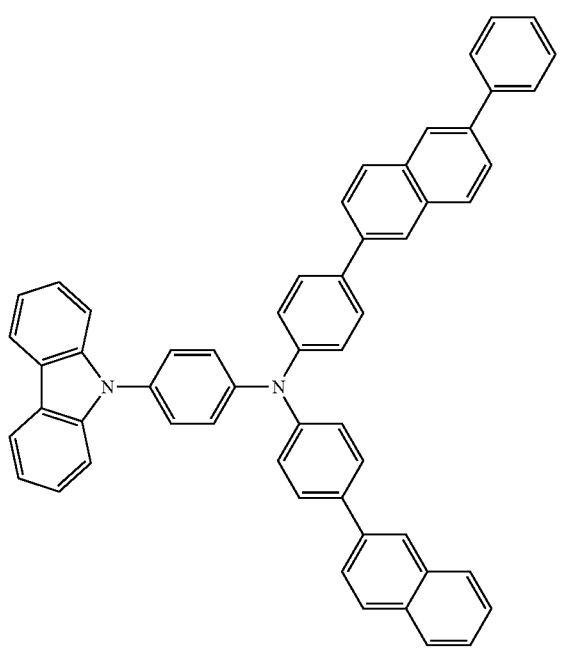

87
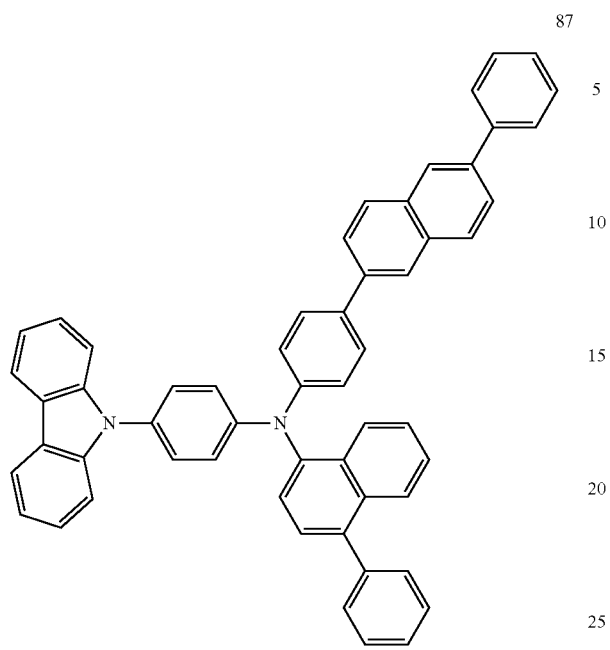
89
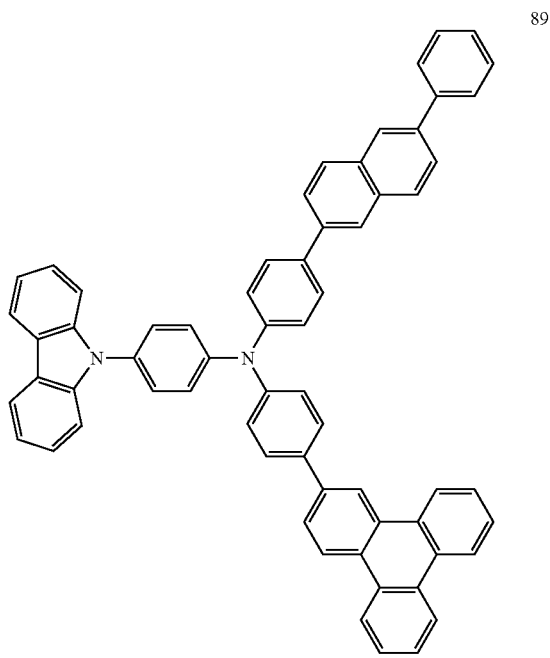
88
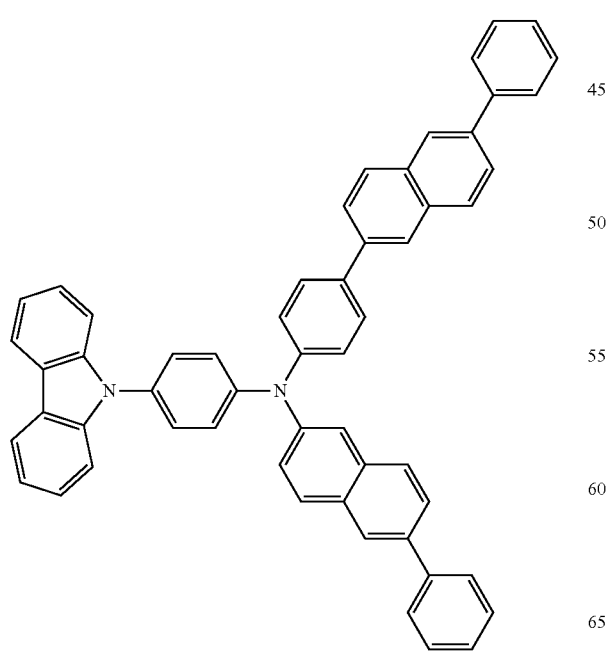
90
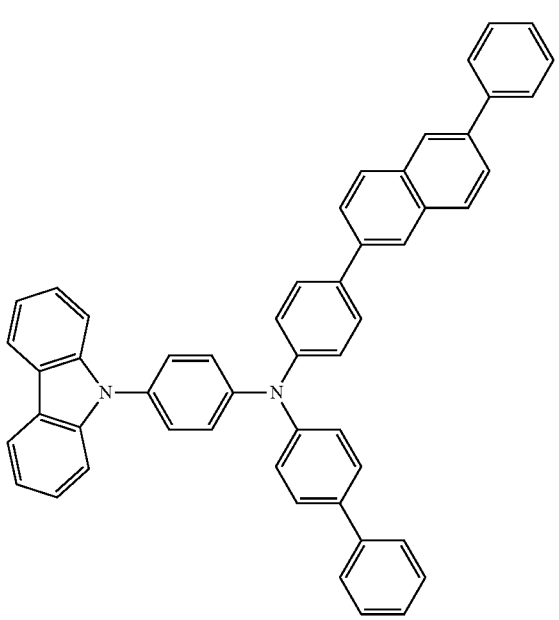

153
-continued
91
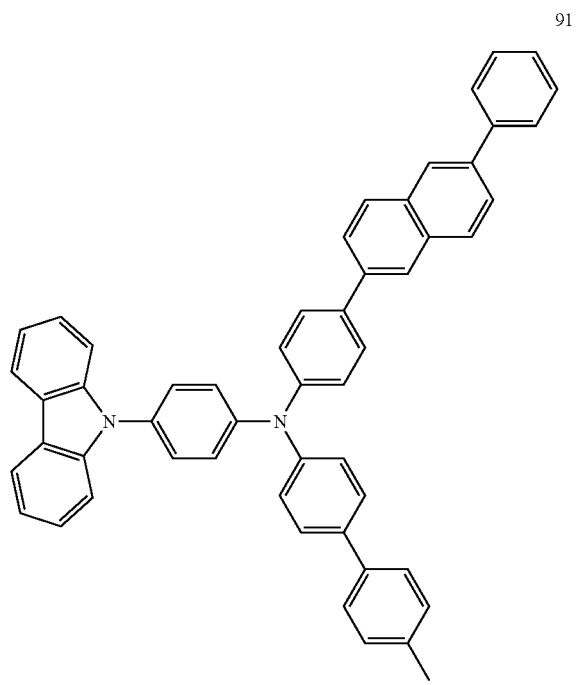
92
93
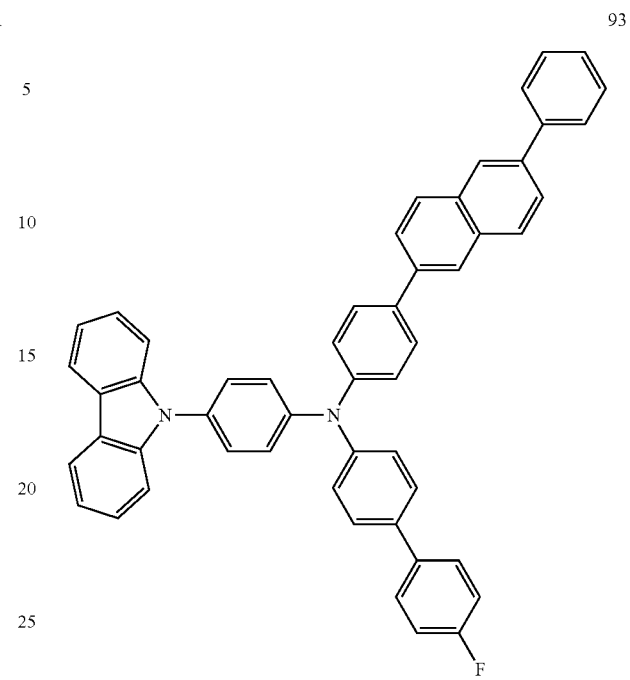
94
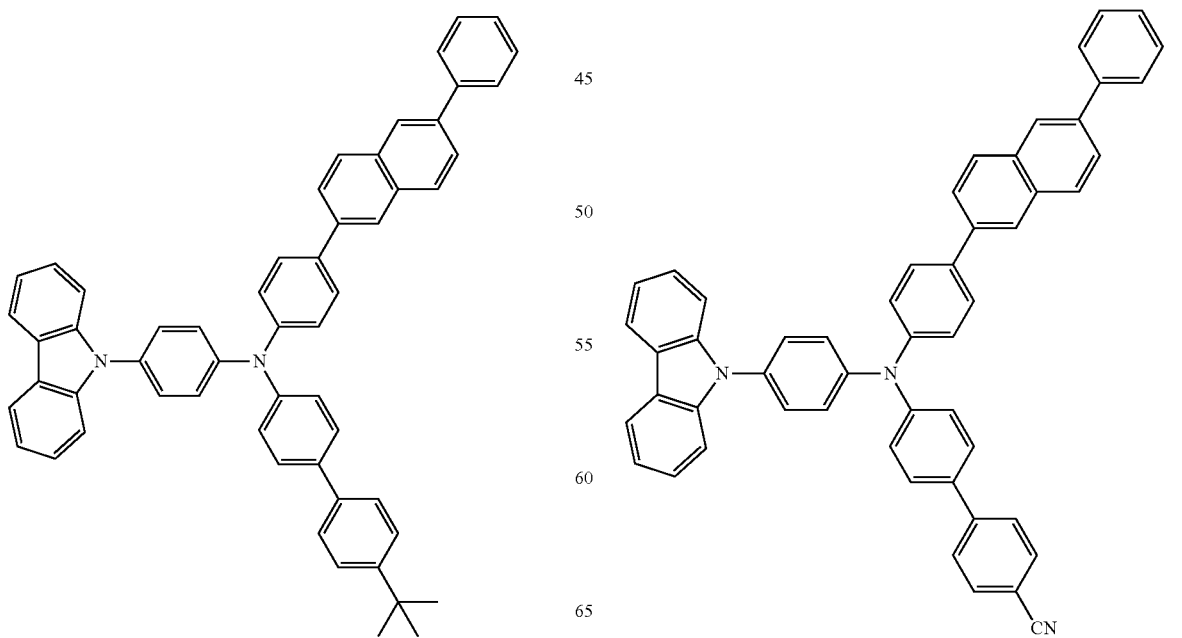

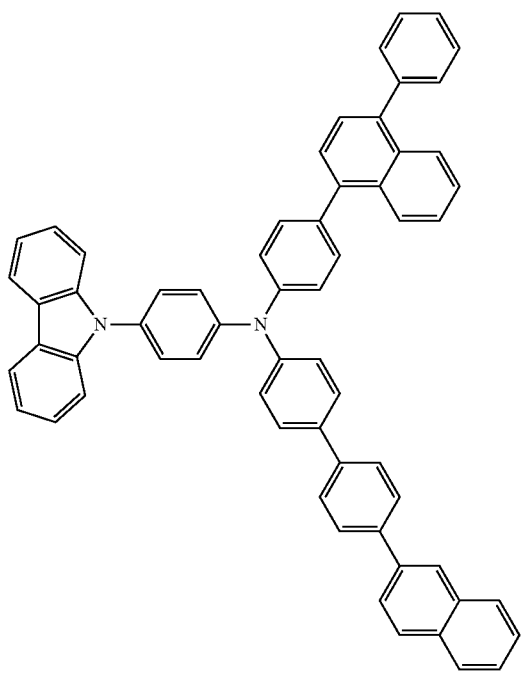
95
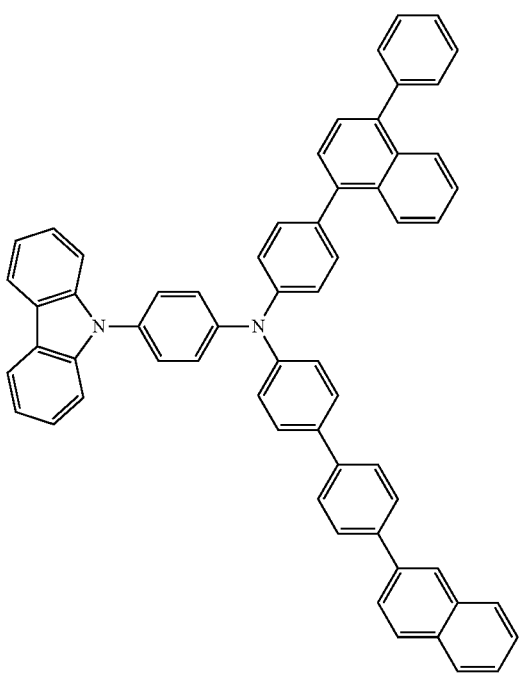
97
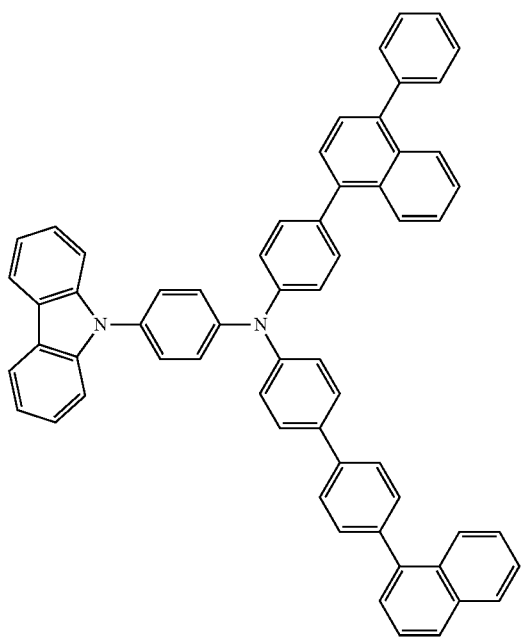
96
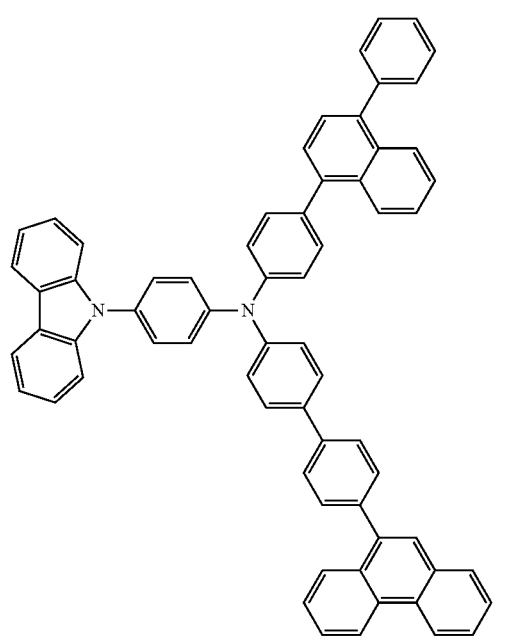
98

99
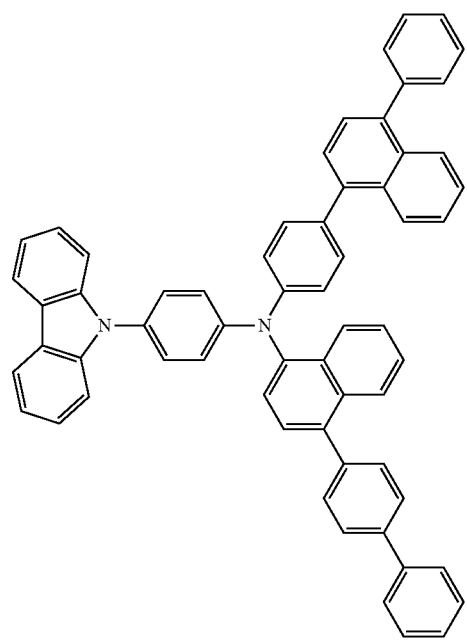
101
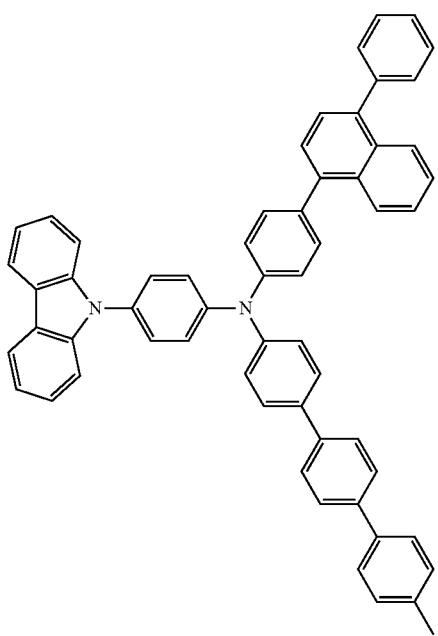
100
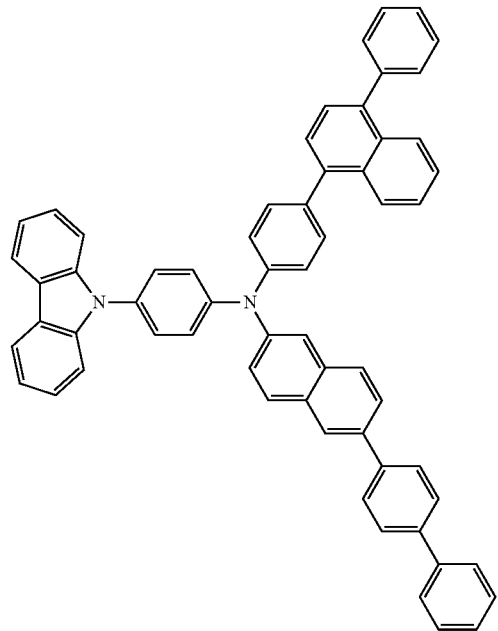
102
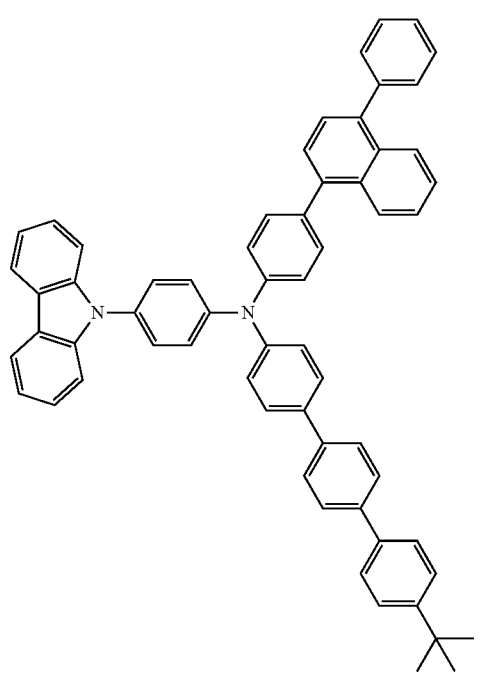

-continued
103
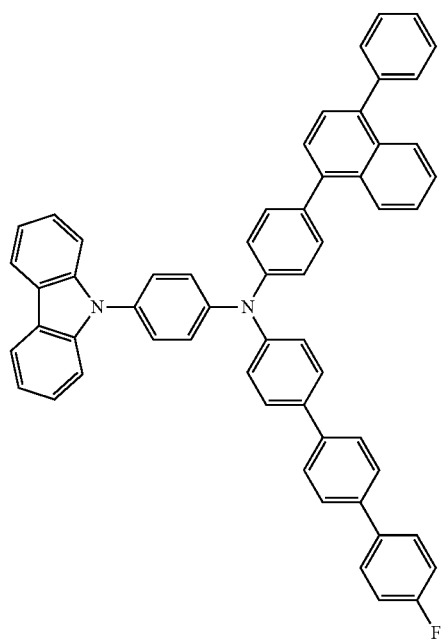
104
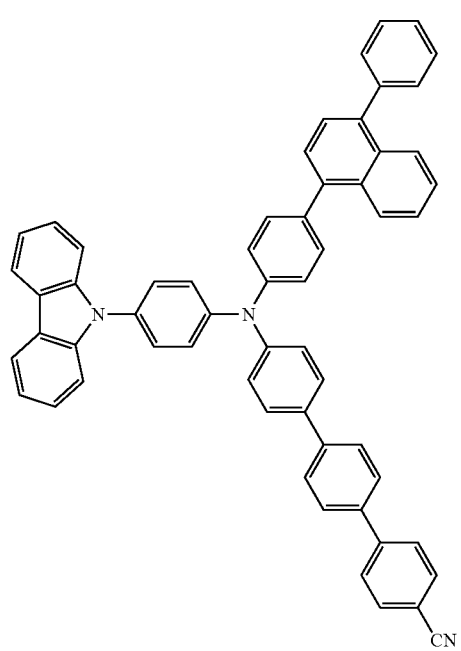
-continued
105
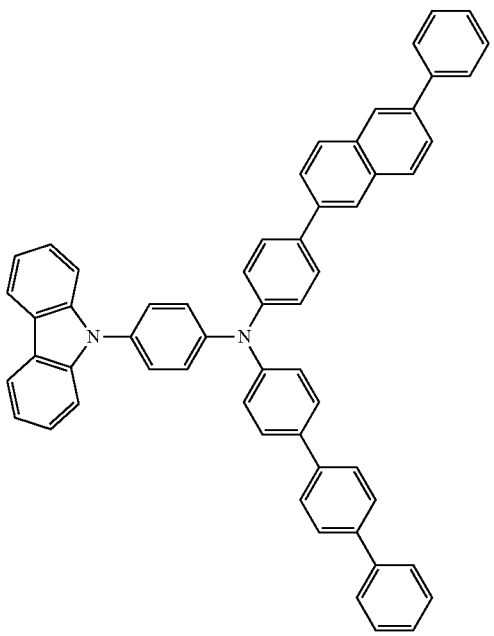
106
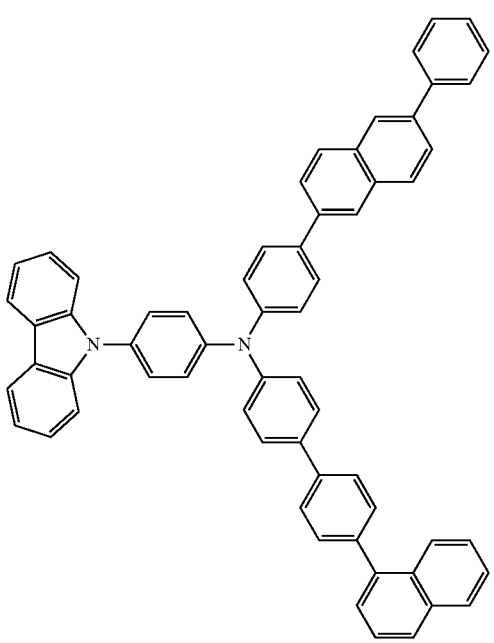

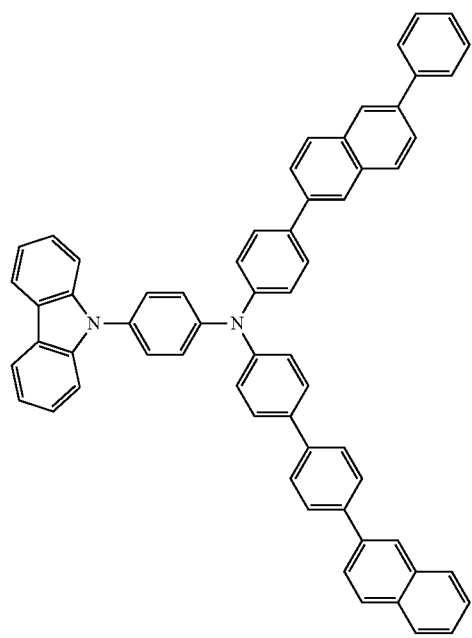
107
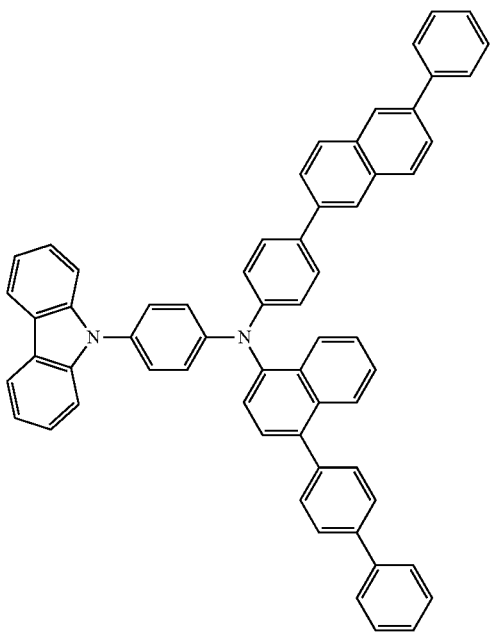
109
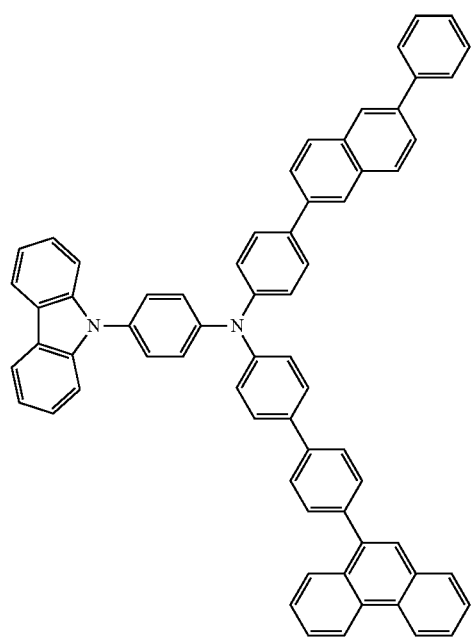
108
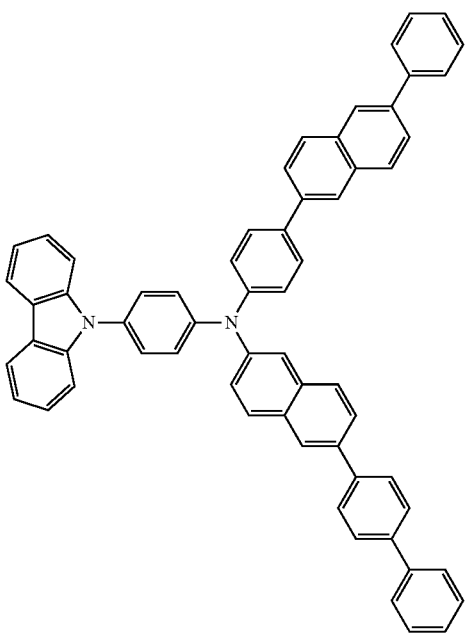
110

111
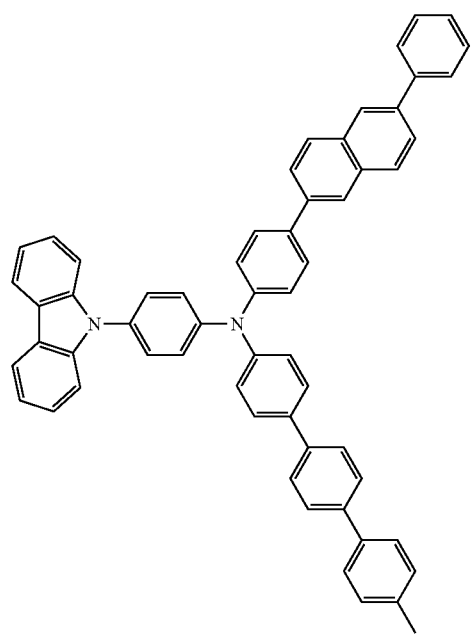
113
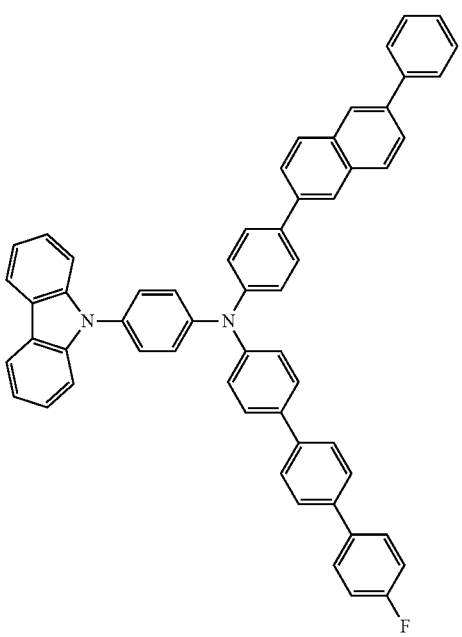
112
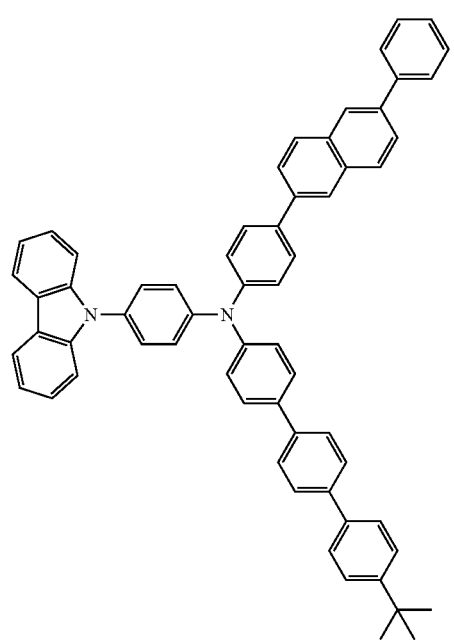
114
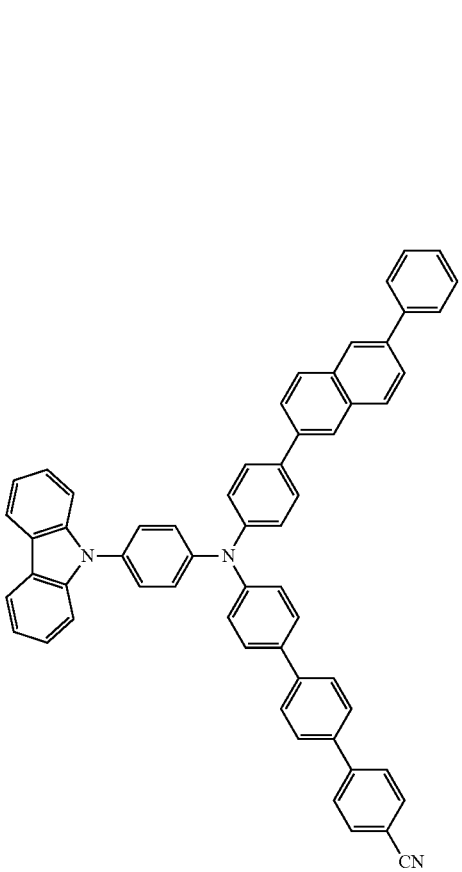

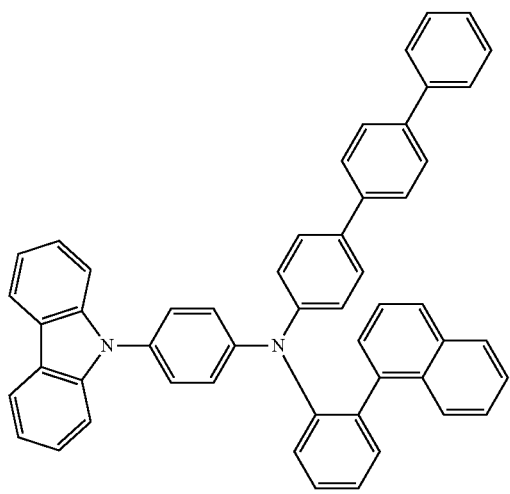
115
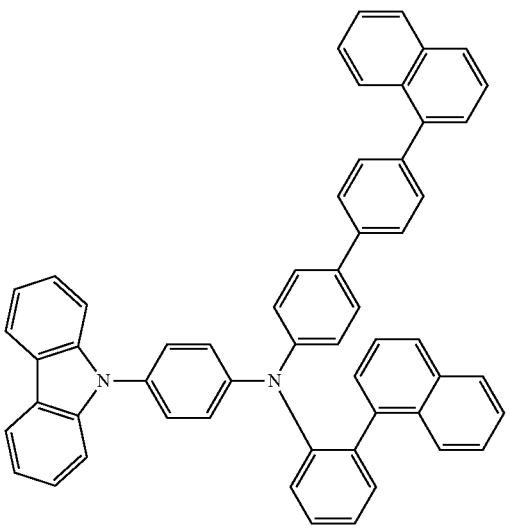
118
116
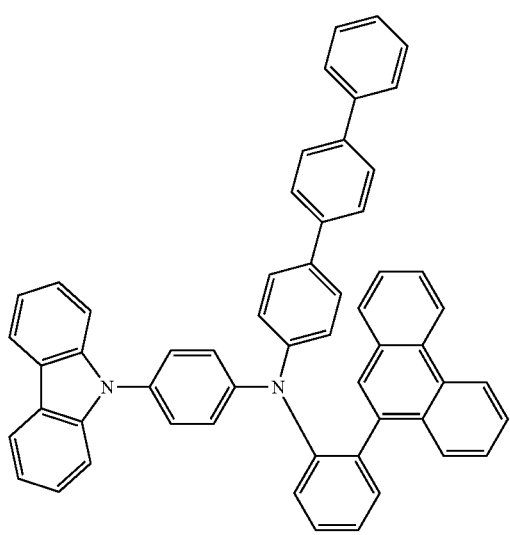
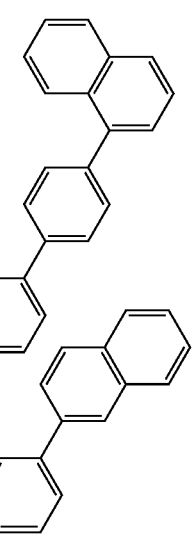
119
117
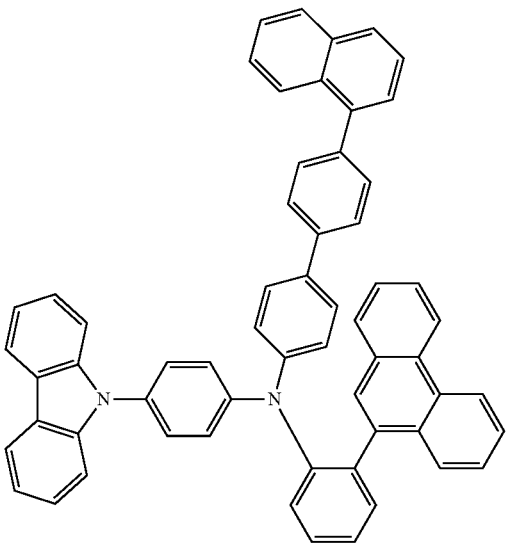
120

121
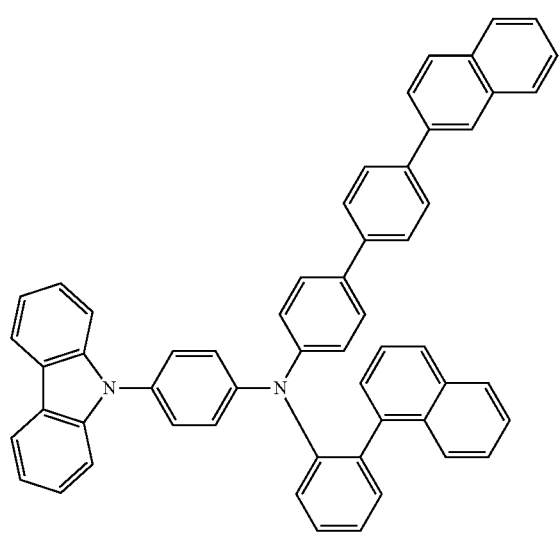
122
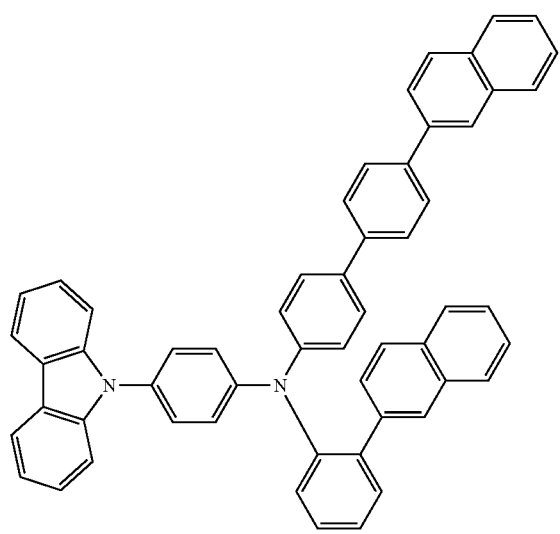
123
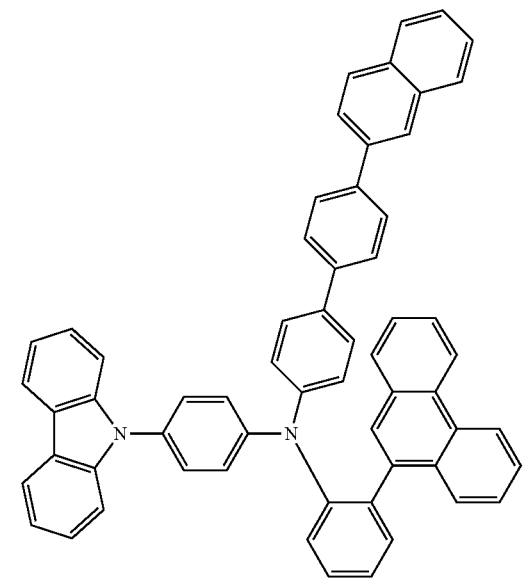
124
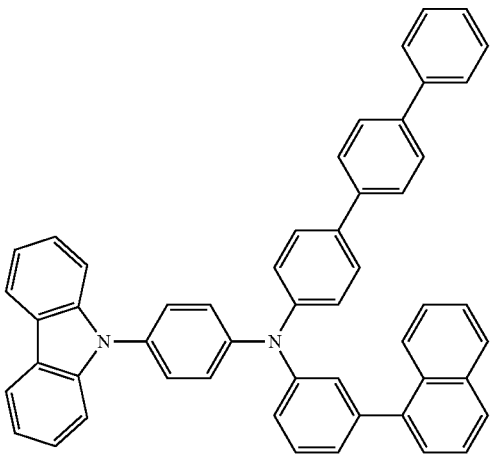
125
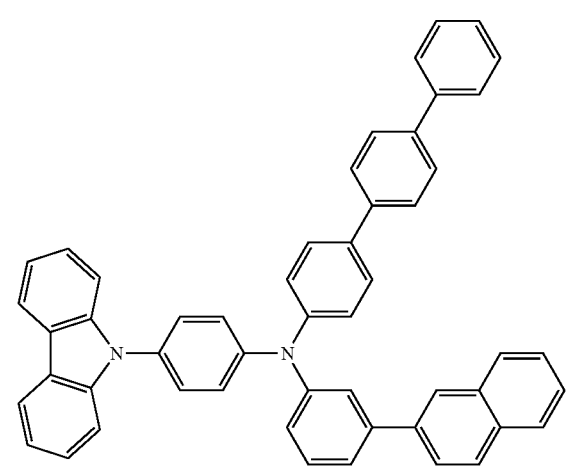
126
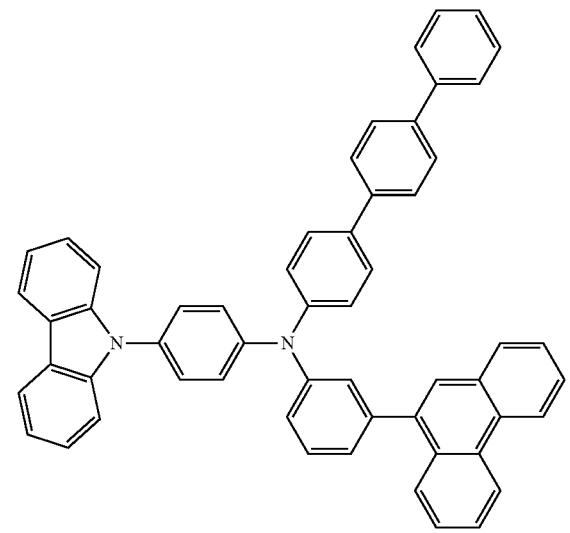

127
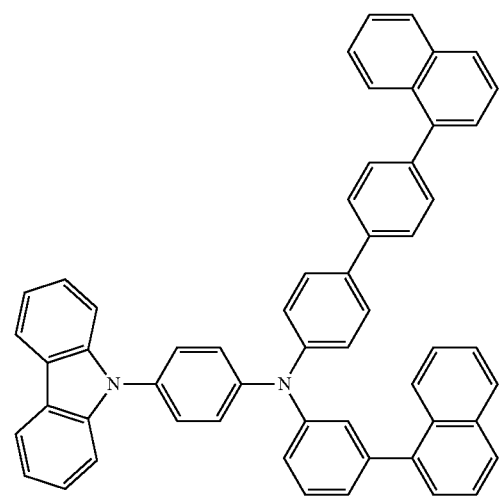
128
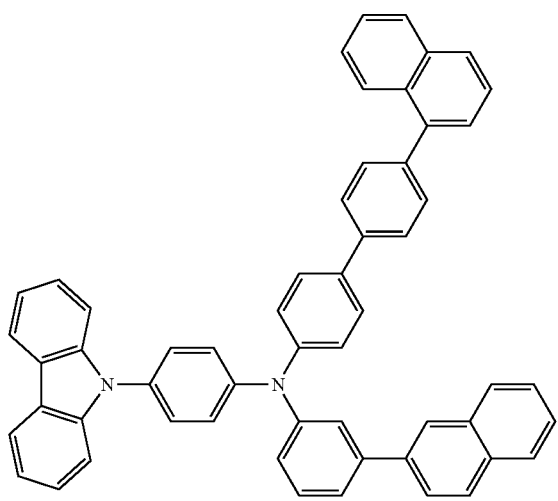
129
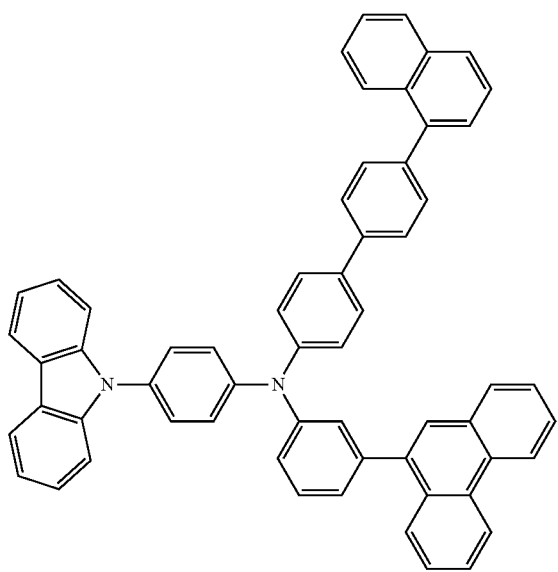
130
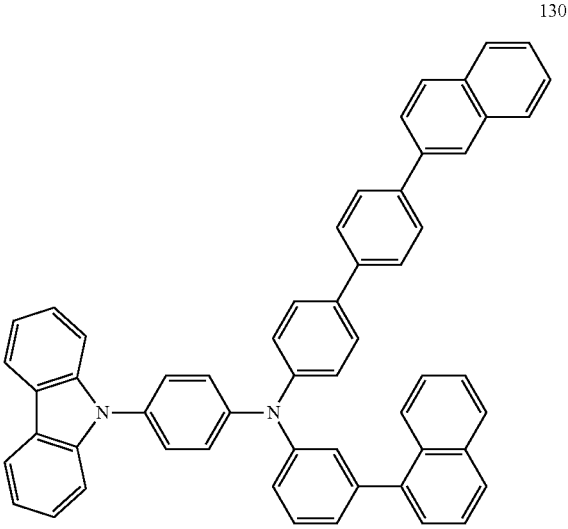
131
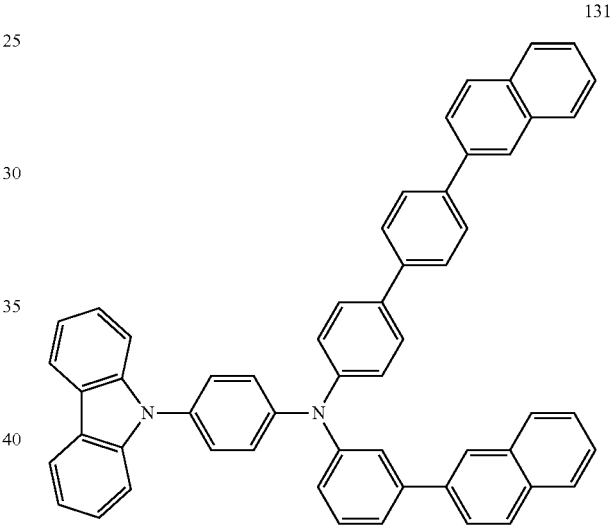
132
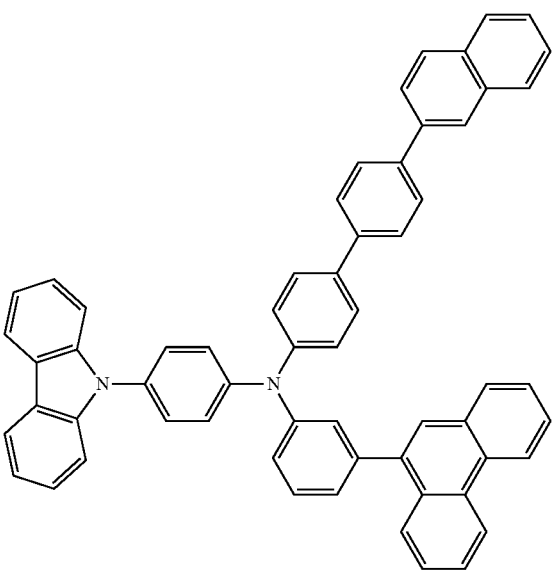

133
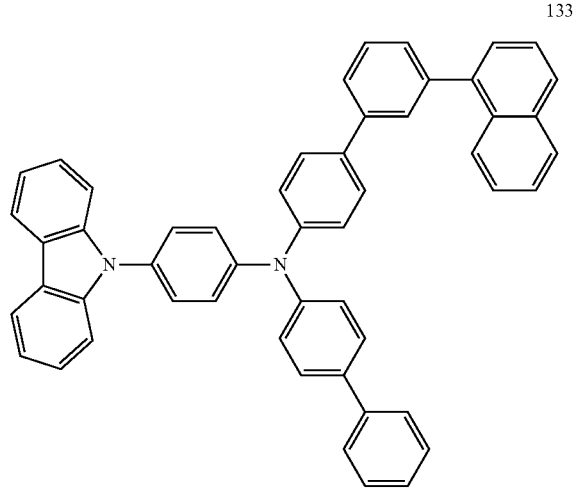
134
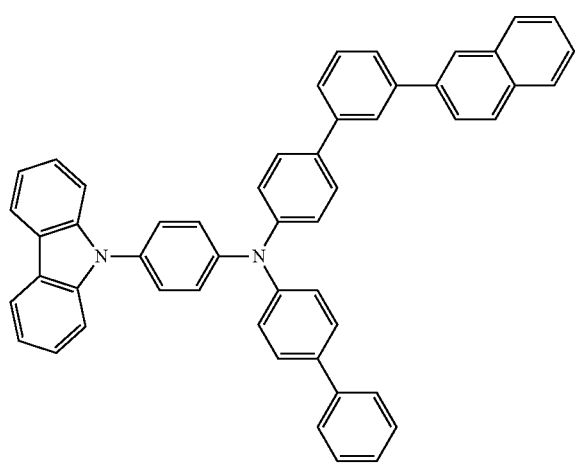
135
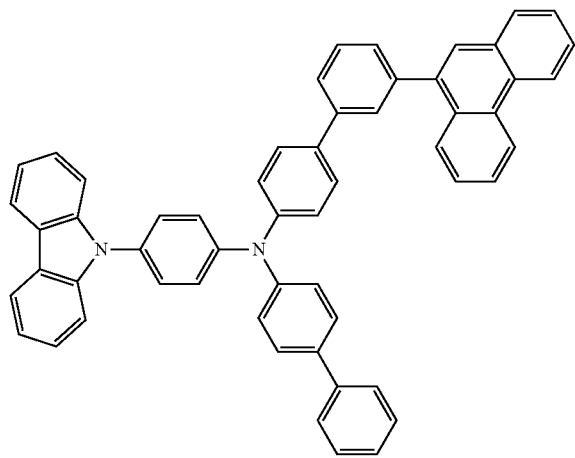
136
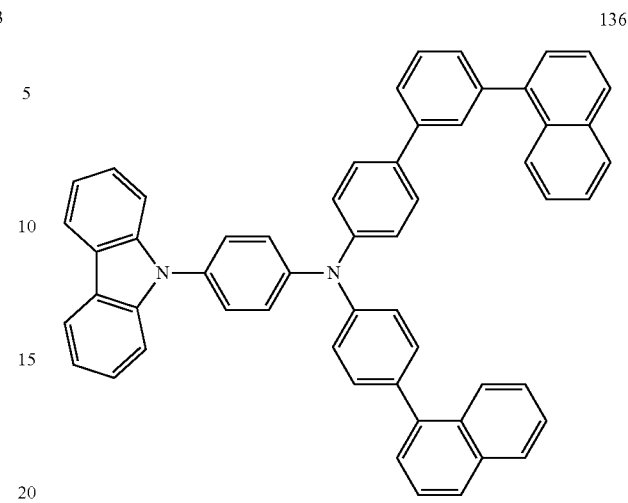
137
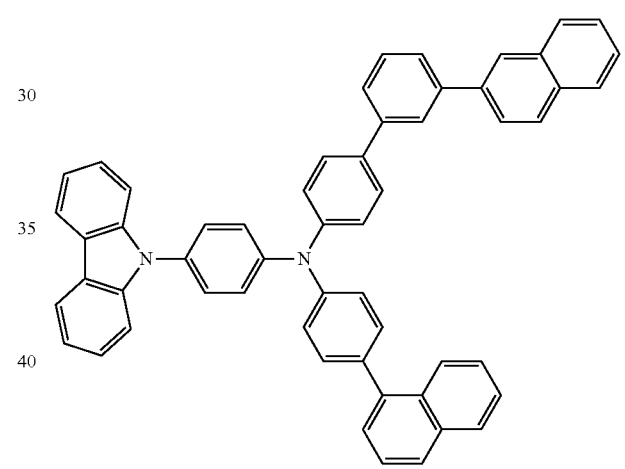
138
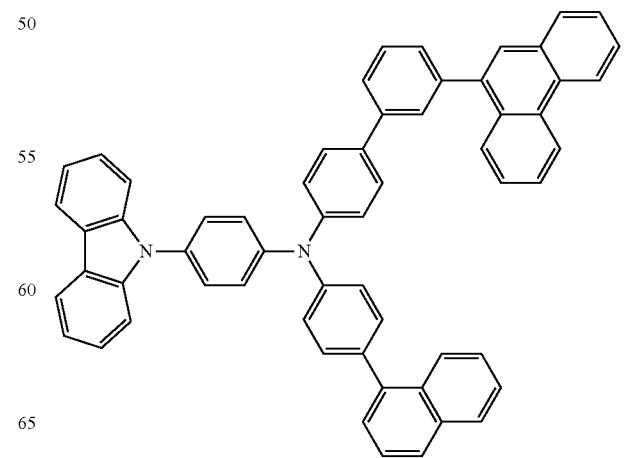

-continued
139
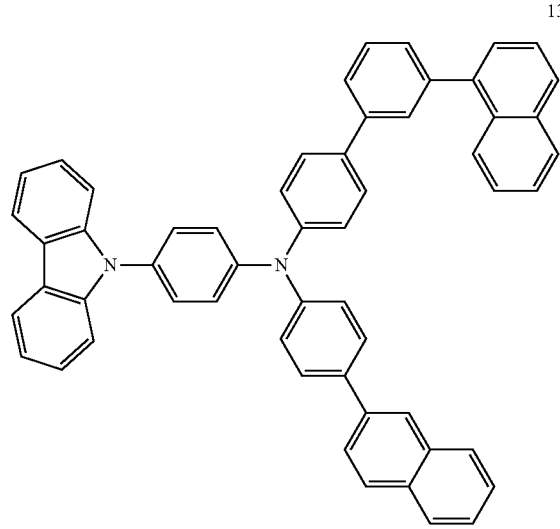
140
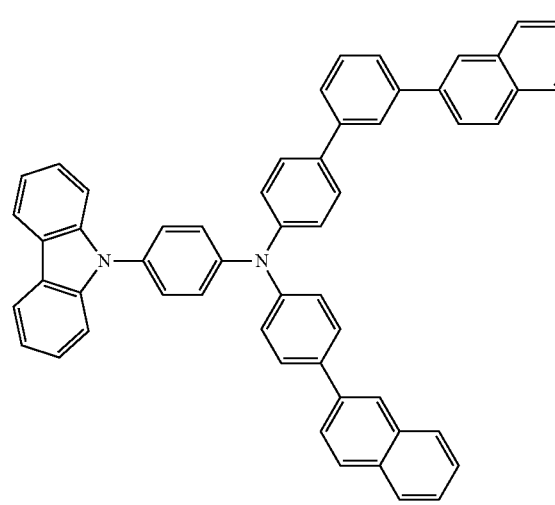
141
142
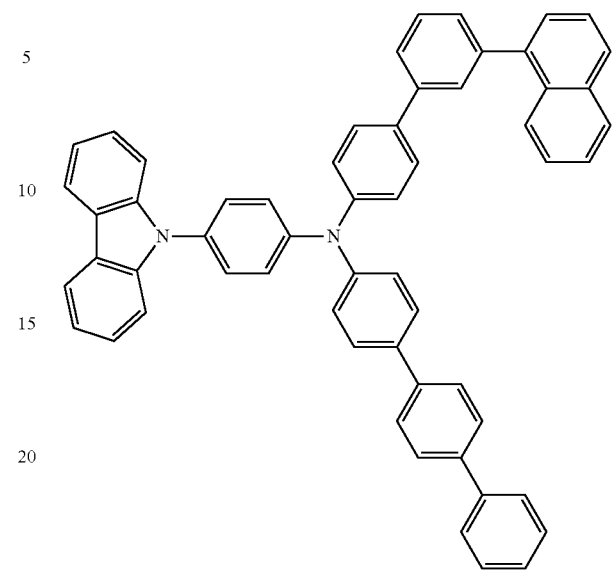
143
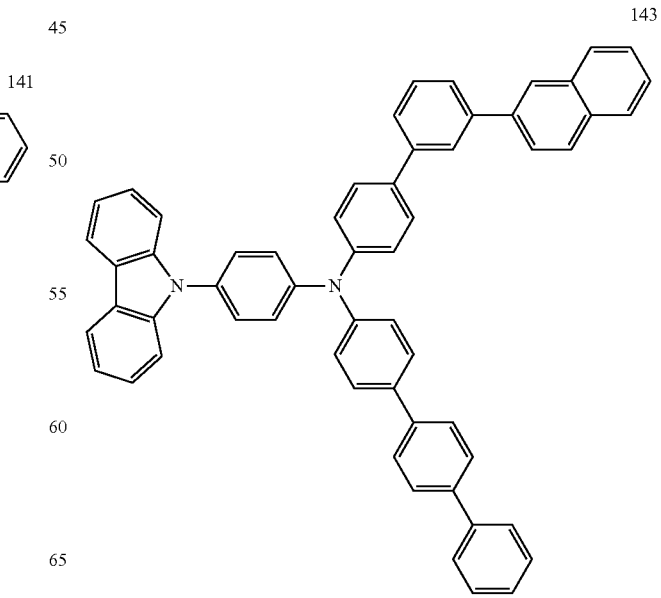

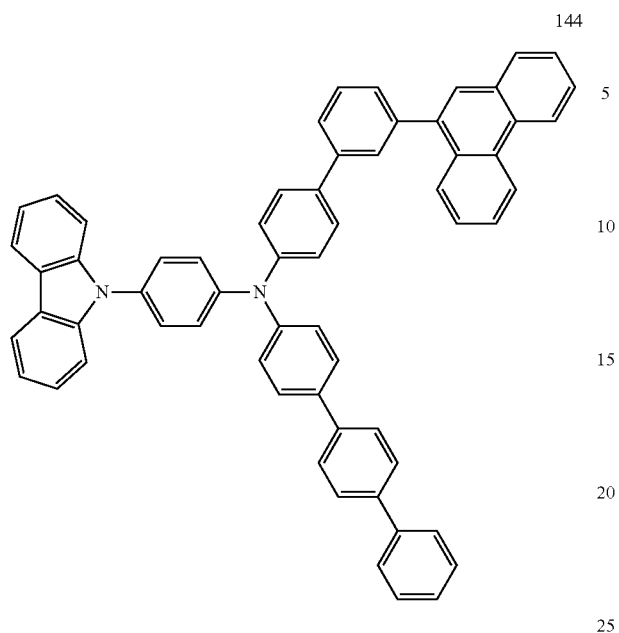
144
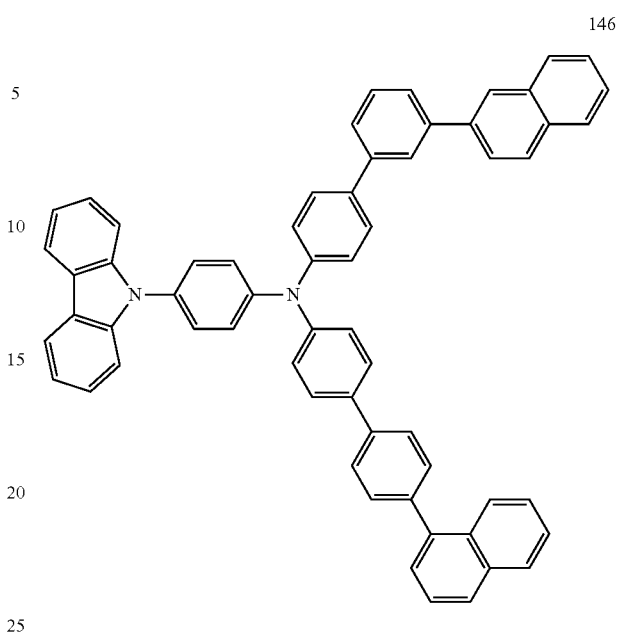
146
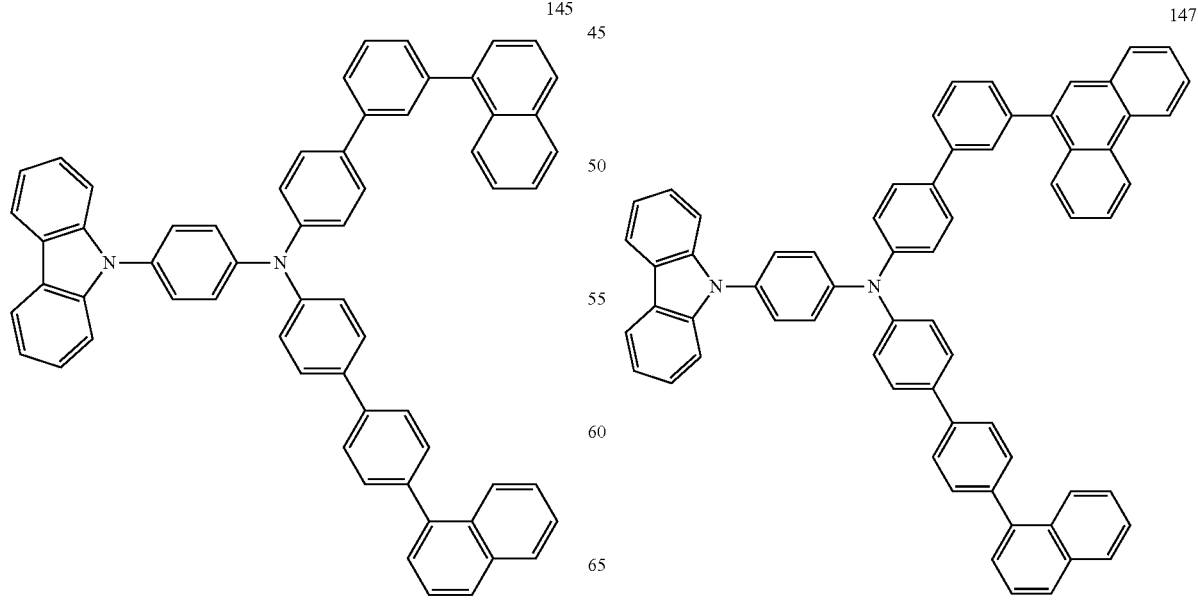

-continued

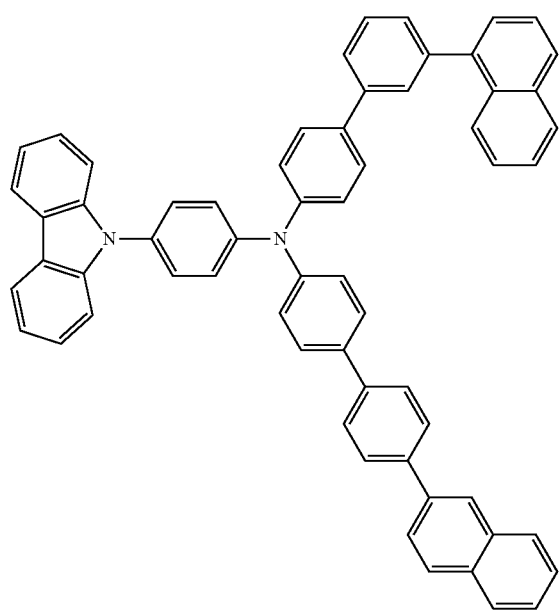

148

149

-continued

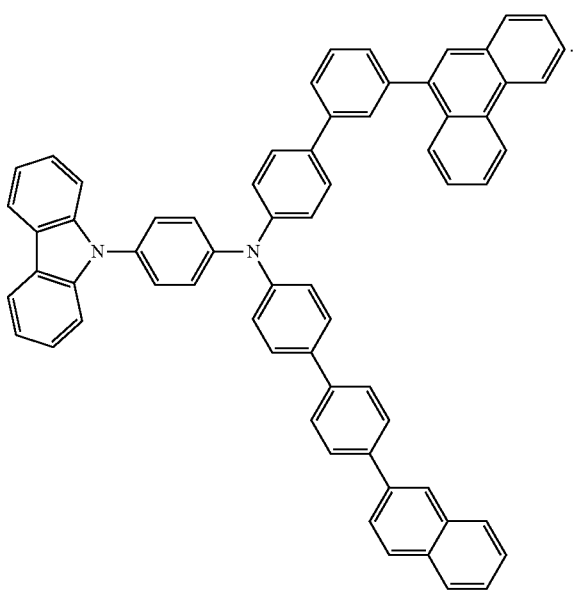

150

10. An organic electroluminescent device, comprising:
a first electrode;
a second electrode;
at least one organic layer between the first electrode and the second electrode, the at least one organic layer including a light emission layer, and a hole transport layer and a hole transport auxiliary layer between the first electrode and the light emission layer; and
a driving thin film transistor including an active layer electrically connected to the first electrode,
wherein the hole transport auxiliary layer includes a compound represented by the following Chemical Formula 1:

Chemical Formula 1

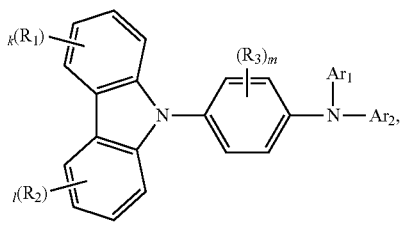

$Ar_1$ is represented by the following Chemical Formula 2:

Chemical Formula 2

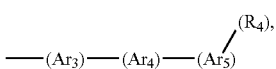

$Ar_2$ is represented by the following Chemical Formula 3:

Chemical Formula 3

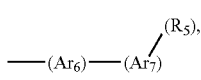

wherein:

each of $Ar_3$ to $Ar_7$ is independently a substituted or unsubstituted C3 to C30 aryl group, and at least one of $Ar_3$ to $Ar_7$ represents a substituted or unsubstituted C8 to C30 aryl group, each of $R_1$ to $R_5$ is independently selected from the group consisting of hydrogen, deuterium, substituted or unsubstituted C1 to C30 alkyl, substituted or unsubstituted C3 to C30 cycloalkyl, substituted or unsubstituted C6 to C30 aryl, and substituted or unsubstituted C2 to C30 heteroaryl, and each of k, l and m is independently an integer of 0 to 4.

11. The organic electroluminescent device of claim 10, wherein the at least one organic layer further includes at least one layer selected from the group consisting of a hole injection layer, an electron transport auxiliary layer, an electrode transport layer and an electron injection layer.

\* \* \* \* \*